United States Patent [19]

Canas-Rodriquez

[11] 4,208,531

[45] Jun. 17, 1980

[54] SYNTHETIC AMINOGLYCOSIDES

[76] Inventor: Antonio Canas-Rodriquez, 8 Saint Martin's Pl., Canterbury, England, CT1 1QD

[21] Appl. No.: 804,756

[22] Filed: Jun. 8, 1977

[30] Foreign Application Priority Data

Jun. 10, 1976 [GB] United Kingdom ............... 24002/76
Nov. 2, 1976 [GB] United Kingdom ............... 45492/76

[51] Int. Cl.$^2$ ..................... A61K 31/71; C07H 15/22
[52] U.S. Cl. ................................ 536/17 R; 424/180; 536/4; 536/10
[58] Field of Search ................................ 536/4, 17, 10

[56] References Cited

U.S. PATENT DOCUMENTS

| | | | |
|---|---|---|---|
| 4,029,883 | 6/1977 | Hiraga et al. ............................. | 536/4 |
| 4,031,210 | 6/1977 | Chazan et al. .......................... | 536/17 |
| 4,051,315 | 9/1977 | Godfrey et al. ........................ | 536/17 |
| 4,063,015 | 12/1977 | Mallams ................................. | 536/17 |

*Primary Examiner*—Johnnie R. Brown
*Attorney, Agent, or Firm*—Wenderoth, Lind & Ponack

[57] ABSTRACT

Novel pseudotrisaccharides based on 2-deoxy- and 2,5-dideoxystreptamine are described. The compounds of the invention can be considered as modified Kanamycin, Gentamycin and Apramycin compounds. In particular they are deoxy derivatives especially at the 2', 3', 4', 2", 3" and/or 4" and/or possibly at the 6' or 6" positions. The compounds are active bactericides some of which are more active than Kanamycin. It is a particular advantage of the compounds that they are active against Kanamycin resistant bacteria. Methods of making these compounds are also described based on glycosylation reaction from corresponding monosaccharide compounds.

8 Claims, No Drawings

SYNTHETIC AMINOGLYCOSIDES

The present invention relates to aminoglycosides. In particular the invention relates to pseudotrisaccharides having antibiotic activity.

The well known antibiotics of the Kanamycin, Gentamycin and Apramycin types are amino-pseudotrisaccharides. The known antibiotics have activity against a wide variety of bacteria. However, strains of bacteria are becoming prevalent which have resistance to these types of antibiotics. This is a significant problem because the resistant strains of bacteria tend to produce more dangerous toxins than the non-resistant strains. The present invention is based on the discovery that by substituting at least partly deoxy rings for the normal rings in these antibiotics can give compounds which have significantly increased activity as compared with the corresponding known antibiotics against such resistant microorganisms.

Antibiotics of the Kanamycin, Gentamycin and Apramycin types are pseudotrisaccharides based on 2-deoxystreptamine:

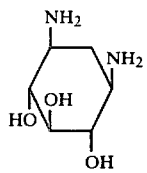

In Kanamycin and Gentamycin antibiotics this ring is substituted with monosaccharide (or pseudomonosaccharide) rings in the 4-and 6-positions and in Apramycin antibiotics this ring is substituted with a disaccharide (or pseudodisaccharide) ring in the 4- or 5-position. In antibiotics of this type the glycosidic bands are α, and the substituents in the rings are equatorial.

In antibiotics of this invention the pseudomonosaccharide residues other than streptamine residues can be either in their D- or L- forms. Generally, for convenience, in this specification the compounds will be described and illustrated in their D-forms but it is to be understood that such references include the L-forms and mixtures, such as racemic mixtures, of the two forms.

The present invention provides a compound being a pseudotrisaccharide of the general formula:

[A]—[B]—[C]

or

[A]—[C¹]—[A¹]

where
[A] is a group of the formula:

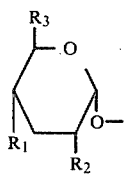

where $R_1$ is H, F, OH or SH;
$R_2$ is H or $NH_2$; and
$R_3$ is H or —$CH_2$—$R_4$ is OH or $NH_2$;
provided that when $R_2$ is H, $R_3$ —$CH_2$—$NH_2$, and when $R_3$ is H or —$CH_2$—OH $R_2$ is $NH_2$;
[A¹] is a group of the formula:

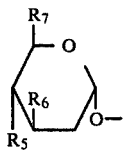

where
$R_5$ is H, OH, SH or halogen, preferably F;
$R_6$ is H, OH or NH $R_8$ where $R_8$ is H or Me; and
$R_7$ is H or —$CH_2$—$R_9$ where $R_9$ is H, OH or $NH_2$;
provided that when $R_6$ is H or OH $R_7$ is —$CH_2$—$NH_2$ and when $R_7$ is H or —$CH_2$—OH $R_6$ is NH $R_8$;
[B] is a group of the formula:

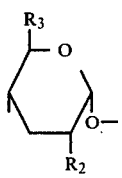

where $R_2$ and $R_3$ are as defined for [A];
[C] is a group of the formula

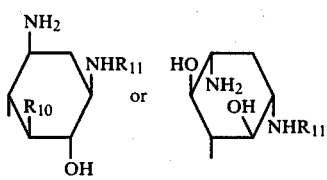

where $R_{10}$ is H or OH and $R_{11}$ is H, $CH_3$ or —CO—CHOH —$CH_2$—$CH_2$—$NH_2$; and
[C¹] is a group of the formula:

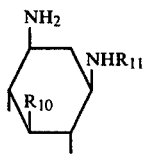

where $R_{10}$ and $R_{11}$ are as defined for [C]
wherein both glycosidic bonds are α-glycosidic bonds, and the pharmaceutically acceptable acid addition salts thereof.

The present invention includes a method of making a compound of the invention which comprises reacting together, in a manner known per se for analogous compounds, corresponding protected precursor monosaccharides or pseudomonosaccharides to form a protected pseudotrisaccharide wherein the glycosidic linkages are α-glycosidic and subsequently removing the protecting groups to liberate the compound of the invention. This method can be performed in two stages, by first reacting together two protected monosaccharide units to give a protected disaccharide unit and subsequently reacting this with a further monosaccharide unit to give the protected pseudotrisaccharide. This method is generally applicable to the compounds of the invention. A further possibility particularly applicable to Kanamycin analogues where the two terminal monosaccharide residues in the eventual protected pseudotrisaccharide are the same is to react an difunctional protected pseudomonosaccharide corresponding to the middle residue in the product with two molar equivalents of a monofunctional protected monosaccharide corresponding to the terminal residues. Usually an excess of the monofunctional compounds will be used in order to drive the reaction more in favour of the tri- rather than di-saccharide possible products.

As will be apparent to the man skilled in the art some of the compounds of the invention are interconvertible with other compounds of the invention. In particular -OH groups can be converted into $NH_2$ or SH groups or halogen atoms by procedures known in the art. Also compounds directly corresponding to compounds of the invention but having OH groups in some places where the compounds of the invention have $NH_2$ groups can be converted into compounds of the invention by procedures known in the art. In this situation the OH groups are for the purpose of the invention considered to be protecting groups.

The Kanamycin analogues of the invention having an $NH_2$ group in the 3″-position can be converted into Gentomycin analogues by N-methylation of this amino group by procedures known in the art. The compounds of the invention where $R_{11}$ is other than hydrogen can also be made from the corresponding free amino compounds by known methods.

As will be apparent from the formulae given above the compounds of the invention contain a minimum of 4 and a maximum of 6 amino groups. The preferred compounds of the invention have 5 amino groups. In particular in the group $A^1$ the radical $R_6$ is very preferably an amino group.

The most preferred compounds of the invention are those set out below:

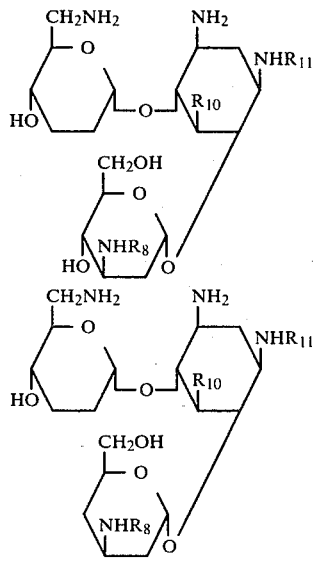

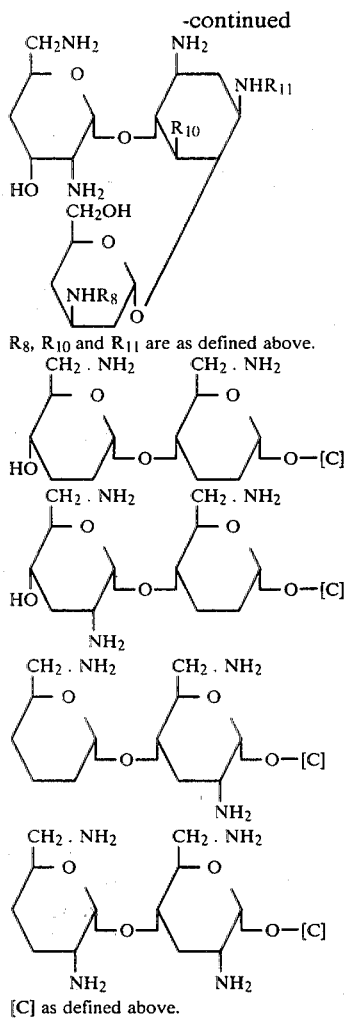

$R_8$, $R_{10}$ and $R_{11}$ are as defined above.

[C] as defined above.

The compounds of the invention can be made by general synthetic procedures which are well understood in carbohydrate chemistry. Many of the compounds used as intermediates are believed to be novel. The synthetic routes can be considered in two parts, first the synthesis of the intermediate monosaccharides or pseudomonosaccharides and second the reaction of these compounds of give the pseudotrisaccharides of the invention. In both parts of the overall syntheses it will be necessary or desirable to stereoselectively protect various of the reactive groups in the molecule in order to react others of the groups unambiguously. As is understood in the art, protecting groups used during the synthesis must be able to adequately mask the reactive group to which they are attached and must also be removable under relatively mild conditions in particular such as will not affect the glycosidic bond e.g. alkaline hydrolysis, hydrogenolysis or very mild acid treatment.

Suitable groups for protecting hydroxyl functions include the following groups: acetyl, benzoyl, trifluoroacetyl, 2-chloroacetyl, methoxycarbonyl, 2,2,2-trichloroethoxycarbonyl, benzyl and any nuclear substituted benzyl group, methyl-thio-methyl- and allyl.

Suitable groups for protecting amino functions include the following groups (named including the amino nitrogen atom): N,N-dibenzyl; N-benzyl-N-alkoxycarbonyl preferably where the alkyl group is methyl benzyl or 2,2,2-trichloroethyl; N-phthalimido; N-succinimido; N-o-benzoyloxymethylbenzoyl; N-acetyl; N-2,2,2-trifluoroacetyl; N-benzyloxycarbonyl and N-2,2,2-trichloroethoxycarbonyl.

For vicinal diol groups of α-amino alcohol functions suitable protecting systems include forming a cyclic carbonate or carbamate or a 1,3-dioxolane ring e.g. in a cyclohexylidene or isopropylidene system, this latter being particularly preferred because of the ease with which it can be hydrolysed under mildly acidic conditions and the commercial availability of the reagent, 2,2-dimethoxypropane.

As will be appreciated by the man skilled in the art the individual reactions in the schemes below are well known. Further, the schemes set out below exemplify the production of the relevant compounds and are not exhaustive. Equivalent reactions for many of the stages will be apparent to the man skilled in the art and are not included or discussed in detail here to avoid undue lengthening of the description.

The ring system common to all the compounds of the invention is the deoxystreptamine ring either in the form of 2-deoxystreptamine or 2,5-dideoxystreptamine. For glycosidic coupling these compounds are provided, only 4-, 5-(if present) or 6-hydroxyl group remaining unprotected. These compounds can be synthesized from 2-deoxystreptamine itself or compounds containing it as a residue e.g. Kanamycine or Neomycin.

A suitably protected 4-hydroxy-2-deoxystreptamine can be prepared from the known compound 5,6-O-cyclohexylidene tetra-N-methoxycarbonylenamine by the sequence described below and illustrated in Scheme 1a. This compound upon periodate oxidation gives a dialdehyde which can be degraded by an akali e.g. an alkaline or alkaline earth metal alcoholate e.g. NaOMe or triethylamine to give a substituted 2-deoxystreptamine which can be isolated from the reaction mixture by column chromatography on silica gel with ethyl acetate/chloroform containing ca. 1% triethylamine. Hydrolysis with an alkaline or alkaline earth metal hydroxide, or with 90% hydrazine hydrate, removes the N-methoxycarbonyl groups.

The two amino groups in this compound can be protected by reacting it with N-ethoxycarbonylphthalamide in the presence of triethylamine or aqueous sodium carbonate. The product is 5,6-O-cyclohexylidene-2-deoxy-1,3-diphthalimidostreptamine. An alternative method is to benzylate the product of the degradation reaction rather than to hydrolyse it e.g. with benzyl bromide-sodium hydride in dimethylformamide followed by mild hydrogenolysis (Pd-charcoal, 1 atm) to give 5,6,O-cyclohexylidene-1,3-di-N-benzyl-2-deoxy-1,3-di-N-methoxycarbonylstreptamine.

Scheme 1a

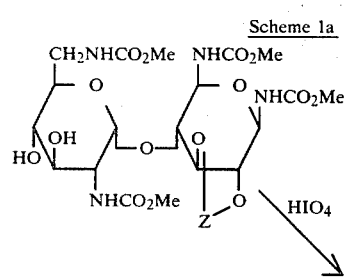

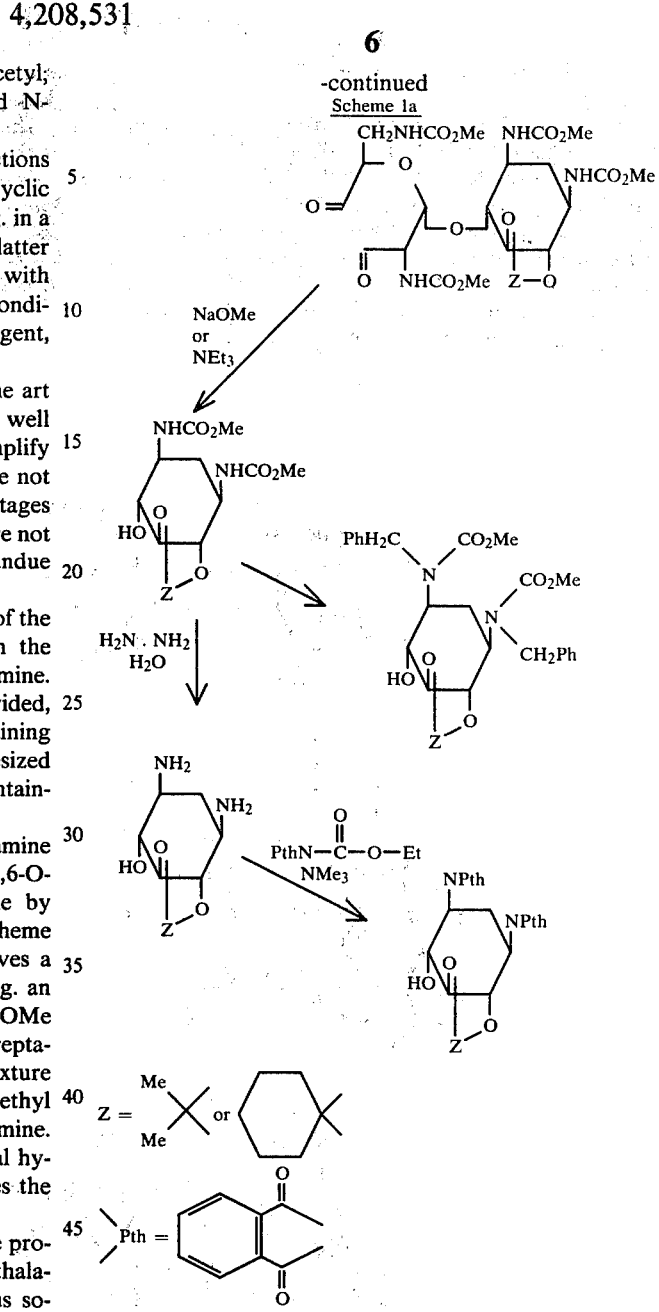

The cyclohexylidene protecting group may be difficult to remove in the final products. It can be converted to the more labile isopropylidene group by mild acid hydrolysis followed by treatment with 2,2-dimethoxypropane and catalytic amounts of toluene-p-sulphonic acid. In this sequence the 4-hydroxyl group should be protected e.g. by benzylation. The benzyl group can be removed by catalytic hydrogenation after the exchange of protecting groups.

Suitably protected 4- and 6-hydroxy-2-deoxystreptamines can be made by this sequence described below and illustrated in Scheme 1b. This sequence starts with 2-deoxystreptamine which is monobenzylated on each nitrogen atom and then methoxycarbonylated with e.g. methylchloroformate. The resulting product is reacted with 1,1-dimethoxycyclohexane. The resulting racemic mixture can be resolved by fractional crystallisation techniques e.g. using optically active seed from ethereal solution. Repetition of the fractional crystallization gives satisfactory separation of the 4-hydroxy and 6-hydroxy isomers.

Synthesis of protected 5-hydroxy-2-deoxystreptamine can be accomplished by the sequence described below and illustrated in Scheme 1c. This sequence starts with 2-deoxystreptamine, which is reacted with benzaldehyde under reducing conditions e.g. using sodium borohydride, sodium cyanoborohydride, hydrogen and palladium-on-charcoal, hydrogen and Raney nicke, etc., to give the di-N-benzylated product streptamine. This compound is transformed into a dicyclic carbamate by reaction with phosgene, phenyl chloroformate, p-nitrophenyl chloroformate or methyl chloroformate, in the presence of a base such as Amberlite 400 (OH⁻), sodium or potassium carbonate, alkaline metal alcoholates or sodium hydride. This intermediate,2-deoxy-1,3-di-N-benzylstreptamine-1,6:3,4-dicarbamate, is a key intermediate for the synthesis of 5-O-glycosidic bonds with 2-deoxy streptamine.

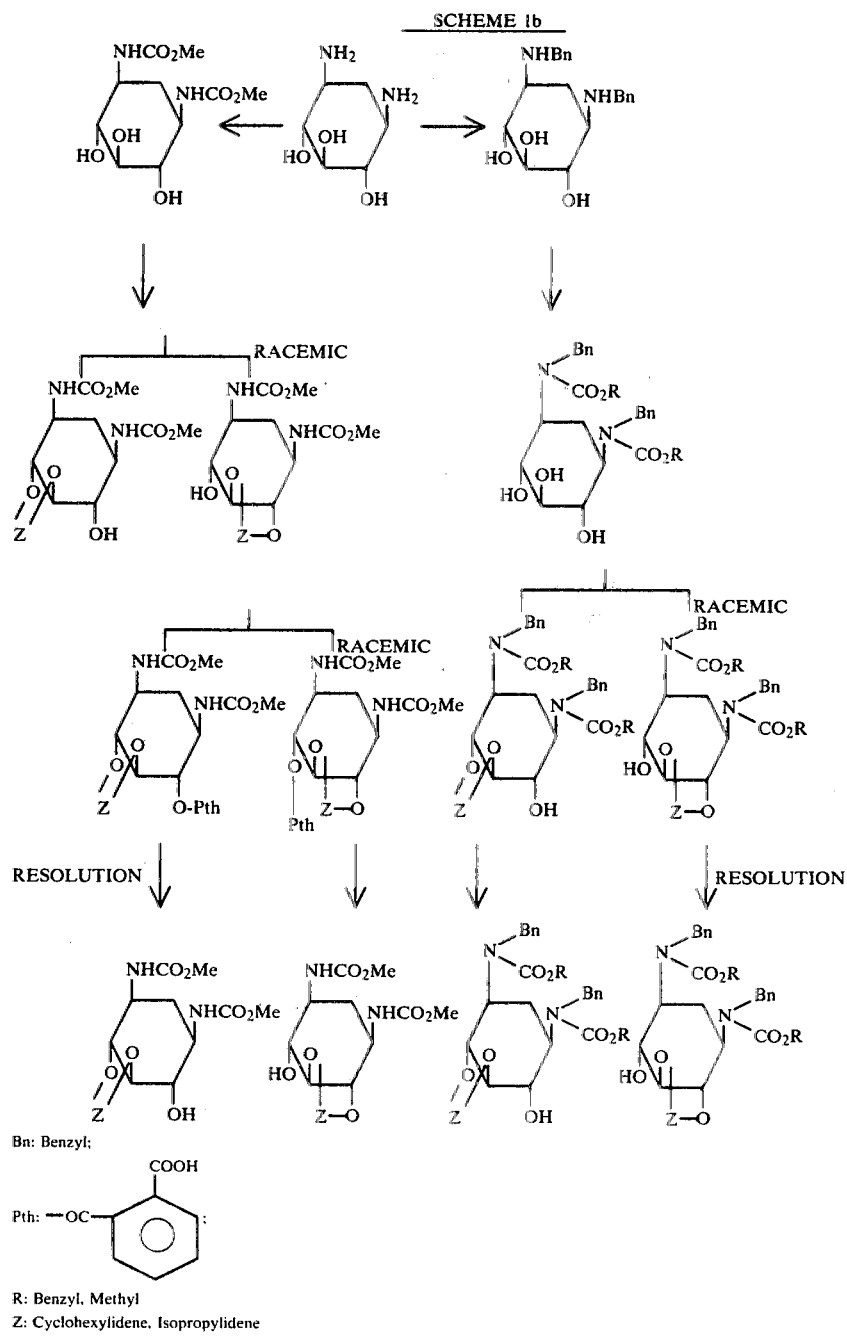

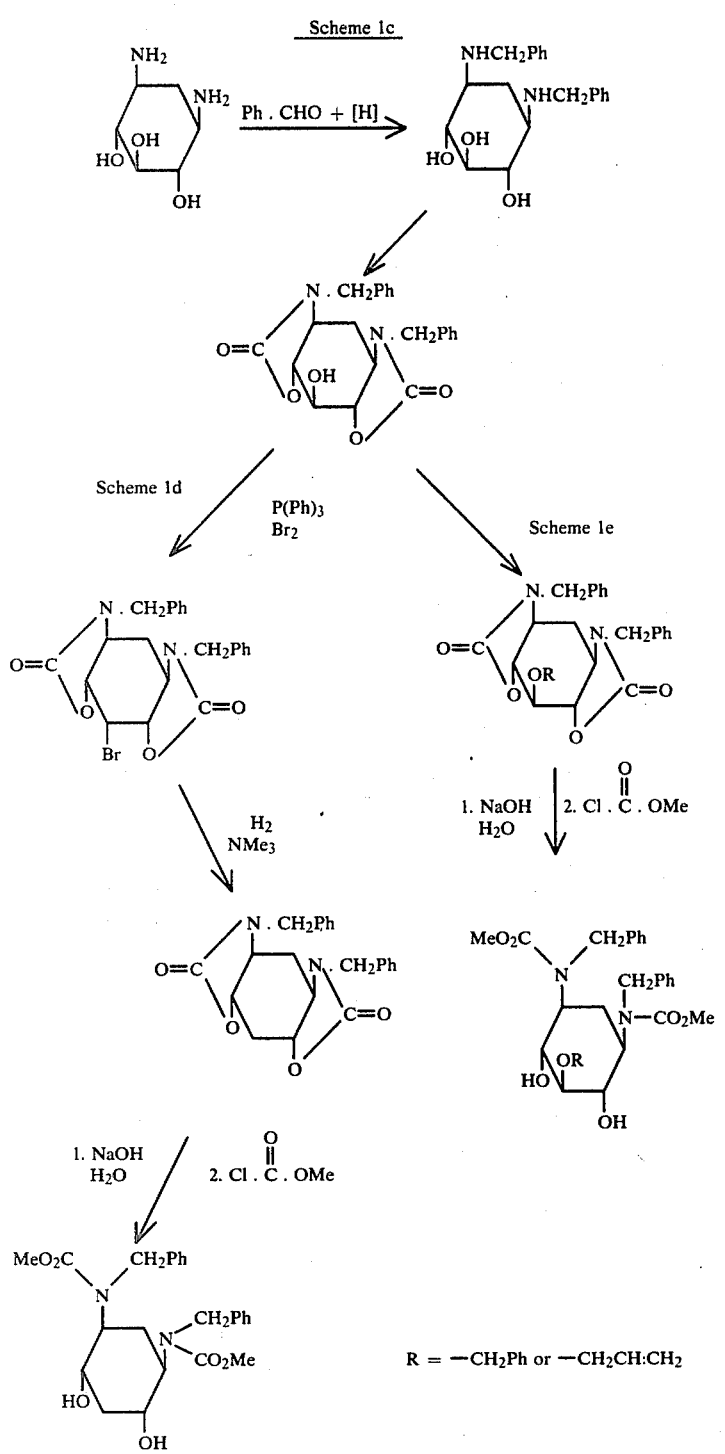

This cyclic dicarbamate can also be used in the synthesis of other intermediates such as is illustrated in reaction Schemes 1d and 1e. In Scheme 1d the cyclic dicarbamate is reacted with an halogenating agent preferably bromine or iodine in the presence of a trivalent phosphorus compound such as triphenylphosphine or a trialkylphosphite. The resulting 5-halogeno compound (the 5-bromo is illustrated) can be reduced e.g. by catalytic hydrogenation in the presence of a base to give a cyclic dicarbamate protected 2,5-dideoxystreptamine. In Scheme 1e the 5-hydroxy group in the cyclic dicarbamate is benzylated or allylated to protect the 5-hydroxyl groups. The cyclic dicarbamate intermediate obtained in Schemes 1d and 1e can be ring opened (as illustrated) by reaction with sodium methoxide in methanol or, preferably, by saponification followed by methoxy carbonylation or benzoxy carbonylation. The products of these two sequences are 4,6-dihydroxy protected streptamines. The product of sequence 1d is important because it is a 2,5-dideoxystreptamine. Where it is desired to have the 4- or 6-monohydroxy derivatives corresponding to these products i.e. with the 6- or 6-hydroxyl group respectively protected, they can be made by standard protection reactions e.g. benzylation followed by resolution of the isomers or changing one of the N-protecting groups to a cyclic group with the hydroxyl group adjacent e.g. a cyclic carbamate followed by resolution of the isomers.

The synthesis of the remaining intermediates needed in the production of the pseudosaccharides of the invention can be effected from known compounds by methods similar to those described above for the preparation of intermediates containing the 2-deoxy- or 2,5-dideoxystreptamine ring. Scheme 2 briefly sets out a series of reaction schemes for the synthesis of some of these intermediates. Suitable reagents and reaction conditions will be apparent to the man skilled in the art.

SCHEME 2

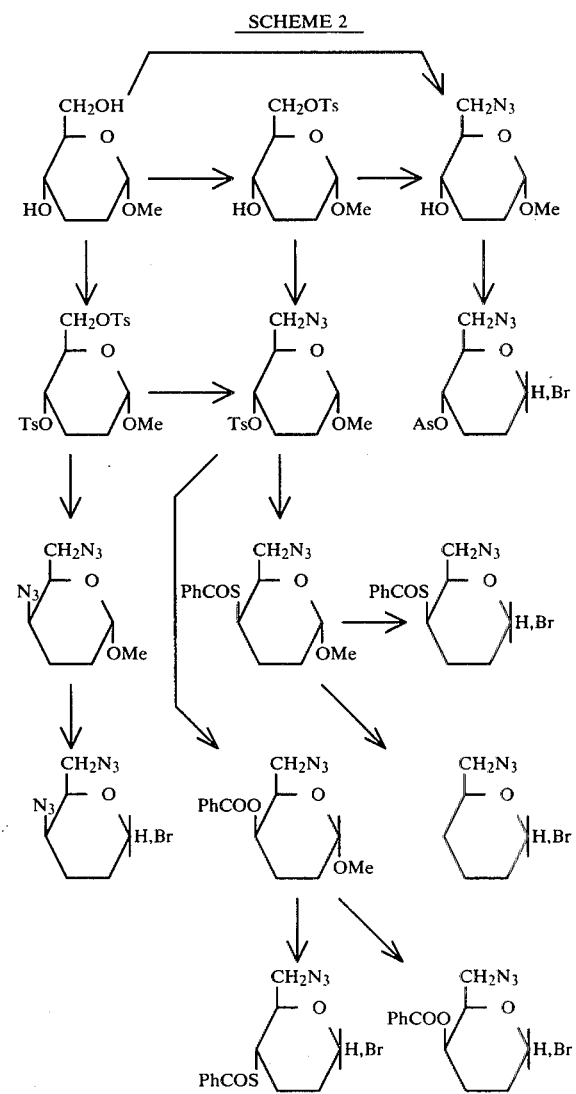

The coupling reaction for the synthesis of α-glycosides from the monocyclic intermediates can be readily achieved with excellent yields via two procedures known per se. The first one takes advantage of the reaction by which glycals can add alcohols through the catalytic action of boron trifluoride-etherate in an inert solvent of low dielectric constant, such as benzene, carbon tetrachloride or chloroform. During this type of reaction any amino functions must be protected by such groups as phthaloyl, succinyl or alkyloxy-carbonyl, e.g. to give

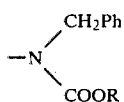

If secondary or tertiary amines, secondary amides or secondary carbamates are present, the catalyst reacts with them forming insoluble by-products and no glycoside can be isolated. The reactants should be soluble in the solvents mentioned above (benzene, CCl$_4$, CHCl$_3$). The reaction between glycals and alcohols is fast (5 to 15 minutes) and takes place at room temperature and the proportion of β-glycosides is negligible.

The second procedure is a modified Koenigs-Knorr glycosylation reaction between a glycosyl halide and an alcohol function, which takes advantage of the non-participating neighbouring group at carbon 2, adjacent to the reaction center (anomeric carbon). The catalyst used could be silver oxide or silver carbonate but preferably the mixture of mercuric cyanide and mercuric bromide or a quaternary ammonium bromide such as tetrabutyl bromide or Amberlite IR-400 (Br$^-$ form), or a sulphide (tetrahydrothiophene) and a proton acceptor such as 2,6-lutidine, mercuric cyanide, anhydrous sodium bicarbonate or Amberlite IR-400 (CN$^-$), which increases the proportion of α-glycoside obtained at the expense of the β-anomer. The formation of pseudo-trisaccharides of 2-deoxy-streptamine can be effected stepwise, by the addition of one glycosyl moiety at a time, i.e. first forming a disaccharide with a protected 2-deoxystreptamine, then reacting another glycosyl moiety with the already formed disaccharide as depicted below, where X is a halide or represents the reactive 1:2 double bond of a glycal.

SCHEME 3

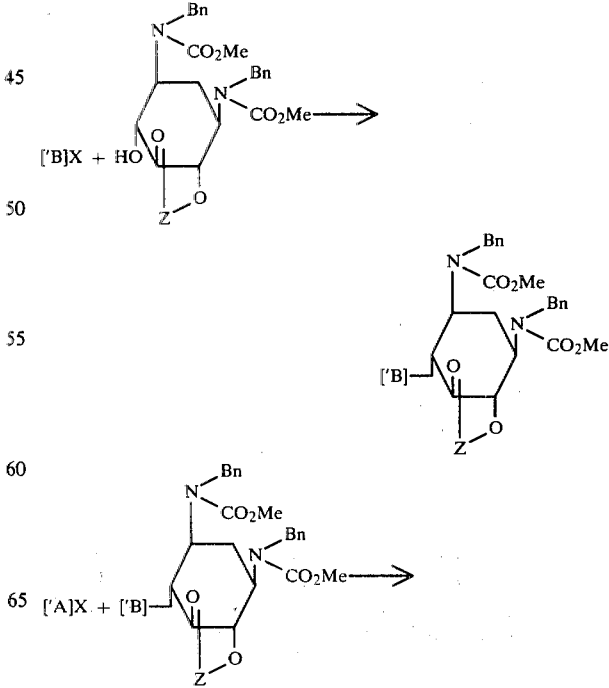

-continued
SCHEME 3

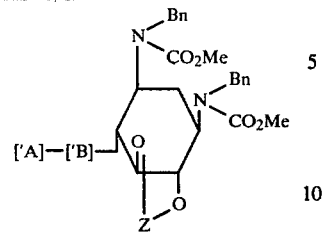

Z = cyclohexylidene or isopropylidene
['A] & ['B] are protected residues corresponding to [A] & [B] defined above.
Bn = benzyl Alternatively the trisaccharide can be synthesized by the reaction of a disaccharide derivative, [A]—[B]—X, with a suitably protected 2-deoxystreptamine (Scheme 4).

SCHEME 4

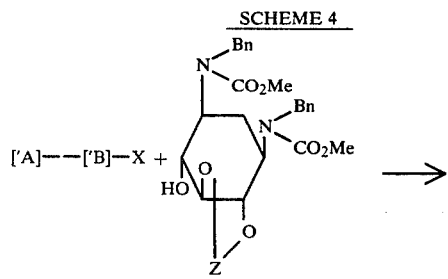

-continued
SCHEME 4

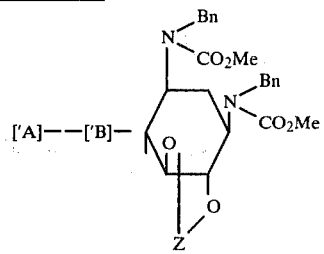

Once the protected trisaccharides have been obtained the sequences of reactions which follow are directed towards the removal of the trisaccharide protective groups, thus liberating the amino and hydroxyl functions.

Schemes 5 and 6 summarize some of the possible routes to synthesize the 4-O and 5-O-glycosides of 2-deoxystreptamine.

When the glycosylation is carried out simultaneously at carbons 4 and 6 of the aminocyclitol ring, whether the glycal or the glycosyl halide method is used, and in spite of the presence of an excess of glycosylating agent, a small percentage of the disaccharides formed remain unreacted at the end of the reaction period. Their separation, however, from the trisaccharides is easily accomplished by filtration through silica gel and elution with solvents. These disaccharides (4-O-glycoside and 6-O-glycoside of either 2-deoxystreptamine or 2,5-dideoxystreptamine) which are present to the maximum extent of 15–20% of the total reaction products, can, once separated from the trisaccharides, be glycosylated again to furnish more trisaccharides.

SCHEME 5

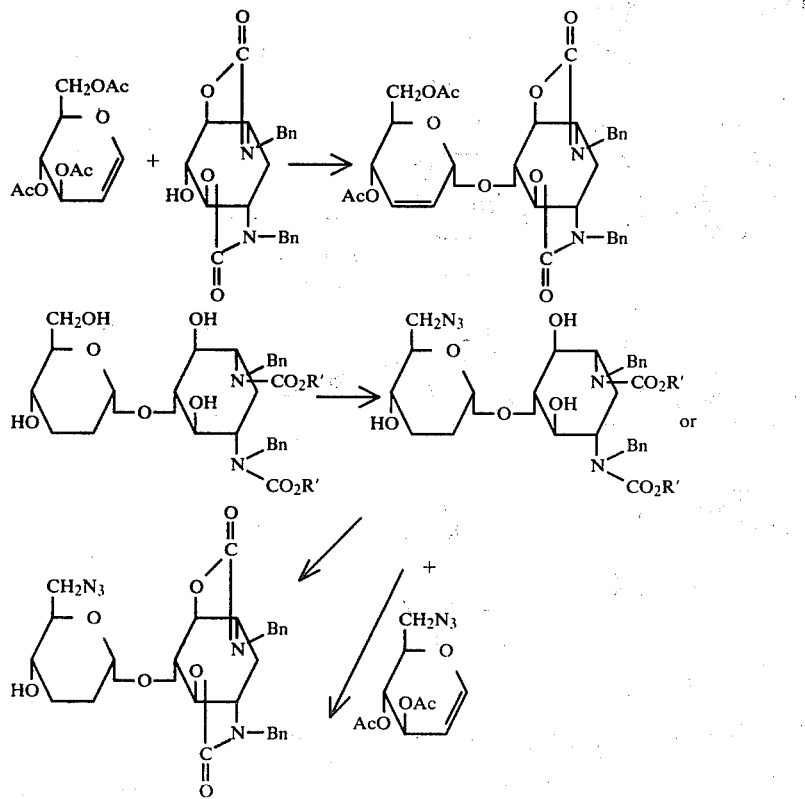

SCHEME 5
-continued
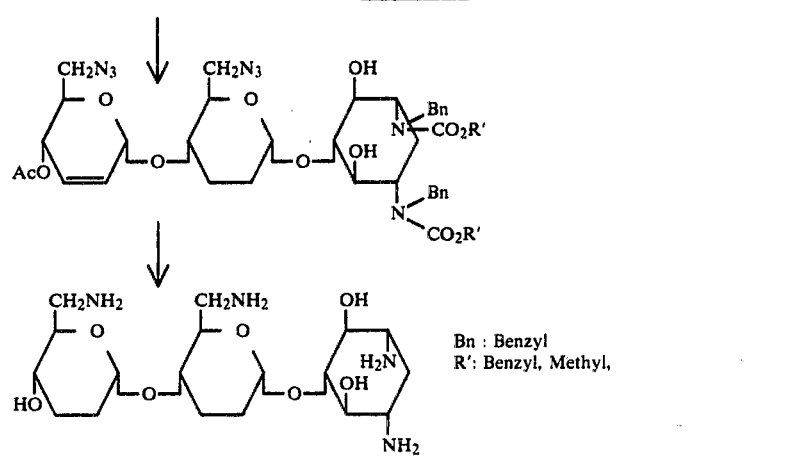
Bn : Benzyl
R' : Benzyl, Methyl,
SCHEME 6
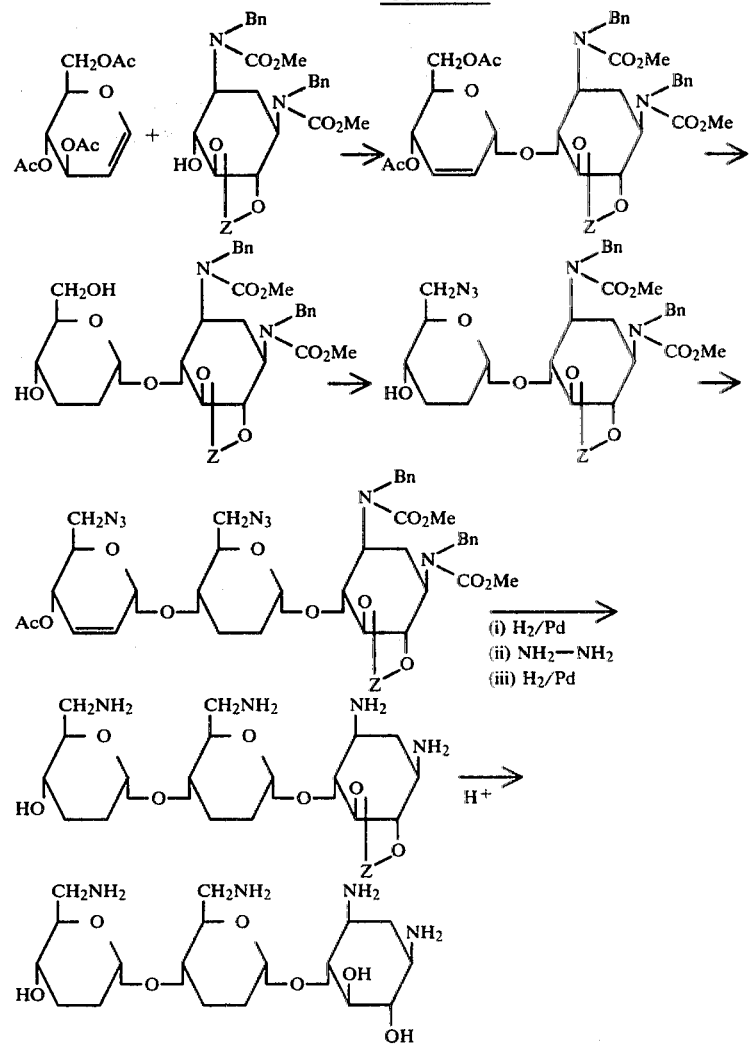
Bn : Benzyl
Z : cyclohexylidene, Isopropylidene
The fully protected trisaccharides obtained in this way are then subjected to a series of chemical operations designed to remove the protective groups, thus liberating the trisaccharide. Removal of esters, carbamates and amide functions is achieved by alkaline hydrolysis with hydroxides from the alkaline or alkaline earth metals, or, preferably, with 80–90% hydrazine hydrate in a suitable solvent such as methanol, ethanol or propanol. N- and O-benzyl groups are removed by catalytic hydrogenation over palladium-on-charcoal or Raney nickel catalysts. Any azido functions present are reduced simultaneously to amino groups during this operation.

Some of the trisaccharides included in this invention can be obtained, apart from the general method of glycosylation with the appropriate glycosyl halide or glycal, through chemical transformation of the intermediates 4,6-di-O-(2,3-dideoxy-α-D-erythro-hexopyranosyl)-2-deoxy-1,3-di-N-benzyl-1,3-di-N-methoxycarbonylstreptamine and 4,6-di-O-(2,3-dideoxy-α-D-erythro-hexopyranosyl) 1,3-di-N-benzyl-2,5-dideoxy-1,3-di-N-methoxycarbonylstreptamine. When either of these trisaccharides is reacted with carbon tetrachloride, hexamethylphosphorus triamide and sodium azide, replacement of the primary alcohol functions by the azido group at carbons 6′ and 6″ is achieved. These transformations, followed by the removal of the groups protecting the trisaccharides, lead to the obtention of 4,6-di-O-(6-amino-2,3,6-trideoxy-α-D-erythro-hexopyranosyl)-2-deoxystreptamine and 4,6-di-O-(6-amino-2,3,6-trideoxy-α-D-erythro-hexopyranosyl)-2,5-dideoxystreptamine.

An alternative route to the compounds mentioned above is embodied in the following sequence of reactions: selective tosylation of the primary alcohol functions in the partially protected trisaccharides i.e. [4,6-di-O-(2,3-dideoxy-α-D-erythro-hexopyranosyl) 1,3-di-N-benzyl 2,5-dideoxy-1,3-di-N-methoxycarbonyl streptamine (a), and 4,6-di-O-(2,3-dideoxy-α-D-erythro-hexopyranosyl)-2-deoxy-1,3-di-N-methoxycarbonyl-1-N,3-N, 5-O-tribenzylstreptamine (b)] is followed by the nucleophilic displacement of the tosyl group by sodium azide to give the 6′, 6″-diazido protected trisaccharides. These are then treated under saponification conditions in ethanol or propanol (80/90% hydrazine hydrate, sodium potassium or barium hydroxide) to remove the N-methoxycarbonyl groups, then submitted to hydrogenation (hydrogen, palladium-on-charcoal) to reduce the azido functions to amino ones with concomitant hydrogenolysis of the N-benzyl groups.

The inconvenience of this route to the azido intermediates is that during the selective tosylation step the separation of by-products is difficult, making it impossible to obtain yields greater than 60–65% of the ditosylated derivative.

In a similar fashion 4,6-di-O-[4,6-diamino-2,3,4,6-tetradeoxy-α-D-(threo or erythro)-hexopyranosyl]-2-deoxystreptamine or 4,6-di-O-[4,6-diamino-2,3,4,6-tetradeoxy-α-D-(threo or erythro)-hexopyranosyl]-2,5-dideoxystreptamine can be obtained from the above-mentioned intermediate trisaccharides (a) and (b) by permesylation of the four hydroxyl functions, displacement of the mesyl groups by azido in dimethylformamide or hexamethylphosphoric triamide, saponification of the protective groups (N—COOMe), followed by hydrogenation over palladium-on-charcoal catalyst. Schemes 7 and 8 illustrate the sequence of steps in the preparation of some of the trisaccharides of the invention.

SCHEME 7

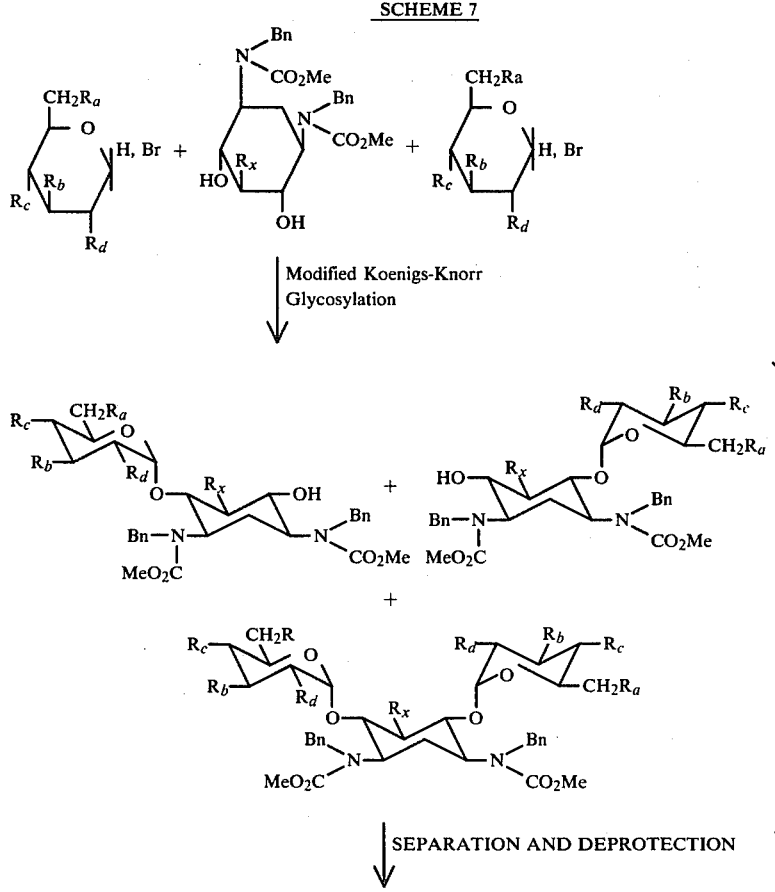

SCHEME 7
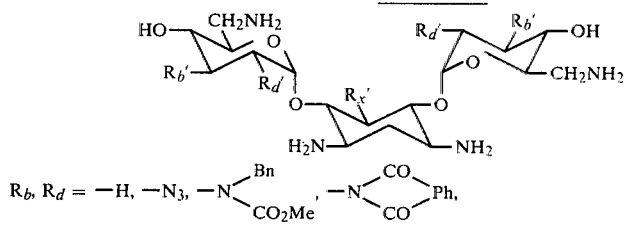
$R_b, R_d = -H, -N_3, -N(Bn)(CO_2Me), -N(CO)(CO)Ph$,
$R_c = -N_3, -OAc, -SCOPh, -H$,
$R_a = -N_3, -N(CO)(CO)Ph, -N(Bn)(CO_2Me)$
$R_x = -H, -O-CH_2-CH=CH_2, -O-BENZYL, -O-CH_2-S-CH_3$
Bn = BENZYL
$R_b', R_d' = -H, -NH_2$
$R_x' = -H, -OH$
SCHEME 8
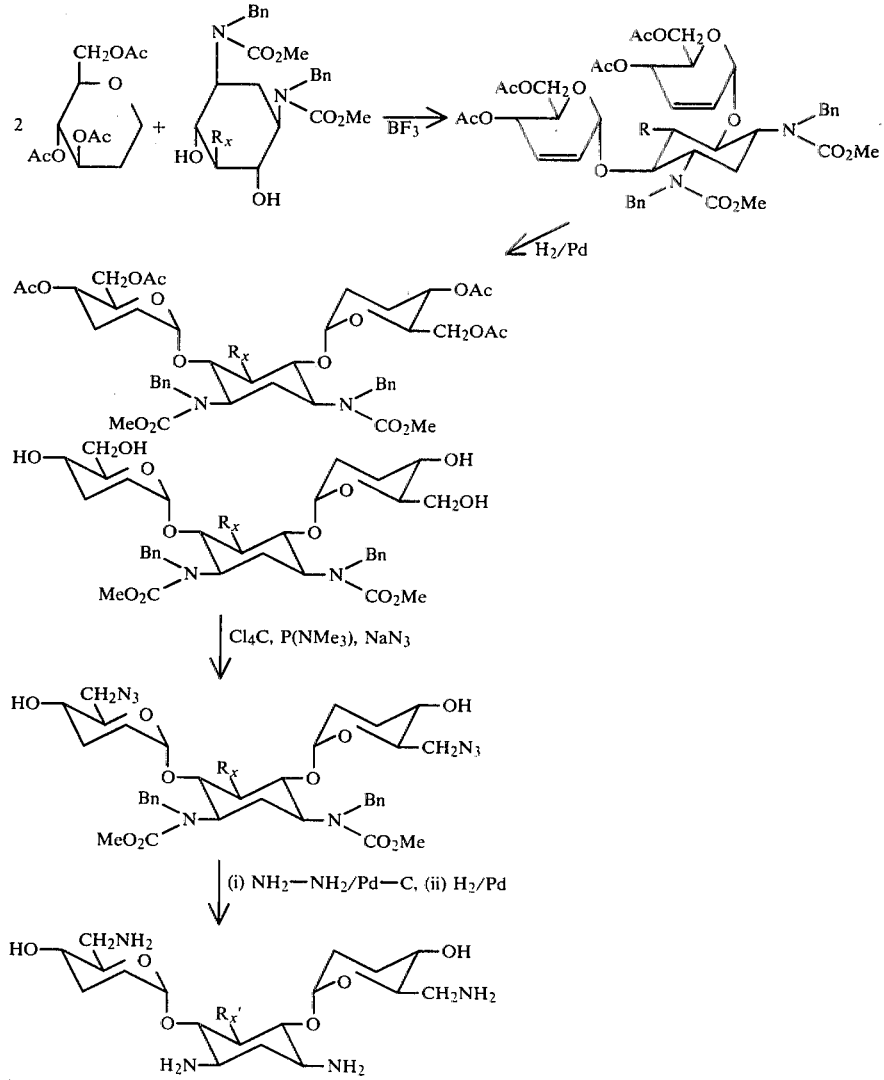
$R_x: -H, -O-ALLYL, -O-BENZYL, -O-CH_2-S-CH_3; R_x' = H, OH$

SCHEME 8

Bn: BENZYL

The pseudotrisaccharides of the invention possess excellent antibacterial activity which, in some cases, appears superior to that of Kanamycin A itself. Illustrated below is a table showing the minimal inhibitory concentrations (MIC's) of Kanamycin A together with those of one of the trisaccharides synthesized (Example I) against a variety of Gram-positive and Gram-negative bacteria as obtained by the Steers agar-dilution method with Mueller-Hinton agar medium.

TABLE 1

|  | MIC ($\mu$g/ml) | |
| --- | --- | --- |
|  | Kanamycin A | Example LI |
| *Micrococcus pyogenes aureus* 6539 P | 0.8 | 0.4 |
| *Staphylococcus pyogenes* Smith A | 0.8 | 0.4 |
| *Escherichia coli* R 1513 | 100 | 32 |
| *Salmonella tiphymurium* | 100 | 32 |
| *Proteus mirabilis* | 2 | 0.4 |
| *Pseudomonas aeruginosa* s.p. | 100 | 16 |
| *Pseudomonas aeruginosa* I.A. | 100 | 32 |
| *Salmonella sui-pestifer* | 32 | 32 |
| *Pseudomonas aeruginosa* D 15 | 25 | 8 |
| *Proteus rettgeri* | 0.4 | 0.2 |
| *Proteus morganii* | 0.8 | 0.2 |

In vitro activity of Kanamycin A and compound (Example LI). MIC's in Mueller-Hinton broth pH 7.2.

In addition the pseudotrisaccharides of the invention are less susceptible to deactivation by, and are therefore effective against, bacteria which are resistant to Kanamycin and Apramycin.

Acids from which pharmaceutically acceptable addition salts of the compounds of the invention can be prepared are those which form non-toxic addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate, saccharate and p-toluene sulphonate salts.

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavouring or colouring agents. They may be injected parenterally, for example, intramuscularly or subcutaneously. For parenteral administration, they are best used in the form of a sterile aqueous solution which may contain other solutes, for example, enough salts or glucose to make the solution isotonic.

The invention is illustrated by the following Examples of the preparation and characterisation of compounds of the invention. In these Examples, all temperatures are given in °C., the organic solutions are drried over anhydrous $Na_2SO_4$ and concentrated at 35° (10 Torr), and the PMR data follow the general practice adopted in the scientific journals. First the position in the spectrum for a particular signal or signals is given in $\delta$ (p.p.m.) with respect to the internal standard tetramethylsilane. In brackets the types of signals are given, i.e. singlet (s), doublet (d), triplet (t), multiplet (m) and this is followed by the number of protons responsibe for those signals together with the molecular position or functional group whose signals are reported.

EXAMPLE I

A solution of methyl 4,6-O-benzylidene-2,3-dideoxy-$\alpha$-D-erythro-hex-2-enopyranoside (50 g, 0.2 mol) in dry methanol (1 l.) containing 10% palladium-on-charcoal (9.0 g) was hydrogenated at 4 atm. at room temperature for 48-72 h. The catalyst was filtered off and the filtrate was concentrated in vacuo to yield syrupy methyl 2,3-dideoxy-$\alpha$-D-erythro hexopyranoside (32 g, 98%). $[\alpha]_{5461}^{22} + 155°$ (c 1.61, chloroform).

TLC : $R_f$ 0.37 (ethyl acetate - ethanol, 8:1).

PMR data (CDCl$_3$): $\delta$ 1.20 (m, 4 H, H-2,2',3,3'), 3.20 (bm, 2 H, 2-OH), 3.55 (m, 2 H, H-4,5), 3.80 (m, 2 H, H-6,6') and 4.67 (m, 1 H, H-1$\alpha$).

Analysis: Calcd. for: $C_7H_{14}O_4$. C, 51.86; H, 8.70. Found: C, 51.95; H, 8.80%.

EXAMPLE II

To a solution of methyl 2,3-dideoxy-$\alpha$-hexo-erythro-pyranoside (31 g, 0.191 mol) in dry pyridine (150 ml) toluene-p-sulphonyl chloride (36.29 g, 0.191 mol) was added and the mixture was allowed to stand at room temperature for 0.5 h. A small amount of water was then added, after which the solution was concentrated, giving a syrup which was poured into water and extracted with ether. The extracts were dried and concentrated to a small volume. After standing in the refrigerator the solution precipitated a solid which was filtered, washed with petroleum ether (40°-60°) and dried in vacuo at 45°. Recrystallization from benzene-petroleum ether (40°-60°) gave pure methyl 2,3-dideoxy-6-O-toluene-p-sulphonyl-$\alpha$-D-erythro-hexopyranoside as a colourless solid (36 g, 60%), m.p.: 100°-102°. $[\alpha]_D^{20} + 78°$ (c 1, chloroform).

TLC: $R_f$ 0.55 (ethyl acetate).

PMR data (CDCl$_3$): $\delta$ 1.75 (m, 4 H, H-2,2',3,3'), 2.43 (s, 3 H, Ph-Me), 3.27 (s, 3 H, OMe), 3.60 (m, 2 H, H-4,5), 4.27 (m, 2 H, H-6,6'), 4.60 (m, 1 H, H-1$\alpha$), 7.35 (m, 2 H, aromatic) and 7.80 (m, 2 H, aromatic).

Analysis: Calcd. for: $C_{14}H_{20}O_6S$: C, 53.16; H, 6.37; S, 10.12. Found: C, 53.26 v H, 6.57; S, 10.39%.

EXAMPLE III

Method I

A mixture of methyl 6-O-toluene-p-sulphonyl-2,3-dideoxy-$\alpha$-D-erythro-hexopyranoside (1 g, 3.16 mmol) and sodium azide (0.6 g, 9.2 mmol) in dry N,N-dimethylformamide (12 ml) was heated at 80° and stirred for 12 h. The solvent was removed in vacuo and the residue was treated with ice-water and extracted into chloroform. The extracts were washed with water, dried and evaporated to yield a syrup (0.52 g, 88%) which was purified by distillation at 100°-110°/0.1 mm. Methyl 6-azido-2,3,6-trideoxy-$\alpha$-D-erythro-hexopyranoside was obtained as a colourless oil. $[\alpha]_D^{22} + 118°$ (c 1, chloroform).

TLC: $R_f$ 0.62 (ethyl acetate).

PMR data (CDCl$_3$): δ 1.80 (m, 4 H, H-2,2′,3,3′), 2.23 (bs, 1 H, OH), 3.16 (s, 3 H, OMe), 3.50 (m, 2 H, H-6,6′), 3.60 (m, 2 H, H-4,5) and 4.70 (t, 1 H, H-1α, width 3 Hz).

Analysis: Calcd. for: C$_7$H$_{13}$N$_3$O$_3$: C, 44.91; H, 7.00; N, 22.44. Found: C, 44.66; H, 7.05; N, 22.15%.

Method II

A mixture of methyl 2,3-dideoxy-α-D-erythro-hexopyranoside (1.62 g, 10 mmol), hexamethylphosphorous triamide (1.78 g, 11 mmol), carbon tetrabromide (3.32 g, 10 mmol) and dry N,N-dimethylformamide (15 ml) was stirred at −50° for 2 h. Sodium azide (1.30 g, 20 mmol) was then added, and the mixture was stirred at 60° for 12 h, concentrated (1 Torr) and diluted with water (30 ml). The solution was extracted with chloroform and the combined extracts were washed with water and concentrated. Distillation of the syrupy residue gave methyl 6-azido-2,3,6-α-D-erythro-hexopyranoside (1.5 g, 78%), b.p. 120°/0.1 Torr. $[\alpha]_D^{22}+118°$ (c 1, chloroform).

TLC: R$_f$ 0.62 (ethyl acetate) and 0.32 (chloroform).

PMR spectra was identical with that of the product as prepared in method I.

Analysis: Calcd. for: C$_7$H$_{13}$N$_3$O$_3$: C, 44.91; H, 7.00; N, 22.44. Found: C, 44.75; H, 7.10; N, 22.30%.

EXAMPLE IV

A mixture of methyl 4-O-benzoyl-6-bromo-2,3,6-trideoxy-α-D-erythro-hexopyranoside (J.Org.Chem., 34, (1969), 3519–3522) (23.3 g) and sodium azide (10 g) in dry dimethylformamide (200 ml) was stirred at 60°–70° for 36 h. Water (200 ml) was added to the reaction mixture and it was extracted with dichloromethane (3×100 ml). The combined extracts were washed with water, dried and evaporated to yield pure syrupy 6-azido-4-O-benzoyl-2,3,6-trideoxy-α-D-erythro-hexopyranoside (18.7 g, 91%). $[\alpha]_{5461}^{24}+151.7°$, $[\alpha]_D^{24}+114°$ (c 0.3, ethanol).

TLC: R$_f$ 0.58 (dichloromethane).

This was subjected to de-O-benzoylation in dry methanol (250 ml) with sodium methoxide (200 mg) as catalyst for 12 h. The reaction mixture was neutralized with Amberlite IR-120 (H+) resin, filtered and evaporated. Methyl benzoate was removed from the syrupy residue by repeated extraction with petroleum ether. The colourless syrup methyl 6-azido-2,3,6-trideoxy-α-D-erythro-hexopyranoside which resulted (5.80 g, 48%) had an R$_f$ 0.62 in TLC (ethyl acetate).

Analysis: Calcd. for: C$_7$H$_{13}$N$_3$O$_3$: C, 44.91; H, 7.00; N, 22.44. Found: C, 44,70; H, 6,80; N, 22.31%.

EXAMPLE V

A solution of methyl 6-azido-2,3,6-trideoxy-α-D-erythro-hexopyranoside (1 g) in 0.1 M hydrochloric acid (20 ml) was heated at 100° for 0.5 h, then cooled and neutralized with Amberlite IR-400 (carbonate form) resin. Filtration and evaporation of the reaction mixture yielded a syrup (0.9 g, 97%) which was purified by chromatography on silica-gel using chloroform-ethanol (93:7) as eluant. 6-Azido-2,3,6-trideoxy-D-erythro-hexose was obtained as a colourless syrup (TLC, R$_f$ 0.06 (chloroform - ethanol, 93:7), which gave a positive Fehling test. $[\alpha]_{5461}^{25}+56°$, $[\alpha]_D^{25}+41°$ (c 0.6, water).

Analysis: Calcd. for: C$_6$H$_{11}$N$_3$O$_3$: C, 41.61; H, 6.40; N, 24.26. Found: C, 41.75; H, 6.29; N, 24.35%.

EXAMPLE VI

6-Azido-2,3,6-trideoxy-D-erythro-hexose (1.73 g, 10 mmol) was acetylated in acetic anhydride (8 ml) with a few drops of 70% perchloric acid as catalyst. After 1 h at room temperature the solution was saturated with dry hydrogen bromide and the mixture was allowed to stand for 2 h. It was then poured into ice-water and extracted with ice-water, ice-cold saturated sodium bicarbonate solution and water. Finally the extracts were dried (Na$_2$SO$_4$) and concentrated to yield 4-O-acetyl-6-azido-2,3,6-trideoxy-D-erythro-hexopyranosyl bromide as a colourless syrup (2.2 g), which was used immediately for the next step.

Analysis: Calc. for: C$_8$H$_{12}$N$_3$O$_3$Br: C, 34.55; H, 4.35; N, 15.11; Br, 28.7. Found: C, 34.20; H, 4.65; N, 14.92; Br, 29.0.

EXAMPLE VII

4-O-Acetyl-6-azido-2,3,6-trideoxy-D-erythro-hexopyranosyl bromide (2.78 g, 10 mmol) in dry nitromethane (30 ml), mercuric cyanide (0.5 g), silver carbonate (3 g), methanol (1 ml) and Drierite (5 g) was shaken in the dark at room temperature for 48 h. The mixture was filtered and the solids were washed with dichloromethane. The combined organic liquids were washed with water, dried and evaporated to dryness to give a syrup (2.1 g, 91.7%). Examination of the syrup by TLC (ethyl acetate) showed a main component, R$_f$ 0.65, which was separated by chromatography on silica gel using benzene-ethyl acetate as eluant. The yield of methyl 4-O-acetyl-6-azido-2,3,6-trideoxy-α-D-erythro-hexopyranoside was 1.37 g, 60%. $[\alpha]_D^{22}+122°$, $[\alpha]_{5461}^{20}+165°$ (c 1, chloroform).

PMR data (CDCl$_3$): δ 1.84 (m, 4 H, H-2,2′,3,3′), 2.02 (s, 3 H, OAc), 3.30 (m, 2 H, H-6,6′), 3.38 (s, 3 H, -OMe), 3.86 (q, 1 H, J$_{4,5}$=9, J$_{5,6}$=J$_{5,6'}$=5 Hz, H-5), 4.60 (m, 1 H, H-4), 4.69 (t, 1 H, H-1α, with 4 Hz).

Analysis: Calcd. for: C$_9$H$_{15}$N$_3$O$_4$: C, 47.15; H, 6.60; N, 18.33. Found: C, 47.07; H, 6.75; N, 18.50%.

EXAMPLE VIII

6-Azido-2,3,6-trideoxy-α-D-erythro-hexopyranoside (1.5 g, 8 mmol) in dry methanol (100 ml) was hydrogenated over 10% palladium-on-charcoal (0.4 g) at room temperature under a pressure of 2.5 atm. for 5 h. The catalyst was removed and the solution evaporated to give a colourless syrup (1.2 g), which showed a positive ninhydrin reaction. This syrup in methanol (3 ml) was treated with ethereal hydrogen chloride solution whereupon a crystalline hydrochloride precipitated immediately. This was filtered, washed with ether and recrystallized from methanol-ether to yield pure methyl 6-amino-2,3,6-trideoxy-α-D-erythro-hexopyranoside hydrochloride (1.25 g, 79%). M.p.: 153°–154° dec. $[\alpha]_{5461}^{22}+130°$, $[\alpha]_D^{22}+96.3$ (c 1, water).

TLC: R$_f$ 0.65 (chloroform-methanol-ammonia, 20:6:1).

PMR data (D$_2$O): δ 1.80 (m, 4 H, H-2,2′,3,3′), 3.10 (m, 2 H, H-6,6′), 3.38 (s, 3 H, OMe), 3.5–3.9 (m, 2 H, H-4,5) and 4.80 (m, 1 H, H-1α).

Analysis: Calcd. for: C$_7$H$_{16}$NO$_3$Cl: C, 42.53; H, 8.15; N, 7.08; Cl, 17.93. Found: C, 42.68; H, 8.04; N, 7.00; Cl, 18.20%.

EXAMPLE IX

Methyl 6-azido-2,3,6-trideoxy-α-D-erythro-hexopyranoside (3.0 g, 16 mmol) in methanol (100 ml) containing acetic anhydride (2 ml) was hydrogenated over 10% palladium-on-charcoal (0.4 g) at room temperature under a pressure of 2.5 atms. for 5 h. The catalyst was filtered off and the filtrate was evaporated to dryness giving a syrupy residue which crystallized upon treatement with ether to yield 3.18 g, 98%. The product was recrystallized from chloroform-ether to give pure methyl 6-acetamido-2,3,6-trideoxy-α-D-erythro-hexopyranoside. M.p.: 117°–118°. [α]$_{5461}^{21}$ –13° (c 1, chloroform).

TLC: R$_f$ 0.82 (chloroform-methanol-ammonia, 20:6:1).

PMR data (CDCl$_3$): δ 1.8 (m, 4 H, H-2,2',3,3'), 2.04 (s, 3 H, -NAc), 3.06 (dq, 2 H, J$_{6,6'}$=14 Hz, J$_{5,6}$=3.0 Hz, J$_{5,6'}$=3.5 Hz, H-6,6'), 3.29 (s, 3 H, OMe), 3.51 (dt, 1 H, J$_{4,5}$=9.0 Hz, H-5), 3.98 (dq, 1 H, J$_{3,4}$=3.0 Hz, J$_{3',4}$=12 Hz, H-4), 4.4 (bs, 1 H, OH), 4.63 (t, 1 H, width 5 Hz, H-1) and 6.50 (bs, 1 H, NH).

Analysis: Calcd. for: C$_9$H$_{17}$NO$_4$: C, 53.18; H, 8.43; N, 6.89. Found: C, 53.12; H, 8.56; N, 7.01%.

EXAMPLE X

Methyl 6-acetamido-2,3,6-trideoxy-α-D-erythro-hexopyranoside (1.5 g) in 0.1 M aqueous hydrochloric acid (30 ml) was heated at 100° for 0.5 h. The solution was neutralized with Amberlite IR-400 (carbonate form) resin and evaporated in vacuo to yield a syrup, 1.46 g. This syrup showed the presence of two compounds by TLC (ether-methanol, 9:1): (a) R$_f$ 0.08 and (b) R$_f$ 0.05. The separation of these two components was achieved by chromatography in a silica-gel column using mixtures of ether-methanol as eluants. Compound (a), 6-acetamido-2,3,6-trideoxy-D-erythro hexopyranose (R$_f$ 0.08) was obtained as a colourless syrup (0.75 g, 50%) which reduced Fehling's reagent. [α]$_{5461}^{25}$ +50°, [α]$_D^{25}$ +36° (c 0.5, water).

Analysis: Calcd. for C$_8$H$_{15}$NO$_4$: C, 50.78; H, 7.99; N. 7.40. Found: C, 50.89; H, 8.10; N, 7.10%.

The chromatographic fractions from the previous preparation containing compound (b), R$_f$ 0.05, were pooled and evaporated to yield a syrup (negative test with Fehling's reagent) which crystallized on standing. Pure 6-acetamido-1,6-anhydro-2,3,6-trideoxy-β-D-erythro-hexopyranose was obtained (0.16 g, 12%) as a colourless crystalline solid. M.p.: 125°–126°. [α]$_{5461}^{24}$ –32° (c 0.5, water).

PMR data (CDCl$_3$): δ1.82 (bm, 4 H, H-2,2',3,3'), 2.04 and 2.07 (2 s, 3 H, —NAc, two rotational isomers), 2.91 (s, 1 H, OH), 3.51 (m, 3 H, H-5,6,6'), 4.52 (unresolved multiplet, 1 H, width 10 Hz, H-4), 5.44 and 5.7 (2 s broad, 1 H, width 4 Hz, ratio 7:9, H-1 of two rotational isomers).

Mass spectrum: M/e 171 (calculated for C$_8$H$_{13}$NO$_3$: M+171).

Analysis: Calcd. for: C$_8$H$_{13}$NO$_3$: C, 56.12; H, 7.65; N, 8.18. Found: C, 56.11; H, 7.92; N, 7.93.

EXAMPLE XI

6-Acedamido-2,3,6-trideoxy-D-erythro-hexopyranose (1.89 g, 10 mmol) was treated with acetic anhydride-acetic acid, 2:1 (10 ml) and 70% perchloric acid (0.2 ml) for 2 hours after which the solution was saturated at 0° with dry hydrogen bromide. The mixture was allowed to stand for 2 h, then poured into ice-water and extracted with dichloromethane (4×50 ml). The extracts were successively washed with ice water (2×50 ml), cold aqueous NaHCO$_3$, water (2×50 ml), and finally they were dried (Na$_2$SO$_4$) and evaporated. The syrupy residue, 6-acetamido-4-O-acetyl-2,3,6-trideoxy-D-erythro-hexopyranosyl bromide (2.64 g, 90%) was pure enough for further reactions but it decomposes on standing at room temperature.

Analysis: Calcd. for: C$_{10}$H$_{16}$NO$_3$Br: C, 40.83; H, 5.48; N, 4.76; Br, 27.16. Found: C, 40.95; H, 5.88; N, 4.80; Br, 26.80%.

EXAMPLE XII

A mixture of 6-acetamido-4-O-acetyl-2,3,6-trideoxy-D-erythro hexopyranosyl bromide (1.47 g, 5 mmol), mercuric cyanide (2.5 g), mercuric bromide (3 g), methanol (1.0 ml), Drierite (5 g) and dry nitromethane (20 ml) was shaken in the dark at room temperature for 48 h. The mixture was filtered and the solids were washed with dichloromethane. The combined organic liqids were washed with water, dried and evaporated to dryness to furnish a syrup (1.16 g, 95%). Examination of this syrup by TLC (chloroform-acetone, 3:1) showed a main compound (R$_f$ 0.60) which was separated from the crude reaction product by column chromatography on silica gel using chloroform-ethyl acetate mixture as eluant. The crystalline product, methyl 6-acetamido-4-O-acetyl-2,3,6-trideoxy-D-α-erythro-hexopyranoside, was recrystallized from ether-hexane (yield: 0.80 g, 65%). M.p. 97°–98°. [α]$_{5461}^{20}$ +135°, [α]$_D^0$ +98° (c 0.5, chloroform).

PMR data (CDCl$_3$): δ1.82 (bm, 4 H, H-2,2',3,3'), 1.96 and 2.04 (2 S, 6 H, —NAc and —OAc), 3.52 (s, 3 H, —OMe), 3.58 (bm. 3 H, H-5,6,6'), 4.52 (m, 1 H, H-4), 4.64 (t, 1 H, width 4 Hz, H-1α) and 5.82 (bs, 1 H, —NH).

Analysis: Calcd. for: C$_{11}$H$_{19}$NO$_5$: C, 53.86; H, 7.81; N, 5.71. Found: C, 54.05; H, 7.98; N, 5.52%.

EXAMPLE XIII

Methyl 2,3-dideoxy-α-D-erythro-hexopyranoside (6 g, 37 mmol) in dry pyridine (50 ml) was treated with toluene-p-sulphonyl chloride (15.2 g, 80 mmol) at 0° with stirring. The reaction mixture was stored at 22° for 12 h, and after the addition of water (1 ml) it was concentrated. The syrupy residue was poured into ice-water, the oil which separated was extracted with CHCl$_3$, and the extracts were washed with water, dried and evaporated. The solid thus obtained (12 g, 70%) was recrystallized from methanol to give pure methyl 2,3-dideoxy-4,6-di-O-toluene-p-sulphonyl-α-D-erythro-hexopyranoside. M.p.: 110°–111.5°. [α]$_D^{22}$ +80.8° (c 1, chloroform).

TLC: R$_f$ 0.62 (benzene-ethyl acetate, 9:4).

PMR data (CDCl$_3$): δ 1.5–2.1 (m, 4 H, H-2,2',3,3'), 2.45 (s, 6 H, 2 CH$_3$—Ph—), 3.2 (s, 3 H, —OMe), 3.70–4.40 (m, 4 H, H-4,5,6,6'), 4.55 (t, 1 H, H-1α), 7.55 (q, 8 H, —Ph—).

Analysis: Calcd. for: C$_{21}$H$_{26}$O$_8$S$_2$: C, 53.60; H, 5.57; S, 13.62. Found: C, 53.98; H, 5.59; S, 13.8%.

EXAMPLE XIV

A cooled solution (0°) of methyl 6-azido-2,3,6-trideoxy-α-D-erythro-hexopyranoside (3 g, 16 mmol) in dry pyridine (10 ml) was treated dropwise with methanesulphonyl chloride (2.29 g, 20 mmol) with stirring for 1 h. Water (1 ml) was then added to the reaction mixture and the solvents were removed in vacuo at 30°. The residual syrup was poured into ice-water producing a precipitate which was filtered, washed with water and dried. The solid was recrystallized from benzene-petroleum ether (40°–60°) to give methyl 6-azido-4-O-methanesulphonyl-2,3,6-trideoxy-α-D-erythro-hexopyranoside (3.5 g, 83%) as a colourless solid. M.p.: 54°–56°. [α]$_D^{22}$ +142° (c, 1, chloroform).

TLC: R$_f$ 0.55 (chlofororm).

PMR data (CDCl$_3$): δ 1.70–2.30 (m, 4 H, H-2,2′,3,3′), 3.05 (s, 3 H, —SO$_2$Me), 3.40 (s, 3 H, —OMe), 3.45 (d, 2 H, H-6,6′), 3.75–4.0 (m, 1 H, H-5), 4.40–4.60 (m, 1 H, H-4), 4.70 (t, 1 H, H-1α).

Analysis: Calcd. for: C$_8$H$_{15}$N$_3$O$_5$S: C, 36.22; H, 5.70; N, 15.84; S, 12.08. Found: C, 36.06; H, 5.75; N, 15.89; S, 11.77

EXAMPLE XV

A mixture of methyl 2,3-dideoxy-4,6-di-O-toluene-p-sulphonyl-α-D-erythro-hexopyranoside (5 g, 10.6 mmol), sodium azide (10 g, 0.16 mol) and dimethylformamide (50 ml) was stirred and heated at 100° for 24 h. The solvent was evaporated in vacuo and the residue was partitioned between water-ether (1:1, 200 ml). The aqueous layer was extracted with ether and the combined organic liquors were washed with water, dried and evaporated to give a syrup which was distilled at 110°–120°/1 Torr. Methyl 4,6-di-azido-2,3,4,6-tetradeoxy-α-D-threo-hexopyranoside (1.9 g, 90%) was obtained as a colourless oil. [α]$_D^{21}$+15.3° (c 2, chloroform).

TLC: R$_f$ 0.7 (benzene-ethyl acetate, 9:4).

PMR data (CDCl$_3$): δ 1.5–2.20 (m, 4 H, H-2,2′,3,3′), 3.0–3.30 (m, 2 H, H-6,6′), 3.40 (s, 3 H, OMe), 3.50 (m, 1 H, H-4), 4.85–5.05 (m, 1 H, H-5), 5.75 (t, 1 H, H-1α).

Analysis: Calcd. for C$_7$H$_{12}$N$_6$O$_2$: C, 39.62; H, 5.70; N, 39.60. Found: C, 39.75; H, 5.87; N, 39.30%.

EXAMPLE XVI

A mixture of methyl 6-azido-4-O-methanesulphonyl-2,3,6-trideoxy-α-D-erythro-hexopyranoside (2.65 g, 10 mmol), sodium azide (5 g, 80 mmol) and dimethylformamide (30 ml) was heated at 100° for 24 h. The solvent was removed in vacuo and the residue was partitioned between ether-water (1:1, 100 ml). The aqueous layer was extracted with ether and the combined organic liquids were washed with water, dried and evaporated. The syrup thus obtained was purified by distillation at 110°–120°/1 Torr. Yield: 1.80 g, 85% of methyl 4,6-di-azido-2,3,4,6-tetradeoxy-α-D-threo-hexopyranoside as a colourless oil. [α]$_D^{21}$+15.3° (c 1, chloroform)

TLC: R$_f$ 0.7 (benzene-ethyl acetate 9:4).

Analysis: Calcd. for C$_7$H$_{12}$N$_6$O$_2$: C, 39.62; H, 6.70; N, 39.60. Found: C, 39.51; ; H, 5.72; N, 39.76%.

EXAMPLE XVII

Methyl 4,6-di-azido-2,3,4,6-tetradeoxy-α-D-threo-hexopyranoside (1.9 g, 8.9 mmol) in methanol (30 ml) was hydrogenated over 10% palladium-on-charcoal catalyst ) 0.2 g) under a pressure of 4 atms. for 3 h. The catalyst was removed and the filtrate was evaporated in vacuo to yield a syrup (1.35 g, 95%). The syrup was dissolved in methanol (3 ml) and a solution of oxalic acid in dry ether was added until precipitation was complete. The solid was filtered, washed with dry ether and dried in vacuo. It was recrystallized from water-isopropanol to yield 2 g (90%) of methyl 4,6-di-amino-2,3,4,6-tetradeoxy-α-D-threo-hexopyranoside-dihydrogen dioxalate as a colourless solid. M.p.: 250° decomposition. [α]$_D^{25}$+55.3° (c 1, water).

TLC: R$_f$ 0.2 (chloroform-methanol-ammonium hydroxide, 100:30:3).

PMR data (CDCl$_3$): δ 1.6–2.3 (m, 4 H, H-2,2′,3,3′), 2.8–3.30 (m, 2 H, H-6,6′), 3.40 (s, 3 H, —OMe), 3.60 (m, 1 H, H-4), 4.20–4.40 (m, 1 H, H-5), 4.90 (m, 1 H, H-1α).

Analysis: Calcd. for: C$_{11}$H$_{20}$N$_2$O$_{10}$: C, 38.82; H, 5.92; N, 8.23. Found: C, 38.79; H, 5.88; N, 8.35%.

EXAMPLE XVIII

A mixture of potassium thiobenzoate (1.87 g, 10 mmol), methyl 6-azido-4-O-methanesulphonyl-2,3,6-trideoxy-α-D-erythro-hexopyranoside (1.5 g, 5.6 mmol) and dry dimethylformamide (40 ml) was stirred and heated at 100° for 5 h under nitrogen. The solvent was then removed in vacuo and the residue was partitioned between water-ether (1:2, 100 ml). The ethereal layer was separated and the aqueous phase was extracted with ether (2×25 ml). The combined ethereal liquors were washed with water (2×25 ml), dried and concentrated in vacuo to give a syrup which was purified by chromatography on silica gel using mixtures of benzene-chloroform as eluant. Methyl 6-azido-4-S-benzoyl-2,3,4,6-tetradeoxy-4-thio-α-D-threo-hexopyranoside (1.32 g, 80%) was a syrup presenting a single spot in TLC (chloroform) R$_f$ 0.75. [α]$_D^{22}$+91.3° (c 1, chloroform).

PMR data (CDCl$_3$): δ 1.7–2.60 (m, 4 H, H-2,2′,3,3′), 3–3.60 (m, 2 H, H-6,6′), 3.40 (s, 3 H, OMe), 4.05 (m, 1 H, H-4), 4.30 (m, 1 H, H-5), 4.80 (dt, 1 H, H-1α), 7.80 (m, 5 H, —Ph).

Analysis: Calcd. for: C$_{13}$H$_{17}$N$_3$O$_3$S: C, 52.86; H, 5.80; N, 14.22; S, 10.85. Found: C, 53.01; H, 5.90; N, 24.40; S, 10.72.

EXAMPLE XIX

Methyl 6-azido-4-S-benzoyl-2,3,4,6-tetradeoxy-4-thio-α-D-threo-hexopyranoside (0.3 g, 1 mmol) in dry methanol (10 ml) was treated with sodium (20 mg) in methanol (2 ml) and the mixture was stored for 12 h at 22°. It was then neutralized with CO$_2$ and concentrated. The residue was extracted with chloroform and the extracts, upon concentration, gave a syrup (0.18 g, 90%) which was purified by preparative TLC (benzene-ethyl acetate, 4:1). A clear syrup of pure bis (methyl 6-azido-2,3,4,6-tetra-deoxy-4-thio-α-D-threo-hexopyranoside) bisulphide was obtained by aerial oxidation of its thiol precursor. [α]$_D^{23}$−46.2° (c 0.8, methanol).

TLC: R$_f$ 0.3 (benzene-chloroform, 3:1), R$_f$ 0.65 (benzene-ethyl acetate, 4:1).

IR $\nu_{max}^{CHCl_3}$ 2100 (N$_3$) cm$^{-1}$.

PMR data (CDCl$_3$): δ 1.26–2.30 (m, 4 H, H-2,2′,3,3′), 2.94 (d, 1 H, H-4), 3.38 (s, 3 H, OMe), 3.14–3.70 (m, 2 H, H-6,6′), 4.16 (m 1 H, H-5), 4.73(d, 1 H, H-1α).

Analysis: Calcd. for: C$_{14}$H$_{24}$N$_6$O$_4$S$_2$: C, 41.56; H, 5.98; N, 20.77; S, 15.83. Found: C, 41.70; H, 6.03; N, 20.91; S, 15.60.

EXAMPLE XX

A mixture of methyl 6-azido-4-S-benzoyl-2,3,4,6-tetradeoxy-4-thio-α-D-threo-hexapyranoside (0.72 g, 3.5 mmol), acetone-deactivated Raney nickel (5 g) and alcohol (20 ml) was stirred at room temperature for 5 H. The catalyst was removed and the filtrate was concentrated to give an oil which was purified by distillation at 70°–80°/1 Torr. Yield: 0.36 g (85%) of pure methyl 6-azido-2,3,4,6-tetradeoxy-α-D-glycero-hexopyranoside as a colourless oil.

Analysis: Calc. for: C$_7$H$_{13}$N$_3$O$_2$: C, 49.11; H, 7.65; N, 24.524. Found: C, 49.30; H, 7.78; N, 24.38%.

EXAMPLE XXI

A mixture of methyl 6-azido-4-S-benzoyl-2,3,4,6-tetradeoxy-4-thio-α-D-threo-hexopyranoside (0.2 g, 0.65 mmol) and partially deactivated Raney nickel (10 g) in ethanol (20 ml) was stirred at 22° for 12 h and then filtered. The solids were washed with ethanol and th organic solution was concentrated to give a syrup which was purified by silica gel column chromatography (eluant: chloroform). A clear syrup of pure methyl 6-benzamido-2,3,4,6-tetradeoxy-α-D-glycero-hexopyranoside was obtained. $[\alpha]_D^{23}+72.2°$ (c 1.7, methanol).

TLC: $R_f$ 0.55 (chloroform-ethyl acetate, 1:1), $R_f$ 0.25 (chloroform).

IR $\nu_{max}^{CHCl_3}$ 3330 (NH), 2940, 1650 (NCOPh), 1605 (Ph), 1585, 1545 (Amide II) cm$^{-1}$.

PMR data (CDCl$_3$, 110°): δ 1.30–2.52 (m, 6H, H-2,2′,3,3′,4′), 3.33 and 3.42 (2s, 6H, 2 OMe), 3.57 (m, 2 H, H-6,6′), 4.80 (m, 1 H, H-5), 5.76 (m, 1H, H-1α), 6.70 (b. band, 1 H, —NHCO), 7.45 and 7.80 (2 sets of multiplets, 5 H, —Ph).

Analysis: Calcd. for: C$_{14}$H$_{19}$NO$_3$: C, 67.44; H, 7.68; N, 5.62. Found: C, 67.68; H, 7.40; N, 5.41%.

EXAMPLE XXII

A mixture of methyl 6-azido-4-O-mesyl-2,3,6-trideoxy-α-D-erythro-hexopyranoside (0.265 g, 1 mol) and anhydrous sodium benzoate (0.72 g, 5mmol) in hot N,N-dimethylformamide (35 ml) was heated at 110° for 4 h, then poured into ice-water. Extraction of the mixture with ether, followed by washing of the organic phase with water and concentration of the dried extracts gave a syrup (0.25 g, 89%) which was purified by silica gel chromatography using benzene-chloroform mixtures as eluant. Pure methyl 6-azido-4-O-benzoyl-2,3,6-trideoxy-α-D-threo-hexopyranoside was obtained as a syrup, b.p.: 120°–140°/0.1 Torr. $[\alpha]_D^{21}+68°$ (c 0.4, chloroform).

IR $\nu_{max}^{CHCl_3}$ 2100 (N$_3$), 1710 (OCOPh), 1600 (ph), cm$^{-1}$.

PMR data (CDCl$_3$): δ 1.75(m, 4 H, H-2,2′,3,3′), 3.52 (m, 2 H, H-6,6′) 3.45 (s, 3 H, OMe), 4.12 (m, 1 H, H-5), 4.86 (s, 1 H, H-1α), 5.13 (s, 1 H, H-4), 7.50 and 8.08 (2 m, total intensity 5 H, —Ph).

Analysis: Calcd. for: C$_{16}$H$_{21}$NO$_6$: C, 55.91; H, 6.14; N, 15.05. Found: C, 56.00; H, 6.06; N, 14.85%.

EXAMPLE XXIII

A mixture of methyl 4-O-mesyl-6-N-methoxycarbonyl-2,3,6-trideoxy-α-D-erythro-hexopyranoside (0.16 g, 0.6 mmol) and anhydrous sodium benzoate (0.72g, 5 mmol) in hot N,N-dimethylformamide (15 ml) was heated at 110° for 4 h. The solution was poured into ice-water and extracted with ether. The organic layer was washed with water, dried and concentrated to give a syrup which was purified by silica gel column chromatography using benzene-chloroform mixtures as eluant.

Pure, syrupy methyl 4-O-benzoyl-6-N-methoxycarbonyl-2,3,6-trideoxy-α-D-threo-hexopyranoside (0.13 g, 0.66 g) had the following analytical characteristics: $[\alpha]_D^{21}+32°$ (c 0.23, chloroform).

TLC: $R_f$ 0.5 (chloroform -ethyl acetate, 1:1).

IR $\nu_{max}^{CHCl_3}$ 3100 (NH), 2930, 1710 ; (OCOPh), 1690 (NCOOMe), 1600 (Ph), 1520 cm$^{-1}$ (Amide II).

PMR data (CDCl$_3$): δ 1.76 (m, 4 H, H-2,2′,3,3′), 3.39 (s, 3 H, OMe) 3.61 (s, 3 H, NCOOMe), 4.04 (m, 1 H, H-5), 4.83(s, 1 H, H-1α), 5.20 (bm, 2 H, H-4 and NH), 7.50 and 8.09 (2m, 5 H total intensity, —Ph).

Analysis: Calcd. for C$_{16}$H$_{21}$NO$_6$: C, 59.43; H, 6.55; N, 4.33. Found: C, 59.20; H, 6.40; N, 4.21%.

EXAMPLE XXIV 5,6-O-cyclohexylidene-tetra-N-methoxycarbonylneamine (S. Umezawa et al., Bull. Chem. Soc. Japan, 46, 3507, 1973) (15 g, 23.7 mmol) in tetrahydrofuran (100 ml) was treated with a solution of sodium metaperiodate. The solution was concentrated, the residue was extracted with hot chloroform, and the combined extracts were washed with water, dried and concentrated. The residue (15 g) was recrystallized from water-ethanol to give the pure dialdehyde: 5,6-O-cyclohexylidene-2-deoxy-4-O{(1R, 2R)-1-[(1R)-1-formyl-2-(methoxycarbonylaminoethoxy)]-2-formyl-2-(methoxycarbonylamino)ethyl}-1,3-bis-N-methoxycarbonylstreptamine (13.2 g, 88%), M.p.: 127°–133°, $[\alpha]_D^{20}-4°$ (c 0.57, N, N-dimethylformamide).

TLC: $R_f$ 0.60 (ethyl acetate - ethanol, 8:1), $R_f$ 0.3 (ethyl acetate).

IR $\nu_{max}^{Nujol}$ 3290 (broad NH,OH), 1710 (—CHO), 1695 (NCOOMe), 1530 cm$^{-1}$ (Amide II).

PMR data (methylsulphoxide-d$_6$): δ 1.55 (bm, 12 H, H-2,2 and cyclohexylidene protons), 3.52 (m, 12 H, 4 NCOOMe), 5.62 (m, 1 H, H-1′α), 6.80–7.50 (4 H, NH), 8.30 and 9.12 (2s, 1.5, CHO).

Analysis: Calcd. for: C$_{26}$H$_{40}$N$_4$O$_{14}$.0.5H$_2$O; C, 48.66; H, 6.44; N, 8.73. Found: C, 48.75; H, 6.53; N, 8.60%.

The product isolated in the previous step described above (2g, 3.1 mmol) in methanol (30 ml) was treated with NaOMe (0.2 g) at 22° for 24 h. Sodium borohydride (0.3 g) in water (10 ml) was added and the mixture was stored at 22° for 12 h. The solution was concentrated to dryness and the residue was extracted with acetone. Concentration of the extracts left a solid which was purified by silica gel column chromatography using chloroform-ethyl acetate-1% triethylamine as eluant. The isolated product was recrystallized from ethyl acetate to give 0.38 g (34%) of pure 5,6-O-cyclohexylidene-2-deoxy-1,3-di-N-methoxycarbonylstreptamine. M.p.: 109°–111°. $[\alpha]_D^{23}+14°$ (c 1, chloroform); +10° (c 1, methanol).

IR $\nu_{max}^{Nujol}$ 3390 (OH), 3260 (NH), 1690 (NCOOMe), 1550 cm$^{-1}$ (Amide II).

PMR data (methylsulphoxide-d$_6$): δ 1.48 (bm, 12 H, H-2,2 and cyclohexylidene protons), 3.52 (s, 6 H, 2 NCOOMe), 5.14 (m, 1 H, OH), 7.38 (b.band, 2 H, 2 NH).

Analysis:
Calcd. for C$_{16}$H$_{26}$N$_2$O$_7$: C, 53.62; H, 7.31; N, 7.81. Found: C, 53.52; H, 7.20; N, 7.53%.

EXAMPLE XXV

A mixture of 5,6-O-cyclohexylidene-2-deoxy-di-N-methoxycarbonylstreptamine (0.3 g) in pyridine (3 ml) and acetic anhydride (0.5 ml) was stored at 22° for 10 h. It was then concentrated to a small volume and poured into ice-water. The oily material was extracted with chloroform and the extracts were washed with saturated NaHCO$_3$ solution and water, then dried. On evaporation they gave a solid (0.31 g, 93%) which was crystallized from ethyl acetate-petroleum ether 40°–60° to give pure 4-O-acetyl-5,6-O-cyclohexylidene-2-deoxy-1,3-di-N-methoxycarbonylstreptamine, m.p.: 164°–166°. $[\alpha]_D^{23}-4.6°$ (c 1.2, chloroform).

TLC: $R_f$ 0.5 (ethyl acetate).

PMR data (CDCl$_3$): δ 1.43 (bm, 12 H, 10-cyclohexylidene protons and H-2,2), 2.10 (s, 3 H, -OAc), 2.65 (bm, 2 H, H-1,3), 3.63 and 3.68 (2s, 6 6 H, 2NCOOMe), 4.85–6.40 (bm, 3 H, H-4 and 2 NH).

Analysis: Calcd. for: $C_{18}H_{28}N_2O_8$: C, 53.99; H, 7.05; N, 6.99. Found: C, 54.01; H, 6.97; N, 6.52%.

EXAMPLE XXVI

A mixture of the dialdehyde obtained in the first part of Example XXIV (16 g, 25.2 mmol), ethanol (250 ml) and triethylamine (25 ml) was stirred at 22° for 24 h, then concentrated. A solution of the syrupy residue in water (150 ml) was treated with a solution of NaBH$_4$(2g) in water (20 ml) for 12 h. The mixture was concentrated, the solid residue was extracted with chloroform (3×30 ml) and the extracts were washed with water, dried and concentrated. The residue was acetylated with acetic anhydride (5ml) and pyridine (50 ml) for 24 h, and the solid obtained after concentration of the mixture was eluted from silica gel with ethyl acetate to give 4.84 g, (48%) of 4-O-acetyl-5,6-O-cyclohexylidene-2-deoxy-1,3-di-N-methoxycarbonylstreptamine. M.p.: 164°–166°. $[\alpha]_D^{23} -5°$ (c 1.2, chloroform).

TLC: R$_f$ 0.5 (ethyl acetate); R$_f$ 0.3 (chloroform-ethyl acetate, 1:1).

The IR and PMR spectra of this product were identical with those of the compound isolated in Example XXV.

EXAMPLE XXVII

A solution of 4-O-acetyl-5,6-O-cyclohexylidene-2-deoxy-1,3-di-N-methoxycarbonylstreptamine (0.2 g, 0.05 mmol) in methanol (4ml) was stirred with a solution of Ba(OH)$_2$.8H$_2$O (0.6 g) in water (3 ml) at 80° for 24 h, then neutralized with CO$_2$ and centrifuged. The supernatant was concentrated to dryness, the residue was extracted with methanol and the filtered extracts were concentrated to a syrup which was eluted from Amberlite CG 50 (NH$_4^+$) resin with 0.1–0.2 N aqueous methanolic ammonia (1:1). Evaporation of the eluates gave a syrup which was dissolved in water (0.5 ) and neutralized with 0.5 N H$_2$SO$_4$. The sulphate of 5,6-O-cyclohexylidene-2-deoxystreptamine was was obtained by precipitation with dioxan (83 mg, 48%). M.p.: 212° (decomp.). $[\alpha]_D^{20} -9°$ (c. 0.57, water).

TLC: R$_f$ 0.4 (chloroform-methanol-conc.ammonia, 100:30:3), R$_f$ 0.65 (methanol - conc.ammonia, 8:1).

Analysis: Calcd. for: $C_{12}H_{22}N_2O_3 \cdot H_2SO_4$: C, 42.34; H, 7.10; N, 8.23. Found: C, 42.45; H, 7.20; N, 8.17%.

EXAMPLE XXVIII

Sodium hydride (60% oil dispersed, 0.16 g, 6.2 mmol, 23% excess) was added gradually, with stirring, to a solution of 5,6-O-cyclohexylidene-2-deoxy-1,3-di-N-methoxycarbonylstreptamine (0.62 g, 1.7 mmol) in N,N-dimethylformamide acooled at 0°–5°. After 1 h, benzyl bromide (1 g, 6.7 mmol, 20% excess) was added with vigorous stirring. The reaction was stored at 25° for 24 h, after which pyridine (3 ml) was added and the mixture was stored for a further hour. Concentration of the solution in vacuo (1 Torr) left a syrup which was poured into ice-water and extracted with chloroform. The extracts were washed with water, dried, concentrated and azeotroped with toluene to give a syrup which was fractionated by silica gel column chromatography using benzene and chloroform as eluants. Among other components separated, compound (a): 5,6-O-cyclohexylidene-2-deoxy-1,3-di-N-methoxycarbonyl-1N, 3-N, 4-O-tribenzylstreptamine was isolated in 18% yield. M.p.: 80°–87°, $[\alpha]_D^{22} -°$ (c 1, chloroform).

TLC: R$_f$ 0.4 (benzene-ethyl acetate, 9:1).

IR: $\nu_{max}^{CHCl_3}$ 1695 (NCOOMe), 1600 (Ph), 1500 (benzyl) cm$^{-1}$.

PMR data (CDCl$_3$, 80°): δ 1.56 (bm, 11 H, H-2ax and 10 cyclohexylidene protons), 3.56 and 3.64 (2 s, 6 H, 2-NCOOMe), 7.19 and 1.27 (2 s, 15 H, 3 Ph).

Analysis: Calcd. for: $C_{37}H_{44}N_2O_7$: C, 70.70; H, 7.00; N, 4.45. Found: C, 70.53; H, 7.14; N, 4.56%.

EXAMPLE XXIX

Another component (compound b), was isolated from the chromatographic fractionation carried out in Example XXVIII.

The yield of compound (b): 5,6-O-cyclohexylidene-2-deoxy-1,3-di-N-benzyl-1-N-methoxycarbonylstreptamine-3:4 carbamate, was 50%. M.p.: 100°–103°. $[\alpha]_D^{22} -35°$ (c 1, chloroform).

TLC: R$_f$ 0.3 (benzene-ethyl acetate, 9:1).

IR: $\nu_{max}^{CHCl_3}$ 1760 (NCOO cyclic), 1690 (NCOOMe), 1605 (Ph), cm$^{-1}$.

PMR data (CDCl$_3$): δ 1.58 (bm, 12 H, H -2,2 and 10 cyclohexylidene protons), 3.72 (s, 3 H, NCOOMe), 7.25 (m, 10 H, 2 Ph).

Analysis: Calcd. for: $C_{29}H_{34}N_2O_6$: C, 68.75; H, 6.76; N, 5.52. Found: C, 69.00; H, 7.03; N, 5.25%.

EXAMPLE XXX

Method I.

A solution of 5,6-O-cyclohexylidene-2-deoxy-1,3-di-N-benzyl-1-N-methoxycarbonylstreptamine-3:4-carbamate (0.15 g, 0.3 mmol) in dry methanol (15 ml) was treated at 70° for 2 h with sodium methoxide (20 mg). The mixture was neutralized with CO$_2$ and concentrated. The residue was then extracted with chloroform and the extracts were concentrated to give 5,6-O-cyclohexylidene 2-deoxy-1,3-di-N-benzyl-1,3-di-N-methoxycarbonylstreptamine (0.13 g, 81%). M.p.: 130°–132.5° (from ether). $[\alpha]_D^{22} -9.5°$ (c 1, chloroform).

IR: $\nu_{max}^{CHCl_3}$ 3520 (OH), 1695 (NCOOMe), 1605 (ph) cm$^{-1}$.

PMR data (CDCl$_3$): δ 1.55 (bm, 12 H, H-2,2 and 10 cyclohexylidene protons), 2.54 (s, 1 H, OH), 3.66 and 3.69 (2 s, 6 H, 2 NCOOMe), 4.42 (m, 4 H, 2 CH$_2$ Ph), 7.23 (m, 10 H, 2 Ph).

Analysis: Calcd. for $C_{30}H_{38}N_2O_7$: C, 66.89; H, 7.11; N, 5.20. Found: C, 66.70; H, 7.10; N, 5.20%.

Method II

A solution of 5,6-O-cyclohexylidene-2-deoxy-1,3-di-N-methoxycarbonyl-1-N, 3-N, 4-O-tribenzylstreptamine (0.314 g, 0.5 mmol) in methanol (15 ml) was hydrogenated over 10% palladium-on-charcoal catalyst (50 mg) at 3 atmos., 20° for 10 h. The catalyst was filtered and washed with methanol and the combined organic liquids were concentrated to give a solid which was recrystallized from ether, 5,6-O-cyclohexylidene-2-deoxy-1,3-di-N-benzyl-1,3'-di-N-methoxycarbonylstreptamine. Yield: 95% (0.26 g). M.p.: 130°–132.5°. $[\alpha]_D^{22} -9.50$ (c 1, chloroform).

The chromatographic mobilities of this compound, as well as the IR and PMR spectra, were identical with those of the compound described under Method I. No depression of the melting point occurred when both products were mixed.

Analysis: Calcd. for: $C_{30}H_{38}N_2O_7$: C, 66.89; H, 7.11; N, 5.20. Found: C, 66.92; H, 7.03; N, 5.35%.

EXAMPLE XXXI

Kanamycin sulphate (20 g) in water (100 ml) was basified with 20% NaOH solution to pH 12. Benzaldehyde (15 ml) was added and the mixture was shaken for 3 h. The precipitated solid was filtered, washed with water, dried and dissolved in methanol (100 ml). Chloroform (100 ml) and benzaldehyde (7 ml) were added to the solution and the mixture was stirred for b 12 h., concentrated to a small volume and poured into ether (100 ml). The resulting solid was washed with ether and water and dried in vacuo to give tetra-N-benzylidenekanamycin (26 g), m.p. 205°–206°.

This material was dissolved in ethanol (700 ml) and treated with sodium borohydride (5 g) in water (25 ml). The mixture was stirred for 12 h, filtered and concentrated. The glassy residue, thus obtained, (36 g) was dissolved in 6N hydrochloric acid (500 ml) and the solution was heated on a water-bath (90°) for 1 h. The filtered solution was concentrated to a syrup, treated with methanolic HCl and evaporated, this operation being repeated several times to remove boric acid. The residue was finally treated with methanol and the inorganic salts were filtered off. The solution, upon concentration, and storing at 0°, deposited pure 2-deoxy-1,3-di-N-benzylstreptamine dihydrochloride (8.33 g). M.p.: 258°–260°.

TLC: $R_f$ 0.45 (chloroform-methanol-ammonia, 100:30:5).

PMR data (D$_2$O): δ 2.05 (t, 1 H, H-2ax), 2.60 (m, 1 H, H-2eq), 3.35 (m, 2 H, H-1,3), 3.75 (m, 3 H, H-4,5,6), 4.43 (m, 4 H, 2 C$\underline{H}_2$—Ph), 7.57 (m, 10 H, 2 Ph).

Analysis: Calc. for C$_{20}$H$_{28}$N$_2$O$_3$Cl$_2$: C, 57.83; H, 5.79; N, 6.74; Cl. 17.07. Found: C, 57.90; H, 5.84; N, 6.55; Cl. 16.93.

EXAMPLE XXXII

A mixture of 2-deoxy-1,3-di-N-benzylstreptamine dihydrochloride (5 g, 12 mmol) and sodium carbonate (5 g) in water (250 ml) and acetone (50 ml) was treated dropwise with methyl chloroformate (3 ml, 39 mmol) in acetone (100 ml) at 0° for 3 h, and stored at 5° for 12 h. It was then concentrated and the residue was extracted with chloroform. The extracts were concentrated to give a syrup which was recrystallized from chloroform-ether. 2-Deoxy-1,3-di-N-benzyl-1,3-di-N-methoxycarbonylstreptamine was obtained in 86.7% yield (5.18 g), with m.p. 176°–180°. TLC: $R_f$ 0.76 (chloro - methanol - ammonia, 100:30:5).

Analysis: Calcd. for C$_{24}$H$_{30}$N$_2$O$_7$: C, 62.86; H, 6.59; N, 6.11. Found: C, 62.98; H, 6.72; N, 6.04%.

EXAMPLE XXXIII

A mixture of 2-deoxy-1,3-di-N-benzyl-1,3-di-N-methoxycarbonylstreptamine (2 g, 4.3 mmol), dry N,N-dimethylformamide (60 ml), anhydrous toluene-p-sulphonic acid (0.1 g) and 1,1-dimethoxycyclohexane (3 ml) was stirred at 100° for 2 h. An addition of 1,1-dimethoxycyclohexane (1 mol) was followed by further stirring and heating for 1.5 h, after which the mixture was neutralized with solid sodium bicarbonate (0.8 g) and concentrated to a syrup. This was extracted into chloroform, the extracts were washed with water, dried and concentrated to give a solid (2 g, 86%) which was recrystallized ten times successively from ether. 5,6-O-Cyclohexylidene-2-deoxy-1,3-di-N-benzyl-1,3-di-N-methoxycarbonylstreptamine (0.4 g) was obtained, with an optical purity of 79%. M.p.: 129°–131°. $[\alpha]_D^{21}$ −7.5° (c 2, chloroform).

TLC: $R_f$ 0.55 (benzene-ethyl acetate, 1:1); $R_f$ 0.5 (chloroform-ethyl acetate, 3:1).

IR: $\nu_{max}^{CHCl_3}$ 3520 (OH), 2940, 1695 (NCOOMe), 1605 (Ph) cm$^{-1}$.

PMR data (CDCl$_3$): δ 1.55 (bm, 12 H, H-2,2 and 10 cyclohexylidene protons), 2.54 (s, 1 H, OH), 3.66 and 3.69 (2 s, 6 H, 2 NCOOMe), 4.42 (m, 4 H, 2 CH$_2$ Ph), 7.23 (m, 10 H, 2 Ph).

Analysis: Calcd. for C$_{30}$H$_{38}$N$_2$O$_7$: C, 66.89; H, 7.11; N, 5.20. Found: C, 66.94; H, 6.96; N, 5.04%.

Upon concentration of the mother liquors from the previous preparation, the residue was recrystallized six times and 4,5-O-cyclohexylidene-2-deoxy-1,3-di-N-benzyl-1,3-di-N-methoxycarbonylstreptamine (0.3 g) was obtained with an optical purity of 63%, $[\alpha]_D^{21}$ +6° (c 1, chloroform).

TLC: $R_f$ 0.55 (benzene-ethyl acetate, 1:1); $R_f$ 0.5 (chloromethyl acetate, 3:1).

The IR and PMR spectra were identical with those of the isomer isolated above.

Analysis: Calcd. for C$_{30}$H$_{38}$N$_2$O$_7$: C, 69.89; H, 7.11; N, 5.20. Found: C, 69,68; H, 7.01; N, 5.06%.

EXAMPLE XXXIV

A solution of 5,6-O-cyclohexylidene-2-deoxy-1,3-di-N-methoxycarbonyl-1-N, 3-N, 4-O-tribenzylstreptamine (0.628 g, 1 mmol), in 50% aqueous acetic acid was heated at 80° for 20 minutes and concentrated in vacuo. The residue was azeotroped with benzene, dissolved in 2,2-dimethoxypropane (4 ml) containing toluene-p-sulphonic acid (50 mg), and heated at 70° for 5 h. After neutralization of the mixture with triethylamine (1 ml) and concentration, a syrup was obtained which was extracted into chloroform. The extracts were washed with water, dried and concentrated and the residue, dissolved in methanol (10 ml) was hydrogenated aver 5% palladium-on-charcoal (0.1 g) at 1 atmos. for 6 h. The filtered reaction mixture was concentrated and the solid, upon recrystallization from aqueous ethanol, gave pure 2-deoxy-1,3-di-N-benzyl-1,3-di-N-methoxycarbonyl-5,6-O-isopropylidenestreptamine (0.35 g, 70%), m.p. 137°. $[\alpha]_D^{23}$ −10° (c 1, chloroform).

TLC: $R_f$ 0.57 (ethyl acetate).

PMR data (CDCl$_3$): δ 1.15 (m, 1 H, H-2ax), 1.35 (s, 6 H, 2 Me, isopropylidene), 1.75 (m, 1 H, H-2eq), 2.55 (b band, 1 H, OH), 3.30 (m, 4 H, H-1,3,4,5), 3.68 (2 s, 6 H, 2 NCOOMe), 4.27 (m, 1 H, H-6), 4.48 (m, 4 H, 2 - CH$_2$ Ph), 7.23 (m, 10 H, 2 Ph).

Analysis: Calcd. for C$_{27}$H$_{34}$N$_2$O$_7$: C, 65.04; H, 6.87; N, 5.61. Found: C, 65.18; H, 6.99; N, 5.74%.

EXAMPLE XXXV

A mixture of 2-deoxy-1,3-di-N-benzylstreptamine (10 g, 24 mmol), anhydrous Na$_2$CO$_3$ (15 g) in 50% aqueous acetone (500 ml) was treated with benzyl chloroformate for 0.5 h at 0° with vigorous stirring, which was continued for a further 3 h. The mixture was concentrated to a small volume and extracted with chloroform. Concentration of the extracts gave a syrup of 2-deoxy-1,3-di-N-benzyl-1,3-di-N-benzyloxycarbonylstreptamine (11.2 g. 85%) [TLC: $R_f$ 0.17 (ethyl acetate).].

This syrup (4 g, 7.4 mmol) was dissolved in dry N,N-dimethylformamide (60 ml) containing toluene-p-sulphonic acid (0.15 g) and 1,1-dimethoxycyclohexane (6 ml). The mixture was stirred and heated at 100° for 2 h, then neutralized with solid NaHCO$_3$ (1 g) and concentrated (1 Torr) to a syrup. This was extracted into ether, and the extracts, after being washed with water and dried, were concentrated to give a solid. Recrystallization of this from benzene gave the racemic mixture containing 5,6-O- and 4,5-O-cyclohexylidene-2-1,3-di-N-benzyl-1,3-di-N-benzyloxycarbonylstreptamine (4.15 g, 88%), m.p.: 147°–150°.

TLC: $R_f$ 0.35 (chloroform), $R_f$ 0.45 (chloroform-ethyl acetate, 15:1).

IR: $\nu_{max}^{CHCl_3}$ 3430 (OH), 1690 (NCOOCH$_2$), 1600 (Ph), 1585 (Ph) cm$^{-1}$. PMR data (CDCl$_3$, 80°): δ 1.55 (m, 12 H, H-2ax, 2eq and 10 cyclohexylidene protons), 2.15 (broad, 1 H, OH), 4.40 (m, 4 H, 2-O-C$\underline{H_2}$ Ph), 5.12 (s, 4 H, 2 NC$\underline{H_2}$ Ph), 7.23 (m, 20 H, 4 Ph).

Analysis: Calcd. for C$_{40}$H$_{46}$N$_2$O$_7$: C, 72.04; H, 6.95; N, 4.15. Found: C, 71.82; H, 7.07; N, 4.20%.

EXAMPLE XXXVI

A solution of methyl 6-azido-2,3,6-trideoxy-α-D-erythro-hexopyranoside (0.187 g, 1 mmol) and 6-azido-6-deoxys-3,4-di-O-acetyl-D-glucal (0.255 g, 1 mmol) in dry benzene (18 ml) was treated with boron trifluoride etherate (0.05 ml) and stirred at 20° for 0.5 h. Triethylamine(1 ml) was added and the stirring was continued for a further 25 minutes. The reaction mixture was washed with water, dried and concentrated to give a syrup (0.325 g, 85%) which, after purification by silica gel column chromatography using benzene as eluant, gave pure syrupy methyl 4-O-(4-O-acetyl-6-azido-2,3,6-trideoxy-α-D-erythro-hex-2-eno-pyranosyl)-6-azido-2,3,6-trideoxy-α-D-erythro-hexopyranoside. $[\alpha]_D^{23}+81°$ (c 0.28 chloroform).

TLC: $R_f$ 0.4 (benzene-ethyl acetate, 10:1); $R_f$ 0.25 (benzene-chloroform, 1:1).

IR $\nu_{max}^{CHCl_3}$ 2100 (N$_3$), 1735 (OAc) cm$^{-1}$.

PMR data (CDCl$_3$): δ 1.75 (m, 4 H, H-2,2,3,3), 2.09 (s, 3 H, OAc), 3.39 (s, 3 H, OMe), 3.42 (bm, 4 H, H-6,6,6',6'), 3.80 (m, 3 H, H-4,5,5'), 4.73 (s, 1 H, H-1α), 5.21 (s, 1 H, H-1'α), 5.30 (m, 1 H, H-4'), 5.78 (m, 1 H, H-3'), 5.85 (m, 1 H, H-2').

Analysis: Calcd. for: C$_{15}$H$_{22}$N$_6$O$_6$: C, 47.11; H, 5.80; N, 21.98. Found: C, 47.03; H, 5.94; N, 22.10%.

EXAMPLE XXXVII

A mixture of 5,6-O-cyclohexylidene-2-deoxy-1,3-di-N-benzyl-1,3-di-N-methoxycarbonylstreptamine (1.03 g, 1.91 mmol), tri-O-acetyl-O-glucal (0.8 g, 2.9 mmol) and dry benzene (20 ml), was treated with boron trifluoride etherate (0.03 ml) and stirred at 20° for 0.5 h. Triethylamine (1 ml) was added and the stirring was continued for a further 20 minutes. The reaction mixture was washed with water, dried and hydrogenated over 10% palladium-on-charcoal (20 mg) at 2 atmos. for 3 h. After filtering the suspension, and washing the catalyst with methanol, the combined organic liquids were concentrated to give a glassy product (1.53 g, 85%). This product dissolved in methanol (20 ml) was catalytically deacetylated with sodium methoxide (20 mg) for 12 h at 22°. Neutralization of the mixture with CO$_2$ was followed by concentration to give a syrup which was extracted into chloroform. The extracts, once filtered, were concentrated to a solid residue which was purified by silica gel column chromatography using chloroform-ethyl acetate as eluant. 4-O-(2,3-dideoxy-α-D-erythro-hexopyranosyl)-5,6-O-cyclohexylidene-2-deoxy-1,3-di-N-benzyl-1,3-di-N-methoxycarbonylstreptamine was obtained (1.35 g) as a crystalline product. M.P.: 153°–159°. $[\alpha]_D^{23}+42.7°$ (c 1, chloroform).

IR: $\nu_{max}^{CHCl_3}$ 3450 (OH), 1690 (NCOOMe), 1605 (Ph) cm$^{-1}$.

PMR data (CDCl$_3$, 80°): δ 1.15–2.00 (bm, 16 H, H-2,2,2',2',3',3' and 10 cyclohexylidene protons), 2.21 (b. band, 2 H, 20 H), 3.65 and 3.66 2 s, 6 H, 2 NCOOMe), 5.24 (m, 1 H, H-1'α), 7.20 (m, 10 H, 2 Ph).

Analysis: Calcd. for: C$_{36}$H$_{48}$N$_2$O$_{10}$: C, 64.65; H, 7.23; N, 4.18. Found: C, 64.62; H, 7.35; N, 4.15%.

EXAMPLE XXXVIII

A mixture of 5,6-O-cyclohexylidene-2-deoxy-1,3-di-N-benzyl-1,3-di-N-methoxycarbonylstreptamine (0.306 g, 0.57 mmol), tri-O-acatyl-D-glucal (0.24 g, 0.9 mmol) and dry benzene (10 ml) was treated with boron trifluoride etherate (0.03 ml) and stirred at 20° for 0.5 h. Triethylamine (1 ml) was added and the stirring continued for a further 20 minutes. The reaction mixture was washed with water, dried and concentrated to give a glassy product. This was catalytically deacetylated in methanol (10 ml) with sodium methoxide (15 mg) at 22° for 12 h. Neutralization of the mixture with CO$_2$ was followed by concentration to give a syrup which was extracted with chloroform. The extracts, washed with water, dried and concentrated, gave a residue which was eluted from silica gel with benzene-chloroform mixtures. 4-O-(2,3-Dideoxy-α-D-erythro-hex-2-enopyranosyl)-5,6-O-cyclohexylidene-2-deoxy-1,3-di-N-benzyl-1,3-di-N-methoxycarbonylstreptamine (0.4 g, 95%) was obtained as a colourless solid, M.p.: 114°–118°. $[\alpha]_D^{23}+36°$ (c 0.86, methanol).

TLC: $R_f$ 0.3 (chloroform - ethyl acetate, 1:1); $R_f$ 0.55 (ethyl acetate).

IR: $\nu_{max}^{CHCl_3}$ 3440 (OH), 1695 (NCOOMe), 1605 (Ph), 1590 (Ph) cm$^{-1}$. PMR data (CDCl$_3$): δ 1.56 (m, 12 H, H-2ax, 2eq and 10 cyclohexylidene protons), 2.88 (b. band, 2 H, 2 OH), 3.66 (bs, 6 H, 2 NCOOMe), 5.42 (m, 1 H, H-1'α), 5.89 (m, 2 H, H-2',3'), 7.25 (m, 10 H, 2 Ph).

Analysis: Calcd. for C$_{36}$H$_{46}$N$_2$O$_{10}$: C, 64.84; H, 6.95; N, 4.20. Found: C, 64.98; H, 7.04; N, 4.15%.

EXAMPLE XXXIX

A benzenic solution (25 ml) of 4,5-O-cyclohexylidene-2-deoxy-1,3-di-N-benzyl-1,3-di-N-methoxycarbonylstreptamine (0.5 g, 0.92 mmol) and tri-O-acetyl-D-glucal (0.4 g, 1.5 mmol) was treated; with boron trifluoride etherate (0.06 ml) and stirred for 0.5 h at 22°. Triethylamine (1 ml) was added and after 20 minutes stirring period, the mixture was washed with water, hydrogenated over 10% palladium-on-charcoal (70 mg) at 2 atmos. for 3 h. The catalyst was filtered and washed with methanol, the combined organic liquids were concentrated to give a glassy residue (0.76 g, 85%). This was deacetylated with sodium methoxide (20 mg) in methanol (25 ml) for 12 h at 22°. Neutralization (CO$_2$) and concentration left a residue which was extracted into chloroform. The extracts were filtered and concentrated, and the solid thus obtained was purified by silica gel column chromatography using benzene-chloroform mixtures as eluant. The crystalline solid obtained, 6-O-(2,3-dideoxy-2-D-erythro-hexopyranosyl)-4,5-O-cyclohexylidene-2-deoxy-1,3-di-N-benzyl-1,3-di-N-methoxycarbonylstreptamine (0.447 g, 72%) had m.p.: 121°–125°. $[\alpha]_D^{21}+36.7°$ (c 0.7, chloroform). TLC: $R_f$ 0.65 (chloroform-ethyl acetate, 1:1).

IR: $\nu_{max}^{CHCl_3}$ 3480 (OH), 1695 (NCOOMe), 1600 (Ph) cm$^{-1}$. PMR data (CDCl$_3$, 80°), δ 1.55 (bm, 16 H, H-2,2,2',2',3',3' and 10 cyclohexylidene protons), 2.25

(bm, 2 H, 20 H), 3.66 (m, 6 H, 2 NCOOMe), 5.32 (m, 1 H, H-1'α), 7.20 (m, 10 H, 2 Ph).

Analysis:

Calcd. for: $C_{36}H_{48}N_2O_{10}$; C, 64.65; H, 7.23; N, 4.18. Found: C, 64.71; H, 7.20; N, 4.07%.

EXAMPLE XL

A mixture of 5,6-O-cyclohexylidene-2-deoxy-1,3-di-N-benzyl-1,3-di-N-methoxycarbonylstreptamine (0.5 g, 0.92 mmol) and tri-O-acetyl-D-glucal (0.4 g, 1.5 mmol) was treated with boron trifluoride etherate (0.06 ml) and stirred for 0.5 h at 22°. The reaction mixture was processed as in Example XXXIX, except for the deacetylation procedure which was not carried out in this Example. The crude syrupy residue was chromatographed on silica gel. Elution with benzene-chloroform mixtures gave a solid which was recrystallized from ethanol-petroleum or ether-petroleum to give pure 4-O-(4,6-di-O-acetyl-2,3-dideoxy-α-D-erythro-hexopyranosyl) 5,6-O-cyclohexylidene-2-deoxy-1,3-di-N-benzyl-1,3-di-N-methoxycarbonylstreptamine, m.p.: 70°–75°. $[\alpha]_D^{23}+51°$ (c 1, chloroform).

TLC: $R_f$ 0.55 (chloroform-ethyl acetate, 5:1).

IR: $\nu_{max}^{CHCl_3}$ 1730 (OAc); 1690 (NCOOMe).

PMR data (CDCl₃, 95°): δ 1.26–1.89 (bm, 16 H, H-2,2,2',2',3',3' and 10 cyclohexylidene protons), 1.96 and 1.99 (2 s, 6 H, 2 OAc), 3.63 and 3.65 (2 s, 6 H, 2 NCOOMe), 5.27 (m, 1 H, H-1'α), 7.15 (m, 10 H, 2 Ph).

Analysis: Calcd. for: $C_{40}H_{52}N_2O_{12}$: C, 63.82; H, 6.91; N, 3.72. Found: C, 63.51; H, 7.16; N, 3.48%.

EXAMPLE XLI

Method I.

A mixture of 2-deoxy-1,3-di-N-benzyl-1,3-di-N-methoxycarbonyl-5,6-O-isopropylidenestreptamine (0.4 g, 0.8 mmol), tri-O-acetyl-D-glucal (0.24 g, 0.9 mmol) and dry benzene (10 ml) was treated with boron trifluoride etherate (0.02 ml) with stirring, at 22°, for 0.5 h. It was neutralized with triethylamine (1 ml), washed with water and hydrogenated over 10% palladium-on-charcoal (50 mg) at 2 atmos. for 3 h. The catalyst was filtered and washed with methanol, the combined organic liquids were concentrated and the residue was dissolved in chloroform (10 ml) containing toluene-p-sulphonic acid (20 mg) and methanol (2 ml). The mixture was heated at 55°–60 °for 2 h, neutralized with triethylamine (0.5 ml) and concentrated to dryness. The residue, after extraction with chloroform, was purified by silica gel column chromatography using chloroform-ethyl acetate mixtures as eluant. The yield of pure syrupy 4-O-(4,6-di-O-acetyl-2,3-dideoxy-α-D-erythro-hexopyranosyl)-2-deoxy-1,3-di-N-benzyl-1,3-di-N-methoxycarbonylstreptamine was 0.37 g (68.7%). $[\alpha]_D^{20}+38°$ (c 1, chloroform).

TLC: $R_f$ 0.3 (ethyl acetate).

PMR data (CDCl₃): δ 1.55 (m, 6 H, H-2,2,2',2',3',3'), 2.02 (2 s, 6 H, 2 OAc), 3.64 (m, 6 H, 2 NCOOMe), 4.10 (m, 2 H, H-6',6'), 4.43 (m, 4 H, 2 C$\underline{H}_2$ Ph), 5.40 (m, 1 H, H-1'α), 7.23 (m, 10 H, 2 Ph).

Analysis: Calcd. for $C_{34}H_{44}N_2O_{12}$: C, 60.70; H, 6.59; N, 4.16. Found: C, 60.62; H, 6.30; N, 4.29%.

Method II

A chloroformic solution (20 ml) of 4-O (4,6-di-O-acetyl-2,3-dideoxy-α-D-erythro-hexopyranosyl)-5,6-O-cyclohexylidene-2-deoxy-1,3-di-N-benzyl-1,3-di-N-methoxycarbonylstreptamine (0.15 g, 0.2 mmol), toluene-p-sulphonic acid (20 mg) and methanol (3 ml) was heated at 50°–60° for 2 h, and then neutralized with triethylamine (0.5 ml). Concentration of the reaction mixture and chromatography of the residual syrup as in Method I gave pure amorphous, glassy 4-O (4,6-di-O-acetyl-2,3-dideoxy-α-D-erythro-hexopyranosyl)-2-deoxy-1,3-di-N-benzyl-1,3-di-N-methoxycarbonylstreptamine (0.117 g, 87%). $[\alpha]_D^{20}+38°$ (c 1, chloroform).

TLC: $R_f$ 0.30 (ethyl-acetate).

IR: $\nu_{max}^{CHCl_3}$ 3440 (OH), 1745 (OAc), 1695 (NCOOMe) cm⁻¹.

The PMR spectrum of this product was identical to that of the compound prepared according to Method I.

Analysis: Calcd. for: $C_{34}H_{44}N_2O_{12}$: C, 60.70; H, 6.59; N, 4.16. Found: C, 60.75; H, 6.47; N, 4.07%.

EXAMPLE XLII

When 6-O-(4,6-di-D-acetyl-2,3-dideoxy-α-D-erythro-hexopyranosyl)-4,5-O-cyclohexylidene-1,3-di-N-benzyl-1,3-di-N-methoxycarbonylstreptamine was reacted under the same conditions and with identical quantities of reagent as in the case of the 4-O- isomer described in Example XLI, Method II, the corresponding 6-O-(4,6-di-O-acetyl-2,3-dideoxy-α-D-erythro-hexopyranosyl)-2-deoxy-1,3-di-N-benzyl-1,3-di-N-methoxycarbonylstreptamine (99.5 mg, 74%) was obtained as a glassy product. $[\alpha]_D^{20}+21.5°$ (c 1, chloroform).

TLC: $R_f$ 0.40 (ethyl acetate).

IR: $\nu_{max}^{CHCl_3}$ 3440 (OH), 1745 (OAc), 1695 (NCOOMe) cm⁻¹.

PMR data (CDCl₃, 100°): δ 1.40–1.90 (m, 6 H, H-2,2,2',2',3',3'). 2.00 (2 s, 6 H, 2 OAc), 3.65 (2 s, 6 H, 2 NCOOMe), 4.65 (m, 1 H, H-1'α), 7.17 (m, 10 H, 2 Ph).

Analysis: Calcd. for: $C_{34}H_{44}N_2O_{12}$: C, 60.70; H, 6.59; N, 4.16. Found: C, 60.90; H, 6.64; N, 4.26%.

EXAMPLE XLIII

Carbon tetrachloride (0.5 ml) and hexamethylphosphorous triamide (0.6 ml) were added to a solution of (4-O-(2,3-dideoxy-α-D-erythro-hexopyranosyl) 5,6-O-cyclohexylidene-2-deoxy-1,3-di-N-benzyl-1,3-di-N-methoxycarbonylstreptamide (0.64 g, 0.95 mmol) in dry N,N-dimethylformamide (4 ml). The mixture was stirred at −45° under nitrogen for 1.5 h. Sodium azide (0.8 g) was then added, the mixture was stirred at 80° for 12 h, and it was poured into ice-water and ether extracted. The extracts were washed with water, dried and concentrated to give a glassy residue which was purified by silica gel column chromatography using benzene-chloroform mixtures as eluant. The solid isolated was recrystallized from ether-petrol to give pure 4-O-(6-azido-2,3,6-trideoxy-α-D-erythro-hexopyranosyl)-5,6-O-cyclohexylidene-2-deoxy-1,3-di-N-benzyl-1,3-di-N-methoxycarbonylstreptamine (0.5 g, 76%), M.p.: 105°–108° (sinters at 79°). $[\alpha]_D^{23}+31°$ (c 1, chloroform).

TLC: $R_f$ 0.7 (ethyl acetate); $R_f$ 0.55 (chloroform, ethyl acetate, 1:1).

IR: $\nu_{max}^{CHCl_3}$ 3420 (OH), 2100 (N₃), 1690 (NCOOMe), 1605 (Ph) cm⁻¹.

PMR data (CDCl₃, 80°): δ 1.29–2.00 (bm, 16 H, H-2,2,2',2',3',3' and 10 cyclohexylidene protons), 3.67 (d, 6 H, 2 NCOOMe), 5.29 (m, 1 H, H-1'α), 7.18 (bm, 10 H, 2 Ph).

Analysis: Calcd. for $C_{36}H_{47}N_5O_9$: C, 62.32; H, 6.82; N, 10.07. Found: C, 62.54; H, 7.02; N, 9.73%.

EXAMPLE XLIV

4-O-(6-azido-2,3,6-trideoxy-α-D-erythro-hexopyranosyl)-5,6-O-cyclohexylidene-2-deoxy-1,3-di-N-benzyl 1,3-di-N-methoxycarbonylstreptamine (0.14 g, 0.21 mmol) was acetylated (pyridine, 2 ml; Ac$_2$O, 0.2 ml) for 12 h at 22°. The mixture was poured into ice-water and extracted with chloroform. The extracts were washed with water, dried and concentrated to give a solid. This was recrystallized from benzene-petroleum (40°-60°) to yield pure 4-O-(4-O-acetyl-6-azido-2,3,6-trideoxy-α-D-erythro-hexopyranosyl)-5,6-O-cyclohexylidene-2-deoxy-2,3-di-N-benzyl-1,3-di-N-methoxycarbonylstreptamine, (0.13 g), m.p.: 73°-75°. [α]$_D^{23}$+56° (c 1, chloroform).

TLC: R$_f$ 0.6 (chloroform-ethyl acetate, 5:1); R$_f$ 0.5 benzene-ethyl acetate, 5:1).

IR: $v_{max}^{CHCl_3}$ 2105 (N$_3$), 1735 (OAc), 1690 (NCOOMe), 1610 (Ph) cm$^{-1}$.

PMR data (CDCl$_3$, 80°): δ 1.28-1.97 (bm, 16 H, H-2,2,2',2',3',3' and 10 cyclohexylidene protons), 2.00 (s, 3 H, OAc), 3.28 (m, 2 H, CH$_2$N$_3$), 3.66 and 3.68 (2 s, 6 H, 2 NCOOMe), 4.25 (m, 1 H, H-5'), 4.73 (m, 1 H, H-4'), 5.33 (m, 1 H, H-1'), 7.18 (m, 10 H, 2 Ph).

Analysis: Calcd. for C$_{38}$H$_{49}$N$_5$O$_{10}$: C, 62.02; H, 6.66; N, 9.52. Found: C, 61.93; H, 6.50; N, 9.70%.

EXAMPLE XLV

A mixture of 4-O-(6-azido-2,3,6-trideoxy-α-D-erythro-hexopyranosyl)-5,6-O-cyclohexylidene-1,3-di-N-benzyl-1,3-di-N-methoxycarbonyl-2-deoxystreptamine (0.12 g, 0.18 mmol), isopropyl (4 ml), 90% hydrazine hydrate (5 ml) and 10% palladium-on-charcoal (30 mg) was boiled under reflux and nitrogen for 24-36 h. The solution was filtered, the catalyst was washed with ethanol and the combined organic liquids were concentrated and repeatedly azeotroped with water to remove excess of hydrazine. The syrupy residue was extracted with chloroform, the extracts, after concentration, gave a solid which was purified by preparative TLC. Pure 4-O-(6-amino-2,3,6-trideoxy-α-D-erythro-hexopyranosyl)-5,6-O-cyclohexylidene-2-deoxy-1,3-di-N-benzylstreptamine (68 mg, 67%) was obtained. M.p.: 182°-186° (sinters at 89°), [α]$_D^{24}$+60° (c 0.9, methanol).

TLC: R$_f$ 0.25 (methanol-acetone, 6:1).

IR: $v_{max}^{CHCl_3}$ 3300 (OH, NH, NH$_2$), 1600 (Ph) cm$^{-1}$.

PMR data (CDCl$_3$): δ 1.58 (bm, 16 H, H-2,2,2',2',3',3' and 10 cyclohexylidene protons), 3.85 (bm, 4 H, 2 CH$_2$ Ph), 4.80 (b. band, 5 H, 10 H, 2 NH, 1 NH$_2$), 5.37 (m, 1 H, H-1'α), 7.26 (m, 10 H, 2 Ph).

Analysis: Calcd. for C$_{32}$H$_{45}$N$_3$O$_5$: C, 69.66; H, 8.22; N, 7.62. Found: C, 69.80; H, 8.04; N, 7.74%.

EXAMPLE XLVI

Carbon tetrachloride (1 ml) and hexamethylphosphorous triamide were added to a solution of 4-O-(2,3-dideoxy-α-D-erythro-hexopyranosyl)-5,6-O-cyclohexylidene-2-deoxy-1,3-di-N-benzyl-1,3-di-N-methoxycarbonylstreptamine (0.64 g, 0.95 mmol) in dry N,N-dimethylformamide (4 ml). The mixture was stirred at -20° under nitrogen for 1.5 h after which sodium azide (1.0 g) was added and the mixture was stirred at 80° for 12 h. It was then poured into ice-water and extracted with ether. The extracts were washed with water, dried and concentrated to give a glassy residue which was recrystallized from ether-petroleum. 4-O-(4,6-diazido-2,3,4,6-tetradeoxy-α-D-threo-hexopyranosyl)-5,6-O-cyclohexylidene-2-deoxy-1,3-di-N-benzyl-1,3-di-N-methoxycarbonylstreptamine was obtained in 83% yield (0.57 g). M.p.: 118°-121° (sinters at 108°). [α]$_D^{21}$+36.7° (c 0.74, chloroform).

TLC: R$_f$ 0.5 (chloroform-ethyl acetate, 3:2).

IR: $v_{max}^{CHCl_3}$ 2105 (N$_3$), 1690 (NCOOMe), 1600 (Ph) cm$^{-1}$.

PMR data (CDCl$_3$, 100°): δ 1.57 (m, 16 H, H-2,2,2',2',3',3' and 10 cyclohexylidene protons), 3.66 (s, 6 H, NCOOMe), 4.43 (m, 4 H, 2 CH$_2$ Ph), 5.34 (m, 1 H, H-1'α), 7.19 (m, 10 H, 2 Ph).

Analysis: Calcd. for: C$_{36}$H$_{46}$N$_8$O$_8$: C, 60.52; H, 6.43; N, 15.55. Found: C, 60.71; H, 6.32; N, 15.65%.

EXAMPLE XLVII

A mixture of 4-O-(4,6-di-azido-2,3,4,6-tetradeoxy-α-D-threo-hexopyranosyl)-5,6-O-cyclohexylidene-2-deoxy-1,3-di-N-benzyl-1,3-di-N-methoxycarbonylstreptamine (0.1 g, 0.14 mmol), chloroform (6 ml), toluene-p-sulphonic acid (20 mg) and methanol (3 ml) was heated at 55°-60° for 2 h. Triethylamine (0.5 ml) was then added and the mixture was stirred for a further 15 minutes and concentrated to dryness. The residue was extracted with chloroform, the extracts were washed with water, dried and concentrated to give a syrup which was purified by silica gel column chromatography (benzene-chloroform as eluant). 4-O-(4,6-diazido-2,3,4,6-tetradeoxy-α-D-threo-hexopyranosyl)-1,3-di-N-benzyl-1,3-di-N-methoxycarbonyl-2-deoxystreptamine was obtained as a colourless solid (85 mg, 95%). M.p.: 134°-137° (softens at 119°). [α]$_D^{24}$+20° (c 0.28, chloroform).

TLC: R$_f$ 0.2 (chloroform-ethyl acetate, 1:1).

IR: $v_{max}^{CHCl_3}$ 3420 (OH), 2105 (N$_3$) 1690 (NCOOMe), 1605 (Ph) cm$^{-1}$.

PMR data (CDCl$_3$, 80°): δ 1.29 (s, 1 H, H-2ax), 1.90 (m, 5 H, H-2eq, 2',2',3',3'), 2.85 (bm, 2 H, 2 —OH), 3.68 and 3.72 (2 s, 6 H, 2 NCOOMe), 5.40 (m, 1 H, H-1'α), 7.21 (m, 10 H, 2 Ph).

Analysis: Calcd. for: C$_{30}$H$_{38}$N$_8$O$_8$: C, 56.42; H, 5.99; N, 17.54. Found: C, 56.60; H, 6.04; N, 17.68%.

EXAMPLE XLVIII

A mixture of 4-O-(6-azido-2,3,6-trideoxy-α-D-erythro-hexopyranosyl)-5,6-O-cyclohexylidene-2-deoxy-2,3-di-N-benzyl-1,3-di-N-methoxycarbonylstreptamine (0.344 g, 0.5 mmol) and tri-O-acetyl-D-glucal (0.204 g, 0.75 mmol) in dry benzene (15 ml) was treated with boron trifluoride etherate (0.05 ml) and the mixture was stirred for 25 minutes at 22°. Triethylamine (1 ml) was added and the stirring was continued for 20 minutes. The mixture was washed with water, dried and concentrated to yield a glassy material which was dissolved in dry methanol (10 ml) and catalytically deacetylated with sodium methoxide (20 mg) for 12 h at 22°. Neutralization of the mixture with CO$_2$ was followed by concentration to give a syrup. This was extracted with chloroform, and the extracts were concentrated and eluted from silica gel (benzene-chloroform) to give pure 4-O-[4-O-(2,3-dideoxy-α-D-erythro-hex-2-enopyranosyl)-6-azido-2,3,6-trideoxy-α-D-erythro-hexopyranosyl]-5,6-O-cyclohexylidene-2-deoxy-1,3-di-N-benzyl-1,3-di-N-methoxycarbonylstreptamine, (0.312 g, 76%), M.p.: 126°-130° (decomp.), [α]$_D^{23}$+48° (c 0.4, chloroform).

TLC: R$_f$ 0.2 (ethyl acetate-chloroform, 2:1).

IR: $v_{max}^{CHCl_3}$ 3430 (OH), 2100 (N$_3$), 1695 (NCOOMe), 1600 (Ph) cm$^{-1}$.

PMR data (CDCl$_3$, 80°): δ 1.58 (m, 16 H, H-2,2,2',2',3',3' and 10 cyclohexylidene protons), 2.25 (b band, 2 H, 2 OH), 3.70 (m, 6 H, 2 NCOOMe), 4.48 (m, 4 H, 2 CH$_2$-Ph), 5.33 (m, 1 H, H-1'α), 5.50 (m, 1 H, H-1''α), 5.94 (m, 2 H, H-2'',3''), 7.26 (m, 10 H, 2 Ph).

Analysis: Calcd. for C$_{42}$H$_{55}$N$_5$O$_{12}$: C, 61.37; H, 6.74; N, 8.52. Found: C, 61.53; H, 6.51; N, 8.47%.

EXAMPLE XLIX

A mixture of 4-O-(6-azido-2,3,6-trideoxy-α-Derythro-hexopyranosyl)-5,6-O-cyclohexylidene-2-deoxy-1,3-di-N-benzyl-1,3-di-N-methoxycarbonylstreptamine (0.35 g, 0.55 mmol) and 6-azido-6-deoxy-3,4-di-O-acetyl-D-glucal (0.167 g, 0.65 mmol, 20% excess) in dry benzene (15 ml) was treated with boron trifluoride etherate (0.05 ml) and stirred at 22° for 25 minutes. Triethylamine (0.5 ml) was added and the mixture, after stirring for 15 minutes, was washed with water, dried and concentrated to give a solid. This was purified by silica gel column chromatography (benzene-chloroform as eluant) to give pure, amorphous, glassy, 4-O-[4-O-(4-O-acetyl-6-azido-2,3,6-trideoxy-α-D-erythro-hex-2-enopyranosyl)-6-azido-2,3,6-trideoxy-α-D-erythro-hexopyranosyl]-5,6-O-cyclohexylidene-2-deoxy-1,3-di-N-benzyl-1,2-di-N-methoxycarbonylstreptamine (0.46 g, 88%). [α]$_D^{22}$+42.5° (C 0.46, chloroform).

TLC: R$_f$ 0.3 (benzene-ethyl acetate, 5:1).

IR: $\nu_{max}^{CHCl_3}$ 2110 (N$_3$), 1740 (OAc), 1700 (NCOOMe), 1605 (Ph) cm$^{-1}$.

PMR data (CDCl$_3$, 80°), δ 1.58 (m, 16 H, H-2,2,2′,2′,3′,3′ and 10 cyclohexylidene protons), 2.08 (s, 3 H, OAc), 3.67 (s, 6 H, 2 NCOOMe) 5.23 (m, 1 H, H-1′α), 5.34 (m, 1 H, H-1″α), 5.84 (m, 2 H, H-2″,3″), 7.21 (m, 10 H, 2 Ph).

Analysis: Calcd. for: C$_{44}$H$_{56}$N$_8$O$_{12}$: C, 59.45; H, 6.35; N, 12.60. Found: C, 59.31; H, 6.52; N, 12.59%.

EXAMPLE L

A solution of 4-O-[4-O-(4-O-acetyl-6-azido-2,3,6-trideoxy-α-D-erythro-hex-2-enopyranosyl)-6-azido-2,3,6-trideoxy-α-D-erythro-hexopyranosyl]-5,6-O-cyclohexylidene-2-deoxy-1,3-di-N-benzyl-1,3-di-N-methoxycarbonylstreptamine (0.25 g, 0.28 mmol) in dry methanol (10 ml) was catalytically deacetylated with sodium methoxide (20 mg) at 20° for 12 h. Neutralization of the mixture with CO$_2$ followed by concentration to dryness led to a residue which was extracted with chloroform. The extracts, washed with water and dried, gave a solid which was eluted from silica gel (benzene-chloroform mixtures) to give 0.23 g (96%) of pure 4-O-[4-O-(6-azido-2,3,6-trideoxy-α-D-erythro-hex-2-enopyranosyl)-6-azido-2,3,6-trideoxy-α-D-erythro-hexopyranosyl] 5,6-O-cyclohexylidene-2-deoxy-1,3-di-N-benzyl-1,3-di-N-benzyl-1,3-di-N-methoxycarbonylstreptamine, M.p.: 126°-132°. [α]$_D^{22}$+34° (c 0.68, chloroform).

TLC: R$_f$ 0.5 (benzene-ethyl acetate, 1:1); R$_f$ 0.3 (benzene-ethyl acetate, 2:1); R$_f$ 0.25 (chloroform).

IR: $\nu_{max}^{CHCl_3}$ 3420 (OH), 2100 (N$_3$), 1690 (NCOOMe), 1600 (Ph) cm$^{-1}$.

PMR data (CDCl$_3$): δ 1.55 (bm, 16 H, H-2,2,2′,2′,3′,3′ and 10 cyclohexylidene protons), 2.40 (b, 1 H, OH), 3.65 (bm, 6 H, 2 NCOOMe), 5.15 (m, 1 H, H-1′α); 5.31 (m, 1 H, H-1″α), 5.85 (m, 2 H, H-2″,3″), 7.25 (m, 10 H, 2 Ph).

Analysis: Calcd. for: C$_{42}$H$_{54}$N$_8$O$_{11}$: C, 59.56; H, 6.43; N, 13.23. Found: C, 59.65; H, 6.63; N, 13.29%.

EXAMPLE LI

A mixture of 4-O-[4-O-(4-acetyl-6-azido-2,3,6-trideoxy-60-D-erythro-hex-2-eno-pyranosyl)-6-azido,2,3,6-trideoxy-α-D-erythro-hexopyranosyl]-5,6-O-cyclohexylidene-2-deoxy-1,3-di-N-benzyl-1,3-di-N-methoxycarbonylstreptamine (111 mg, 0.125 mmol), 90% hydrazine hydrate (3 ml), isopropanol (2ml) and 10% palladium-on-charcoal (20 mg) were heated under nitrogen at 110° for 20 h. The mixture was evaporated (2 Torr.) and redissolved in methanol (10 ml), neutralized with 1 N HCl and hydrogenated with fresh palladium catalyst (30 mg) at 3 atmos, for 7 h. The catalyst was filtered and washed with methanol. The combined organic liquids were acidified to pH 4 with HCl, heated at 40°-50° for 1 h, and then tested for the presence of cyclohexylidene protecting group by evaporating an aliquot of the solution to dryness, spotting a drop of the residue in a TLC plate and spraying with anisaldehyde reagent (anisaldehyde in acetic acid containing 5% H$_2$SO$_4$) and heating at 110°. The absence of a carmine coloured spot showed that the hydrolysis of the cyclohexylidene group had taken place. The solution was evaporated, taken in 1 ml of water and eluted from CG 50 Amberlite (NH$^+$) resin column with water, then with 1 N, and 1.5 N aqueous ammonia. The eluates were evaporated to a small volume, neutralized with 1 N H$_2$SO$_4$ and treated with 3 volumes of methanolacetone (1:1). The precipitate was redissolved in water (1 ml) and reprecipitated as before. 4-O-[4-O-(6-amino-2,3,6-trideoxy-α-O-erythro-hexopyranosyl)-6-amino-2,3,6-trideoxy-αO-erythro-hexopyranosyl]-2-deoxystreptamine disulphate (50 mg, 65%) was obtained as an amorphous, hygroscopic powder. M.p.~250° decomposition. [α]$_D^{24}$+135° (c 1, water).

TLC: R$_f$ 0.35 (methanol-NH$_4$OH, 8:1). Equivalent weight: (in glacial acetic acid): Calcd. 154. Found, 153.

Mass spectrum: M/e 421.

Calcd. for C$_{18}$H$_{36}$N$_4$O$_7$: M$^{+1}$ 421.

Analysis: Calcd. for C$_{18}$H$_{36}$N$_4$O$_7$.2 H$_2$SO$_4$: C, 35.06; H, 6.54; N, 9.08. Found: C, 35.42; H, 6.69; N, 8.93%.

EXAMPLE LII

A mixture of 2-deoxy-1,3-di-N-benzylstreptamine-1,6:3,4-dicarbamate (500 mg, 1.27 mmol) and tri-O-acetylglucal (700 mg, 2.57 mmol) in freshly prepared dry chloroform (200 ml) was treated with borom trifluoride etherate (1 ml) for 10 minutes at 22° with stirring. Triethylamine (3 ml) was added and the reaction mixture was washed with water, dried and concentrated to yield a syrup. This was extracted with light petroleum and the extracts were discarded. The residue was then dissolved in benzene, ether was added to precipitate the starting material and the solution, after filtration, was concentrated to a syrup. This was crystallized from benzene-light petroleum to give 0.75 g of a product which showed two spots on TLC examination (chloroform-ethyl acetate, 2:1), R$_f$ 0.35 (main component) and R$_f$ 0.25 (minor component). A sample of the main component (50 mg) was purified by silica gel column chromatography using benzene-chloroform (1:1) as eluant followed by recrystallization from benzene-petroleum ether to give colourless, pure 5-O-(4,6-di-O-acetyl-2,3-dideoxy-α-D-erythro-hex-2-enopyranosyl-2-deoxy-1,3-di-N-benzylstreptamine-1,6:3,4-dicarbamate. M.P. 75°-80°. ]α]$_D^{23}$+72° (c 1, chloroform).

TLC: R$_f$ 0.35 (chloroform-ethyl acetate, 2:1).

IR: $\nu_{max}^{CHCl_3}$ : 1760 (—NCOO), 1730 (OAc), 1600 (Ph), 1585 (Ph), 1495 (Ph) cm$^{-1}$.

PMR data (CDCl$_3$): δ 1.25 (m, 1 H, H-2ax), 1.91 (m, 1 H, H-2eq), 1.99 and 2.07 (2 s, 6 H, 2 OAc), 2.94 (dt, 2 H, H-1,3, J$_{1,6}$=J$_{3,4}$=11 Hz, J$_{1,2eq}$=J$_{3,2eq}$=3 Hz), 3.85 (t, 2 H, H-4,6, J$_{1,6}$=J$_{2,3}$=11 Hz), 4.16 (m, 1 H, H-5), 4.22 (m, 2 H, H-6′,6′), 4.37 (q, 4 H, 2 CH$_2$), 5.28 (m, 1 H, H-1′α), 5.88 (m, 2 H, H-2′,3′), 7.25 (m, 10 H, 2 Ph).

Analysis: Calcd. for: $C_{32}H_{34}N_2O_{10}$: C, 63.36; H, 5.65; N, 4.62. Found: C, 63.41; H, 5.89; N, 4.85%.

EXAMPLE LIII

The crude solid (0.72 g) isolated in the previous Example in methanol (50 ml), was hydrogenated for 3 h at atmospheric pressure over 10% palladium-on-charcoal catalyst (0.2 g). After filtering the catalyst the combined filtrate and washings were concentrated to give a syrup (0.72 g) which was purified by silica gel column chromatography using benzene-chloroform (1:1) as eluant. Two components were separated in this way: (TLC chloroform-ethyl acetate, 2:1):
(a) main component $R_f$ 0.35
(b) minor component, $R_f$ 0.25.
The main component (a) was recrystallized from benzene-light petroleum to give 600 mg) 77%) of 5-O-(4,6-di-O-acetyl-2,3-dideoxy-α-D-erythro-hexopyranosyl)-2-deoxy 1,3-di-N-benzylstreptamine-1,6:3,4-dicarbamate, m.p.: 91°–93°. $[\alpha]_D^{23} + 82.5°$ (c 0.67, chloroform).

TLC: $R_f$ 0.35 (chloroform-ethyl acetate, 2:1).

IR: $\nu_{max}^{CHCl_3}$: 1760 (—NCOO—), 1730 (OAc), 1495 (Ph) cm$^{-1}$.

PMR data (CDCl$_3$): δ 1.25 (m, 1 H, H-2ax), 1.86 (m, 5 H, H-2′,2′,3′,3′ and 2 eq), 1.98 and 2.02 (2 s, 6 H, 2-OAc), 2.94 (dt, 2 H, $J_{1,6}=J_{3,4}=11$ Hz, $J_{1,2eq}=J_{3,2eq}=(J_{3,2eq})=3$ Hz, H-1,3), 3.84 (dt, 2 H, H-4,6), 4.13 (m, 2 H, H-6′, 6′), 4.35 (q, 4 H, 2 CH$_2$—Ph), 4.75 (m, 1 H, H-4′), 5.11 (m, 1 H, H-1′α), 7.23 (m, 10 H, 2 Ph).

Analysis: Calcd. for: $C_{32}H_{36}N_2O_{10}$: C, 63.15; H, 5.96; N, 4.60. Found: C, 63.25; H, 6.17; N, 4.54%.

EXAMPLE LIV

Component (b) isolated from the chromatographic column in the previous Example was identified as the pure 5-O-(4,6-di-O-acetyl-2,3-dideoxy-β-D-erythro-hexopyranosyl)-2-deoxy 1,3-di-N-benzylstreptamine-1,6:3,4-dicarbamate. It was recrystallized from benzene-light petroleum and from methanol to give 45 mg (6%) of a colourless product. M.p.: 195°–197°. $[\alpha]_D^{20} - 1°$ (c 1, chloroform).

IR: $\nu_{max}^{CHCl_3}$: 1760 (—NCOO—), 1730 (OAc), 1495 (Ph) cm$^{-1}$.

PMR data (CDCl$_3$): δ 1.25 (m, 1 H, H-2ax), 1.50–2.00 (m, 5 H, H-2′,2′,3′,3′, and 2eq), 2.02 (s, 6 H, 2 OAc), 2.95 (m, 2 H, H-1,3), 3.84 (t, 2 H, $J_{1,6}=J_{3,4}=10.5$ Hz,H-4,6), 4.17 (m, 2 H, H-6′,6′), 4.35 (q, 4 H, 2 CH$_2$Ph), 4.65 (m, 2 H, H-1′β, 4′), 7.25 (m, 10 H, 2 Ph).

Analysis: Calcd. for: $C_{32}H_{36}N_2O_{10}$: C, 63.15; H, 5.96; N, 4.60. Found: C, 63.31; H, 6.03; N, 4.53%.

EXAMPLE LV

5-O-(4,6-Di-O-acetyl-2,3-dideoxy-α-D-erythro-hexopyranosyl)-1,3-di-N-benzyl-2-deoxystreptamine-1,6:3,4-dicarbamate (176 mg, 0.29 mmol) was heated under reflux in 1N methanolic solution of sodium hydroxide (10 ml) overnight. TLC examination revealed a single spot, $R_f$ 0.18 (benzenemethanol, 2:1) ninhydrin positive. The mixture was neutralized with CO$_2$ and solvents were removed in vacuo. The residue was dissolved in acetone-water (1:1) and sodium carbonate (300 mg) was added. The mixture was cooled at 0° and benzyl chloroformate (0.1 ml, 0.7 mmol) was added. The mixture was stirred at room temperature overnight, after which the solvents were removed under diminished pressure. The residue was dissolved in water and extracted with chloroform, the extracts were washed with water, dried and concentrated to a syrup. This was crystallized from benzene-light petroleum to give 167 mg (78%) of 5-O-(2,3-dideoxy-α-D-erythro-hexopyranosyl)-2-deoxy-1,3-di-N-benzyl-1,3-di-N-benzyloxycarbonylstreptamine, m.p.: 70°–75°. $[\alpha]_D^{24} + 62.5°$ (c 1, chloroform).

TLC: $R_f$ 0.20 (ethyl acetate); $R_f$ 0.55 (benzene-methanol, 2:1).

IR: $\nu_{max}^{CHCl_3}$: 3420 (OH), 1685 (—NCOO), 1605, 1585 and 1495 (Ph) cm$^{-1}$.

PMR data (CDCl$_3$, 80°): δ 1.40–1.90 (m, 6 H, 2 H-2′, 2 H-3′, H-2ax and H-2eq), 2.40 (bm, 4 H, 4 OH, disappears with D$_2$O), 3.20–3.85 (m, 9 H, H-1,3,4,5,6,4′,5′,6′,6′), 4.41 (m, 4 H, 2 NCH$_2$—Ph), 5.10 (m, 5 H, H-1′α and 2—COOCH$_2$—Ph), 7.20 (m, 20 H, 4 Ph).

Analysis: Calcd. for: $C_{42}H_{48}N_2O_{10}$: C, 68.09; H, 6.53; N, 3.78. Found: C, 68.00; H, 6.70; N, 3.64%.

EXAMPLE LVI

5-O-(4,6-Diacetyl-2,3-dideoxy-α-D-erythro-hexopyranosyl)-2-deoxy-1,3-di-N-benzylstreptamine-1,6:3,4-dicarbamate (1.40 mg, 0.23 mmol) in 1N methanolic sodium hydroxide (5 ml) was heated under reflux for 12 h. The mixture was concentrated to dryness after neutralization with CO$_2$. The residue was extracted with methanol, the extracts were concentrated to yield a glassy product, and this was extracted with chloroform. The residue left after removal of the solvent was recrystallized from chloroform-light petroleum to yield 97 mg (89%) from which the hydrochloride of 5-O-(2,3-dideoxy-α-D-erythro-hexopyranosyl-2-deoxy-1,3-di-N-benzylstreptamine (dihydrochloride) was prepared by addition of 0.5N HCl to a solution of the base in water to pH 6. $[\alpha]_D^{22} + 60°$ (c 0.9, methanol).

TLC: $R_f$ 0.18 (benzene-methanol, 2:1); $R_f$ 0.70 (chloroform-methanol-35% ammonia, 20:6:1).

IR: $\nu_{max}^{nujol}$: 3340 (OH, NH), 1050 (glycoside), 700 (Ph) cm$^{-1}$.

PMR data (D$_2$O): δ 1.60–2.15 (m, 5 H, H 2′,2′,3′,3′,2ax), 2.55 (m, 1 H, 2-2eq), 3.20 (m, 2 H, H-1,3), 3.50–4.00 (m, 7 H, H-4,4′,5,5′,6,6′,6′), 4.38 (m, 4 H, 2 CH$_2$—Ph), 5.25 (m, 1 H, H-1′α), 7.56 (m, 10 H, 2 Ph).

Analysis: Calcd. for: $C_{26}H_{36}N_2O_6$: C, 66.08; H, 7.68; N, 5.93. Found: C, 66.20; H, 7.80; N, 6.04%.

EXAMPLE LVII

5-O-(2,3-Dideoxy-α-D-erythro-hexopyranosyl)-2-deoxy-1,3-di-N-benzylstreptamine dihydrochloride (50 mg, 0.092 mmol) in dry methanol (5 ml) was hydrogenated over 10% palladium-on-charcoal catalyst (70 mg) at atmospheric pressure overnight. The catalyst was filtered and washed with methanol and water. Evaporation of the combined filtrate and washings gave 31 mg (92%, calc. on dihydrochloride salt) of a hydroscopic 5-O-(2,3-dideoxy-α-D-erythro-hexopyranosyl)-2-deoxystreptamine dihydrochloride. M.p.: >250°. $[\alpha]_D^{24}30$ 74.5° (c 1.5, methanol).

TLC: $R_f$ 0.20 (methanol - 35% ammonia, 8:1); $R_f$ 0.40 (methanol - 35% ammonia, 2:1).

PMR data (O$_2$D): δ 1.60–2.00 (m, 5 H, H-2′,2′,3′,3′,2ax), 2.45 (m, 1 H, H-2eq), 3.10–4.00 (m, 9 H, H-1,3,4,5,6,4′,5′,6′,6′), 5.27 (m, 1 H, H-1′α).

Analysis: Calcd. for: $C_{12}H_{26}Cl_2N_2O_6$: C, 39.45; H, 7.17; N, 7.67; Cl, 19.41. Found: C, 39.60; H, 7.09; N, 7.75; Cl, 19.80.

EXAMPLE LVIII

Carbon tetrachloride (0.1 ml) and hexamethyl-phosphorous triamide (0.2 ml) were added to a solution of 5-O-(2,3-dideoxy-α-D-erythro-hexopyranosyl)-2-deoxy)-1,3-di-N-benzyl-1,3-di-N-benzyloxycarbonylstreptamine (120 mg, 0.162 mmol) in dry N,N-dimethylformamide (2.0 ml). The mixture was stirred at −50° under nitrogen for 10 minutes. Sodium azide (130 mg, 2.0 mmol) was then added and the mixture was stirred at 80° for 8 h. It was then poured into ice and water and extracted with ether. The ethereal extracts were washed with water, dried and concentrated to give a syrup which crystallized from benzene-light petroleum. The crude product (119 mg) was eluted from a dry silica gel column (20 cm × 1 cm) with chloroform. The major component was isolated as a glassy solid which crystallized from benzene-petroleum ether. 5-O-(6-Azido-2,3,6-trideoxy-α-D-erythro-hexopyranosyl)-2-deoxy-1,3-di-N-benzyl-1,3-di-N-methoxycarbonylstreptamine (80 mg, 65%) had m.p.: 60°-62°. $[\alpha]_D^{23}+28°$ (c 0.8, chloroform).

TLC: $R_f$ 0.53 (ethyl acetate); $R_f$ 0.50 (benzene-methanol, 4:1); $R_f$ 0.20 (chloroform-ethyl acetate, 1:1).

IR: $\nu_{max}^{CHCl_3}$: 3420 (OH), 2100 (N$_3$), 1690 (NCOO-Me), 1610, 1590 and 1500 (Ph)cm$^{-1}$.

PMR data (CDCl$_3$, 80°): δ 1.25-1.90 (m, 6 H, H-2ax, 2eq, 2',2',3',3), 3.20-3.90 (m, 9 H, H-1,3,4,5,6,4',5',6',6'), 4.40 (m, 4 H, 2 C$\underline{H}_2$—Ph), 5.10 (m, 5 H, H-1' α and 2 COOC$\underline{H}_2$—Ph), 7.20 (m, 20 H, 4 Ph).

Analysis: Calc. for C$_{42}$H$_{47}$N$_5$O$_9$: C, 65.86; H, 6.19; N, 9.15. Found: C, 65.74; H, 6.20; N, 9.30%.

EXAMPLE LIX

2-Deoxy-1,3-di-N-benzylstreptamine dihydrochloride (3.0 g, 7.2 mmol) and sodium carbonate (5 g) were dissolved in water-acetone (2:1, 150 ml). Phenyl chloroformate (2.1 ml, 16.5 mmol, 14% excess) in acetone (50 ml) was added dropwise to the mixture at −10° with stirring. After 3 h the reaction mixture was evaporated and the product which separated upon the addition of water was filtered and washed with water. Recrystallization from chloroform-ether-petroleum ether yielded 3.2 g (76%) of pure 2-deoxy-1,3-di-N-benzyl-1,3-di-N-phenyloxycarbonylstreptamine. M.p.: 96°-100°.

TLC: $R_f$ 0.30 (ethyl acetate).

Analysis: Calcd. for: C$_{34}$H$_{34}$N$_2$O$_7$: C, 70.17; H, 5.88; N, 4.80. Found: C, 70.20; H, 5.96; N, 4.83%.

EXAMPLE LX

A mixture of 2-deoxy-1,3-di-N-benzyl-1,3-di-N-phenyloxycarbonylstreptamine (3.0 g, 5.1 mmol), sodium hydride (60% oil dispersed, 0.66 g, 16.5 mmol) and N,N-dimethylformamide was stirred at 0° for 4 h, after which solid CO$_2$ was added to neutralize it and the solvents were evaporated in vacuo. The residue was treated with water, thus obtaining a precipitate which was filtered off and dried. Two recrystallizations from hot methanol gave 0.84 g (41%) of pure 2-deoxy-1,3-di-N-benzylstreptamine-1,6:3,4-dicarbamate. M.p.: 243°-248°.

TLC: $R_f$ 0.65 (ethyl acetate).

Analysis: Calcd. for: C$_{22}$H$_{22}$N$_2$O$_5$: C, 66.99; H, 5.62; N, 7.10. Found: C, 70.15; H, 5.60; N, 7.01%.

EXAMPLE LXI

2-Deoxy-1,3-di-N-benzylstreptamine-1,6:3,4-dicarbamate (2.0 g, 5.1 mmol) was dissolved in triphenylphosphite (20 ml) with heating. Bromine (1 ml, 19 mmol) was then added and the warm mixture was shaken for a few minutes. After standing overnight at room temperature, the mixture was diluted with chloroform (200 ml) and washed with 10% Na$_2$CO$_3$ solution (4×50 ml) and water. The organic phase was dried (Na$_2$SO$_4$) and evaporated to give an oily residue. This was dissolved in benzene, petroleum ether (60°-80°) was added to slight turbidity and it was allowed to crystallize in the refrigerator overnight. The solid was recrystallized from hot benzene to yield 1.9 g (82%) of pure 5-bromo-1,3-di-N-benzyl-2,5-dideoxystreptamine-1,6:3,4-dicarbamate. M.p.: 175°-177°.

TLC: $R_f$ 0.50 (chloroform-ethyl acetate, 1:1).

PMR data (CDCl$_3$): δ 1.5-1.90 (m, 2 H, H-2,2), 3.60 (m, 2 H, H-1,3), 4.05 (m, 2 H, H-4,6, J$_{3,4}$=J$_{1,6}$=10 Hz, J$_{4,5}$=J$_{5,6}$=2.2 Hz), 4.33 (m, 4 H, 2 C$\underline{H}_2$—Ph), 4.90 (m, 1 H, H-5), 7.10-7.40 (m, 10 H, 2 Ph).

Analysis:
Calcd. for: C$_{22}$H$_{21}$N$_2$O$_4$Br: C, 57.78; H, 4.63; N, 6.12; Br, 17.
Found: C, 57.84; H, 4.51; N, 6.00; Br, 17.

EXAMPLE LXII

5-Bromo-1,3-di-Ny-benzyl-2,5-dideoxy-1,6:3,4-dicarbamate (3 g, 6.54 mmol) in absolute ethanol (200 ml) containing triethylamine (5 ml) was hydrogenated over 10% palladium-on-charcoal (2 g) for 2 h at 2 atoms. The filtrate, after removal of the catalyst, was concentrated to a small volume and stored at 0° for 12 h. The precipitated product was recrystallized from hot ethanol giving 1,3-di-N-benzyl-2,5-dideoxy-streptamine-1,6:3,4-dicarbamate (1.83 g, 73%). M.p.: 193°-194°.

TLC: $R_f$ 0.65 (ethyl acetate); $R_f$ 0.47 (chloroform-ethyl acetate, 1:1).

PMR data (CDCl$_3$): δ 1.17 (q, 1 H, H-2ax, J=11 Hz), 1.90 (m, 2 H, H-2eq, 5ax), 2.73 (dt, 1 H, H-5eq), 2.95 (td, 2 H, H-1,3), 3.87 (td, 2 H, H-4,6), 4.33 (m, 4 H, 2 C$\underline{H}_2$Ph), 7.25 (m, 10 H, 2 Ph).

Analysis:
Calcd. for: C H N Q : C, 69.82; H, 5.86; N, 7.40.
Found: C, 70.01; H, 5.73; N, 7.63%.

EXAMPLE LXIII 1,3-Di-N-benzyl-2,5-dideoxystreptamine-1,6:3,4-dicarbamate (0.4 g, 1.06 mmol) in 0.5 N methanolic sodium methoxide (16 ml) was heated under reflux for 2 h. Water (5 ml) was added and the heating under reflux was continued for a further 2 h.

TLC (CHCl$_3$—MeOH—NH$_4$OH, 100:30:3) examination of the mixture revealed only one spot, $R_f$ 0.55, ninhydrin positive, corresponding to 1,3-di-N-benzyl-2,5-dideoxystreptamine. Sodium carbonate (0.3 g) was added to the mixture followed by the dropwise addition of methylchloroformate (0.2 ml. 2.6 mmol) in acetone (5 ml) over a period of 15 minutes while the mixture was stirred and cooled to 0°. This stirring was continued for 2 h at 0°, after which the mixture was concentrated and the residue was extracted with chloroform. The extracts were washed with water, dried and concentrated to give a syrup which was extracted with ether. Evaporation of the ethereal solution gave pure, glassy, 1,3-di-N-benzyl-2,5-dideoxy-1,3-di-N-methoxycarbonylstreptamine (0.414 g, 88%).

TLC: $R_f$ 0.35 (ethanol-ethyl acetate, 1:8).

The analytical sample was purified by column chromatography on silica gel using ethyl acetate as eluant.

PMR data (CDCl$_3$): δ 1.25 (m, 1 H, H-2ax), 1.55 (m, 2 H, H-2eq, 5ax), 2.15-2.45 (m, 3 H, 2 OH and H-5eq), 3.60(m, 4 H, H-1,3,4,6), 3.70 (m, 6 H, 2 NCOOMe), 4.38 (m, 4 H, 2 C$\underline{H}_2$Ph), 7.23 (m, 10 H, 2 Ph).

Analysis: Calcd. for: C$_{24}$H$_{30}$N$_2$O$_6$: C, 65.14; H, 6.83; N, 6.33. Found: C, 65.27; H, 6.70; N, 6.42%.

EXAMPLE LXIV

A mixture of 1,3-di-N-benzyl-2-deoxystreptamine-1,6:3,4-dicarbamate (0.394 g, 1 mmol) and sodium hydride (0.024 g, 1 mmol) in dry N,N-dimethylformamide was stirred at −10° for 1 h. Allyl bromide (0.3 ml, 3.5 mmol) was then added and the mixture was stirred at 25° for 5 h. After pouring the mixture into ice-water, the precipitate was recrystallized several times from benzene and chloroform-ether to give 0.318 g, (73%) of crystalline, pure 5-O-allyl-1,3-di-N-benzyl-2-deoxystreptamine-1,6:3,4-dicarbamate. M.p.: 178.5°–180°.

TLC: R$_f$ 0.6 (chloroform-ethyl acetate, 1:1); R$_f$ 0.65 (ethyl acetate).

PMR data (CDCl$_3$): δ 1.25 (m, 1 H, H-2ax), 1.88 (dt, 1 H, J$_{H-2ax, H-2eq}$=11 Hz, J$_{H-2eq, 1}$=J$_{H-2eq, 3}$=3.5 Hz, H-2eq), 2.95 (m, 2 H, H-1,3), 3.85 (m, 3 H, H-4,5,6), 4.23 (dt, 2 H, —O—C$\underline{H}_2$—CH=CH$_2$), 4.34 (q, 4 H, 2-C$\underline{H}_2$Ph), 5.22 (m, 2 H, O—CH$_2$—C=C$\underline{H}_2$), 5.88 (m, 1 H, —O—CH$_2$—C$\underline{H}$=CH$_2$), 7.25 (m, 10 H, 2 Ph).

Analysis: Calcd. for: C$_{25}$H$_{26}$N$_2$O$_5$: C, 69.39; H, 6.03; N, 6.45. Found: C, 69.50; H, 6.15; N, 6.54%.

EXAMPLE LXV

A mixture of 5-O-allyl-1,3-di-N-benzyl-2-deoxystreptamine-1,6:3,4-dicarbamate (0.217 g, 0.5 mmol) in 1N methanolic sodium methoxide (5 ml) was stirred and heated under reflux for 24 h. This was followed by the addition, at 0°, of sodium carbonate (0.3 g) and methyl chloroformate (0.2 ml). The solution was stirred at 0° for 1 h, then at 25° overnight. Concentration of the mixture and addition of water produced a crystalline precipitate (0.228 g, 91%). It was recrystallized from benzene to give pure 5-O-allyl-2-deoxy-1,3-di-N-benzyl-1,3-di-N-methoxycarbonylstreptamine. M.p.: 155°–158°.

TLC: R$_f$ 0.40 (ethyl acetate); R$_f$ 0.70 (ethyl acetate, ethanol, 8:1).

PMR data (CDCl$_3$): δ 1.20–1.80 (bm, 2 H, H-2ax, 2eq), 2.59 (bm, 2 H, 2 OH), 3.11 (m, 1 H, H-5), 3.68 (s, 6 H, 2 NCOOMe), 4.30 (m, 2 H, —OCH$_2$ allyl group), 4.38 (s, 4 H, 2 CH$_2$—Ph), 5.14 and 5.28 (2 dd, 2 H, C=CH$_2$ allyl group), 5.73–6.16 (m, 1 H, —CH=C, allyl group), 7.22 (m, 10 H, 2 Ph).

Analysis: Calcd. for: C$_{27}$H$_{34}$N$_2$O$_7$: C, 65.31; H, 6.87; N, 5.62. Found: C, 65.25; H, 6.93; N, 5.69%.

EXAMPLE LXVI

A solution of 2-deoxystreptamine 1,6:3,4-dicarbamate (0.1 g, 0.5 mmol) in dry N,N-dimethylformamide (4 ml) was treated with sodium hydride (0.1 g, 4 mmol). The suspension was stirred for 1 h at 25° and cooled to 0° while benzyl bromide (2 ml) was added, stirring of the reaction mixture being continued for 24 h at 22°. Dry methanol (2 ml) was then added and the solution was concentrated to dryness. The residue was extracted with chloroform and the extracts were washed with water, dried, filtered and concentrated to yield a syrup which crystallized upon the addition of ethanol. Recrystallization of the solid from ethanol-chloroform gave pure 2-deoxy-1-N,3-N,5-O-tribenzylstreptamine-1,6:3,4-dicarbamate (0.19 g, 60%). M.p.: 192°–193°.

TLC: R$_f$ 0.75 (ethyl acetate-ethanol, 8:1); R$_f$ 0.40 (chloroform).

PMR data (CDCl$_3$): δ 1.25 (m, 1 H, H-2ax), 1.90 (dt, 1 H, J$_{2eq,2ax}$=11.5 Hz, J$_{2eq, 1}$=J$_{2eq,3}$=3.5 Hz, H-2eq), 2.93 (m, 2 H, H-1,3), 3.90 (m, H, H-4,5,6), 4.37 (m, 4 H, 2 NCH$_2$—Ph), 4.82 (s, 2 H, O—CH$_2$Ph), 7.30 (m, 15 H, 3 Ph).

Analysis: Calcd. for: C$_{29}$H$_{28}$N$_2$O$_5$: C, 71.88; H, 5.82; N, 5.78. Found: C, 71.90; H, 5.75; N, 5.80%.

EXAMPLE LXVII

A mixture of 2-deoxy-1-N,3-N,5-O-tribenzylstreptamine-1,6:3,4-dicarbamate (1 g, 2.6 mmol) in methanol (100 ml) and barium hydroxide octahydrate (7.5 g) in water (25 ml) was heated under reflux with stirring for 24 h, after which it was neutralized with solid CO$_2$ and centrifuged to remove the inorganic salts. The supernatant was concentrated to dryness, and the residue was dissolved in chloroform (25 ml), filtered and treated with an ethereal solution of HCl until pH 2 was reached. Ether was then added to effect complete precipitation. The solid (1.012 g, 97%) was recrystallized from methanol-ether to give pure 2-deoxy-1-N,3-N,5-O-tribenzylstreptamine dihydrochloride as a white solid. M.p.: 185°–190°.

TLC: R$_f$ 0.35 (ethyl acetate-methanol, 3:1); R$_f$ 0.05 (ethyl acetate).

PMR data (D$_2$O free base): δ 2.10 (t, 1 H, H-2ax), 2.65 (m, 1 H, H-2eq), 4.45 (bm, 5 H, H-1,3,4,5,6), 4.50 (d, 4 H, 2-N—C$\underline{H}_2$—Ph), 4.93 (s, 2 H, —O—C$\underline{H}_2$—Ph), 7.55 (d, 15 H, 3 Ph).

Analysis: Calcd. for: C$_{27}$H$_{34}$N$_2$O$_3$Cl$_2$: C, 64.15; H, 6.78; N, 5.54. Found: C, 64.22; N, 6.84; N, 5.48%.

EXAMPLE LXVIII

To an ice-cold solution of 2-deoxy-1-N,3-N,5-O-tribenzylstreptamine hydrochloride (505 mg, 1 mmol) and sodium carbonate (0.5 g) in water (25 ml) and acetone (50 ml), methyl chloroformate (0.25 ml, 3.2 mmol) in acetone (15 ml) was added dropwise, with stirring. After 5 h, the inorganic salts were removed by filtration. The solution was concentrated, water was added and the insoluble residue was filtered, washed with water and dried. It was recrystallized from hot benzene to give 400 mg (73%) of pure 2-deoxy-1,3-di-N-methoxycarbonyl-1-N,3-N,5-O-tribenzylstreptamine. M.p.: 185.5°–186.5°.

TLC: R$_f$ 0.62 (ethyl acetate); R$_f$ 0.37 (chloroform-ethyl acetate, 1:1).

IR: ν$_{max}^{CHCl_3}$ 3420 (OH), 1690 (NCOOMe), 1600 (Ph) cm$^{-1}$.

PMR data (CDCl$_3$): δ 1.55 (m, 1 H, H-2ax), 1.80 (m, 1 H-2eq), 2.60 (m, 2 H, 2 OH), 3.55 (bm, 1 H, H-1,3,4,5,6), 3.66 (s, 6 H, 2 NCOOMe) 4.37 (s, 4 H, 2 N—C$\underline{H}_2$Ph), 4.82 (s, 2 H, —O—C$\underline{H}_2$—Ph), 7.25 (m, 15 H, 3 Ph).

Analysis: Calcd. for: C$_{31}$H$_{36}$N$_2$O$_7$: C, 67.86; H, 6.61; N, 5.10. Found: C, 67.70; H, 6.71; N, 5.03%.

EXAMPLE LXIX

2-Deoxy-1,3-di-N-benzylstreptamine-1,6:3,4-dicarbamate (1.182 g, 3 mmol) and sodium hydride (0.2 g, 5 mmol, 60% oil dispersed) in N,N-dimethylformamide (15 ml) was stirred at 0° for 0.5 h. Chloromethylmethyl sulphide (0.5 ml) was added dropwise at 0°, and the mixture was stirred at 22° for 14 h, then dropped into ice-water containing sodium bicarbonate, pH∼7–7.5. The precipitate was filtered off, washed with water, dried and purified by silica gel column chromatography using benzene as eluant. 2Deoxy-1,3-di-N-benzyl-5-O-methylthiomethylstreptamine-1,6:3,4-dicarbamate (0.983 g, 72%) thus obtained was recrystallized from ethanol. M.p.: 160°–162°.

TLC: $R_f$ 0.5 (chloroform-ethyl acetate, 1:1).

IR: $\nu_{max}^{CDCl_3}$: 1760 (NCOO), 1500 (Ph) cm$^{-1}$.

PMR data (CDCl$_3$): δ 1.28 (m, 1 H, $J_{2ax, 2eq}$=11 Hz, H-2ax), 1.93 (dt, 1 H, $J_{2ax, 2eq}$=11 Hz, $J_{2eq,1}$=$J_{2eq,3}$=3.5 Hz, H-2eq), 2.16 (s, 3 H, S-Me), 3.02 (m, 2 H, $J_{1,6}$=$J_{3,4}$=11 Hz, H-1,3), 3.90 (q, 2 H, $J_{4,5}$=$J_{6,5}$=9 Hz, H-4,6), 4.38 (q, 4 H, 2CH$_2$Ph), 4.42 (t, 1 H, $J_{5,4}$=$J_{5,6}$=9 Hz, H-5) 4.87 (s, 2 H, —OCH$_2$S), 7.30 (m, 10 H, 2 Ph).

EXAMPLE LXX

A suspension of 2-deoxy-1,3-di-N-benzyl-5-O-methylthiomethylstreptamine-1,6:3,4-dicarbamate (0.34 g, 1.85 mmol) in 1N sodium methoxide in methanol (25 ml) was boiled under reflux for 0.5 h. Water (25 ml) was then added and boiling under reflux was continued for 24 h. The solution was neutralized with CO$_2$, concentrated, and the residue dissolved in aqueous acetone (2:1, 15 ml). This solution was cooled at 0°, sodium carbonate (1 g) was added with stirring, followed by the dropwise addition of methyl chloroformate (0.8 ml) in acetone (2 ml). The stirring was continued for 4 h, the solvents were removed in vacuo, and the precipitate obtained after the addition of water was collected, washed with water and dried (0.956 g). The solid was recrystallized from benzene to give 0.88 g (92%) of crystalline 2-deoxy-1,3-di-N-benzyl-1,3-di-N-methoxycarbonyl-5-O-methylthiomethylstreptamine. M.p.: 173.5°–174.5°.

TLC: $R_f$ 0.42 (ethyl acetate).

IR: $\nu_{max}^{CHCl_3}$: 3420 (OH), 1685 (NCOOMe), 1600 (Ph) cm$^{-1}$.

PMR data (CDCl$_3$): δ 1.40–1.90 (m, 2 H, H-2ax, 2eq), 2.20 (s, 3 H, SCH$_3$), 2.72 (b, 2 H, 2 OH), 3.20–4.00 (m, 11 H, skeleton protons), 3.70 (s, 6 H, 2 COOMe), 4.40 (s, 4 H, 2 CH$_2$Ph), 4.90 (s, 2 H, OCH$_2$S), 7.23 (m, 10 H, 2 Ph).

EXAMPLE LXXI

A mixture of 1,3-di-N-benzyl-2,5-dideoxy-1,3-di-N-methoxycarbonylstreptamine (0.51 g, 1.15 mmol) and tri-O-acetyl-D-glucal (0.78 g, 2.8 mmol) in dry benzene (20 ml), boron trifluoride etherate (0.02 ml) was stirred for 0.5 h. Triethylamine (1 ml) was added, and the mixture was washed with water, dried and concentrated. The syrupy residue showed three components on TLC (ethyl acetate): (a) $R_f$ 0.57 (major), (b) $R_f$ 0.40 and (c) $R_f$ 0.28. These were separated by silica gel column chromatography using chloroform-benzene mixtures as eluant. Component (a) was a low melting solid (35°-37° from ether-petroleum ether) and was identified as 4,6-di-O-(4,6-di-O-acetyl-2,3-dideoxy-α-D-erythro-hex-2-enopyranosyl)-1,3-di-N-benzyl-2,5-dideoxy-1,3-di-N-methoxycarbonylstreptamine (0.75 g, 75.3%).

TLC: $R_f$ 0.57 (ethyl acetate); $R_f$ 0.43 (benzene-ethyl acetate, 1:1).

IR: $\nu_{max}^{CHCl_3}$: 1735 (OAc), 1690 (NCOOMe), 1600 (Ph) cm$^{-1}$.

PMR data (CDCl$_3$): δ 1.40 (m, 3 H, H-2ax, 2eq, 5 ax), 2.07 (q, 42 H, 4 OAc), 3.67 (m, 6 H, 2 NCOOMe), 4.25 (bm, 14 H, 4 CH$_2$Ph, H 1,3,4,6,5',5'',6',6'',6'',6''), 5.20 (m, 2 H, H-1'α,1''α), 5.36 (m, 2 H, H-4',4''), 5.77 (m, 4 H, H-2',2'',3',3''), 7.20 (m, 10 H, 2 Ph).

Analysis: Calcd. for: C$_{44}$H$_{54}$N$_2$O$_{16}$: C, 60.96; H, 6.21; N, 3.23. Found: C, 61.10; H, 6.41; N, 3.10%.

EXAMPLE LXXII 1,3-di-N-benzyl-2,5-dideoxy-1,3-di-N-methoxycarbonylstreptamine (442 mg, 1 mmol) and tri-O-acetyl-D-glucal (820 mg, 3 mmol) in benzene (25 ml) were treated with boron trifluoride etherate (0.1 ml) for 0.5 h at room temperature with stirring. Triethylamine (0.5 ml) was added and the reaction mixture was washed with water, dried and concentrated to yield a syrup (1.2 g). This was dissolved in methanol (20 ml) and hydrogenated over 10% palladium-on-harcoal (0.2 g) at atmospheric pressure for 2 h. After filtering the catalyst the reaction mixture was concentrated to give a syrup (1.13 g) which was purified by silica gel column chromatography using benzene-chloroform (1:2) as eluant. Three components were separated in this way: (TLC: benzene-ethyl acetate, 1:1):

(a) main component, $R_f$=0.30 (trisaccharide)

(b) minor component, $R_f$=0.09 (disaccharide)

(c) minor component, $R_f$=0.05 (disaccharide).

The main component (a) was recrystallized from ether-petroleum ether 60°–80° to give 560 mg (65%) of pure 4,6-di-O-(4,6-di-O-acetyl-2,3-dideoxy-α-D-erythro-hexopyranosyl)-1,3-di-N-benzyl-2,5-dideoxy-1,3-di-N-methoxycarbonylstreptamine. M.p.: 63°–65°. $[α]_D^{24}$+71.5° (c 0.7, chloroform).

TLC: $R_f$ 0.65 (ethyl acetate); $R_f$ 0.3 (benzene-ethyl acetate, 1:1); $R_f$ 0.2 (chloroform-ethyl acetate, 3:1).

PMR data (CDCl$_3$, 90°): δ 1.10–1.80 (series of multiplets 12 H, H-2,2,2',2',2'',2'',3',3',3'',3'',5,5), 1.95 (3 s, 12 H, 4 OAc), 3.62 (2 s, 6 H, 2 NCOOMe), 3.70–4.45 (series of multiplets, 2-CH$_2$Ph, H-1,3,4,4',4'',5',5'',6,6',6',6'',6''), 4.60 (m, 1 H, H-1''α), 4.91 (m, 1 H, H-1'α), 7.13 (m, 10 H, 2 Ph).

Analysis: Calcd. for: C$_{44}$H$_{58}$N$_2$O$_{16}$: C, 60.68; H, 6.71; N, 3.21. Found: C, 60.81; H, 6.52; N, 3.05%.

EXAMPLE LXXIII

Component (b) ($R_f$ 0.15, [benzene-ethyl acetate, 1:1]) separated from the chromatographic column in the previous Example was identified as pure 6-O-(4,6-di-O-acetyl-2,3-dideoxy-α-D-erythro-hexopyranosyl)-1,3-di-N-benzyl-2,5-dideoxy-1,3-di-N-methoxycarbonylstreptamine, $[α]_D^{25}$+32° (c 0.7, chloroform).

TLC: $R_f$ 0.45 (ethyl acetate).

IR: $\nu_{max}^{CHCl_3}$ 3440 (—OH), 1725 (—OAc), 1680 (—NCOOMe), 1487 (—Ph), 1235 (C—O), 1037 (—O—glycoside) cm$^{-1}$.

PMR data (CDCl$_3$): δ 1.25 (m, 1 H, H-2ax), 1.65 (m, 4 H, H-2',2',3',3'), 2.02 (s, 6 H, 2 OAc), 2.40 (m, 1 H, H-5eq), 3.68 (2 s, 6 H, 2 NCOOMe), 4.10 (m, 4 H, 2 CH$_2$Ph), 4.65 (m, 1 H, H-1'α), 7.24 (m, 10 H, 2 Ph).

Analysis: Calcd. for: C$_{34}$H$_{44}$N$_2$O$_{11}$: C, 62.18; H, 6.75; N, 4.26. Found: C, 62.05; H, 6.60; N, 4.33%.

EXAMPLE LXXIV

Component (c) (TLC: $R_f$ 0.10, benzene-ethyl acetate, 1:1) separated from the chromatographic column in Example LXII was identified as pure, glassy, 4-O-(4,6-di-)-acetyl-2,3-dideoxy-α-D-erythro-hexopyranosyl)-1,3-di-N-benzyl-2,5-dideoxy-dimethoxycarbonyl-2,5-dideoxystreptamine. $[α]_D^{25}$+75.5° (c 0.6, chloroform).

TCL: $R_f$ 0.35 (ethyl acetate).

IR: $\nu_{max}^{CHCl_3}$ 3440 (—OH), 1725 (—OAc), 1680 (—NCOO), 1487 (—Ph), 1240 (C—O), 1027 (—O—glycoside).

PMR data (CDCl$_3$): δ 1.25 (m, 1 H, H-2ax), 1.70–1.90 (m, 6 H, H-2',2',3',3',2eq, 5ax), 2.02 (s, 3 H, OAc), 2.06 (s, 3 H, OAc), 3.68 (s, 6H, 2 NCOOMe), 3.40–3.90 (bm, 4 H, H-1,3,4,6), 4.00–4.80 (m, 10 H, 2 C$\underline{H}_2$Ph and skeleton protons), 4.94 (m, 1 H, H-1'α), 7.23 (m, 10 H, 2 Ph).

Analysis: Calcd. for: C$_{34}$H$_{44}$N$_2$O$_{11}$: C, 62.18; H, 6.75; N, 4.26. Found: C, 62.28; H, 6.87; N, 4.20%.

EXAMPLE LXXV 6O-(4,6-Di-O-acetyl-2,3-dideoxy-α-D-erythro-hexopyranosyl)-1,3-di-N-benzyl-2,5-dideoxy-1,3-di-N-methoxycarbonylstreptamine 65 mg, 0.1 mmol) in methanol (2 ml) was deacetylated for 12 h with sodium methoxide (10 mg). The mixture was neutralized (CO$_2$) and concentrated. The chloroformic extracts of the residue were evaporated and the solid was recrystallized from chloroform-ether to yield 54 mg (95%) of pure 6-O-(2,3-dideoxy-α-Derythro-hexopyranosyl)-1,3-di-N-benzyl-2,5-dideoxy-1,3-di-N-methoxycarbonylstreptamine, m.p.: 87°. $[α]_D^{21}$ +29° (c 0.9, chloroform).

IR: $ν_{max}^{CDCl_3}$ 3400 (OH), 1685 (NCOOMe), 1500 (Ph), cm$^{-1}$.

PMR data (CDCl$_3$, 95°): δ1.20–1.90 (m, 7 H, H-2ax, 2eq, 5ax, 2',2', 3',3'), 2.25–2.60 (bm, 4 H, H-5eq, 3 OH), 3.70 (m, 6 H, 2 NCOOC$\underline{H}_3$), 4.40 (m, 4 H, 2 C$\underline{H}_2$—Ph), 4.63 (m, 1 H, H-1"α), 7.23 (m, 10 H, Ph).

Analysis: Calcd. for C$_{30}$H$_{40}$N$_2$O$_9$: C, 62.92; H, 7.04; N, 4.89. Found: C, 63.02; H, 7.16; N, 5.04%.

EXAMPLE LXXVI

4-O-(4,6-Di-O-acetyl-2,3-dideoxy-α-D-erythro-hexopyranosyl)-1,3-di-N-benzyl-1,3-di-N-methoxycarbonyl-2,5-dideoxystreptamine (50 mg, 0.076 mm l) in methanol (2 ml) was catalytically deacetylated with 0.2 ml of methanolic 0.1 N sodium methoxide for 12 h. The mixture was neutralized with solid CO$_2$ and concentrated to give a solid which was extracted with chloroform. The organic extracts were filtered and concentrated, the residue was recrystallized from chloroform-ether to yield 39 mg (90%) of 4-O-(2,3-dideoxy-α-D-erythro-hexopyranosyl)-1,3-di-N-benzyl-2,5-dideoxy-1,3-di-N-methoxycarbonylstreptamine. M.p.: 95° (sinters). $[α]_D^{21}$ +58°)c 0.5, chloroform).

TLC: $R_f$ 0.20 (benzene-methanol, 3:1); $R_f$ 0.20 (ethyl acetate-ethanol, 8:1).

IR: $ν_{max}^{CDCl_3}$ 3400 (OH), 1685 (NCOO), 1500 (Ph), 1250, 1125, 1070, 1030, 700 cm$^{-1}$.

PMR data (CDCl$_3$, 100°): δ 1.20–1.65 (m, 3 H, H-2ax, 2eq, 5ax.), 1.75 (m, 4 H, H-2',2',3',3')2.10 (bb, 3 H, 3 OH), 2.40 (m, 1 H, H-5eq), 3.70 (2 s, 6 H, 2 COOme), 4.37 (m, 4 H, 2 CH$_2$—Ph), 4.89 (m, 1 H, H-1'α), 7.23 (m, 10 H, 2 Ph).

Analysis: Calcd. for C$_{30}$H$_{40}$N$_2$O$_9$: C, 62.92; H, 4.04; N, 4.89. Found: C, 62.84; H, 6.08; N, 4.73%.

EXAMPLE LXXVII 4,6-Di-O-(4,8-di-O-acetyl-2,3-dideoxy-α-D-erythro-hexopyranosyl)-1,3-di-N-benzyl-2,5-dideoxy-1,3-di-N-methoxycarbonylstreptamine (360 mg, 0.41 mmol) in methanol (10 ml) was treated with sodium methoxide (20 mg) for 12 h. The mixture was neutralized (CO$_2$) and concentrated to give a solid which was extracted with chloroform. The organic extracts were evaporated and the residue was recrystallized from chloroform-ether to yield pure 4,6-di-O-(2,3-dideoxy-α-D-erythro-hexopyranosyl)-1,3-di-N-benzyl-2,5-dideoxy-1,3-di-N-methoxycarbonylstreptamine (280 mg, 96%), M.p.: 72°. $[α]_D^{25}$ +66° (c 1.1, chloroform).

TLC: $R_f$ 0.12 (ethyl acetate-ethanol, 8:1); $R_f$ 0.50 (ethyl acetate-ethanol, 2:1).

IR: $ν_{max}^{CHCl_3}$ 3400 (OH), 1675 (NCOOMe), 1595 (Ph) cm$^{-1}$.

Analysis: Calcd. for: C$_{36}$H$_{50}$N$_2$O$_{12}$: C, 61.52; H, 7.17; N, 3.98. Found: C, 61.64; H, 7.02; N, 4.02%.

EXAMPLE LXXVIII

A mixture of 4,6-di-O-(2,3-dideoxy-α-D-erythro-hexopyranosyl)-1,3-di-N-benzyl-2,5-dideoxy-1,3-di-N-methoxycarbonylstreptamine (0.2 g, 0.28 mmol), 90% hydrazine hydrate (2 ml) and ethanol (1 ml) was heated under reflux for 24 h in an oil bath at 130°. The solvent were removed in vacuo and the residue was purified by chromatography (silica gel/chloroform-methanol mixtures as eluant) to give pure, glassy 4,6-di-O-(2,3-dideoxy-α-D-erythro-hexopyranosyl)-1,3-di-N-benzyl-2,5-dideoxystreptamine (0.147 g, 90%). $[α]_D^{25}$ +93.5° (c 1.0, methanol).

TLC: $R_f$ 0.50 (chloroform-methanol-ammonia, 100:30:5), ninhydrin positive.

PMR data (D$_2$O): δ 1.95 (bm, 12 H, H-2,2,2',2',2",2",3',3',3",3",5,5), 3.70 (bm, 16 H, skeleton protons and 2 C$\underline{H}_2$—Ph), 4.98 (m, 2 H, (H-1'α and H-1"α), 7.22 (m, 10 H, 2 Ph).

Analysis: Calcd. for: C$_{32}$H$_{46}$N$_2$O$_8$: C, 65.50; H, 7.90; N, 4.77. Found: C, 65.65; H, 8.10; N, 4.85%.

EXAMPLE LXXIX

A mixture of 4,6-di-O-(4,6-di-O-acetyl-2,3-dideoxy-α-D-erythro-hexopyranosyl)-1,3-di-N-benzyl 2,5-dideoxy-1,3-di-N-methoxycarbonylstreptamine (87 mg, 0.1 mmol), 90% hydrazine hydrate (1 ml) and ethanol (1 ml) was heated under reflux for 24 h in an oil bath (130°). The solvents were evaporated in vacuo and the glassy residue was purified by chromatography on silica gel, using chloroform-methanol mixtures as eluant. 4,6-Di-O-(2,3-dideoxy-α-D-erythro-hexopyranosyl)-1,3-di-N-benzyl-2,5-dideoxystreptamine was obtained pure as a glassy solid (55 mg, 94%). $[α]_D^{25}$ +95° (c 1.0 methanol).

TLC: $R_f$ 0.5 (chloroform-methanol-ammonia, 100:30:5).

The PMR spectrum (D$_2$O) of this compound is identical with that of the product isolated in the previous example.

Analysis: Calcd. for: C$_{32}$H$_{46}$N$_2$O$_8$: C, 65.50; H, 7.90; N, 4.77. Found: C, 65.40; H, 7.95; N, 4.68%.

EXAMPLE LXXX 4,6-Di-O-(2,3-dideoxy-α-D-erythro-hexopyranosyl)-1,3-di-N-benzyl-2,5-dideoxystreptamine (117 mg, 0.2 mmol) in methanol (20 ml) was hydrogenated overnight at 2 atmos. over 10% palladium-on-charcoal catalyst (100 mg). After filtering and washing the catalyst, the combined liquids were concentrated to give pure 4,6-di-O-(2,3-dideoxy-α-D-erythro-hexopyranosyl)-2,5-dideoxystreptamine as a white glassy solid (74.8 mg, 92%). $[α]_D^{25}$ +109.5° (c 0.6, methanol).

TLC: $R_f$ 0.06 (chloroform-methanol-ammonia, 100:30:5); $R_f$ 0.32 (methanol-ammonia, 8:1); $R_f$ 0.55 (Whatman No. 1 chromatographic paper/propanol-pyridine-acetic acid-water, 15:10:3:12), ninhydrin positive.

Mass spectrum: M/e 407: calculated M+: 407.

Analysis: Calcd. for: C$_{18}$H$_{34}$N$_2$O$_8$: C, 53.18; H, 8.43; N, 6.89. Found: C, 53.02; H, 8.35; N, 7.01%.

EXAMPLE LXXXI 4,6-Di-O-(4,6-di-O-acetyl-2,3-dideoxy-α-D-erythro-hexopyranosyl)-1,3-di-N-benzyl-2,5-dideoxy-1,3-di-N-methoxycarbonylstreptamine (866 mg, 1 mmol) dissolved in a 1:1 mixture of 90% hydrazine hydrate and ethanol (5 ml) was heated under reflux for 24 h (130° oil bath). The mixture was then cooled, 10% palladium-on-charcoal (150 mg) and ethanol (25 ml) were added and the suspension was hydrogenated under 2 atm. pressure for 8 h. The catalyst was filtered and washed with methanolic ammonia, all the organic liquids were combined, evaporated to dryness and the residue was extracted with methanol (20 ml) and again evaporated. The glassy residue was purified by chromatography on silica gel with methanol-ammonia (8:1) as eluant to give 370 mg (91%) of pure 4,6-di-O-(2,3-dideoxy-α-D-erythro-hexopyranosyl)-2,5-dideoxystreptamine as an amorphous solid. $[\alpha]_D^{25} +110°$ (c, 1, methanol).

TLC: $R_f$ 0.32 (methanol-ammonia, 8:1); $R_f$ 0.55 (Whatman No. 1 chromatographic paper/propanol-pyridine-acetic acid-water, 15:10:3:12), ninhydrin positive.

Analysis: Calcd. for: $C_{18}H_{34}N_2O_8$: C, 53.18; H, 8.43; N, 6.89. Found: C, 53.40; H, 8.20; N, 6.75%.

EXAMPLE LXXXII

A mixture of 5-O-Allyl-2-deoxy-1,3-di-N-benzyl-1,3-di-N-methoxycarbonylstreptamine (0.1 g, 0.2 mmol) and tri-O-acetyl-D-glucal (0.163 g, 0.6 mmol) in dry benzene (10 ml) was treated with boron trifluoride etherate (0.05 ml) for 0.5 h at 22°. Triethylamine was added (0.3 ml) and the solution was washed with water, dried and concentrated. The resulting syrup was fractionated by preparative TLC (chloroform-ethyl acetate, 4:1). The fraction with $R_f$ 0.35 was isolated (40 mg) and identified as amorphous 5-O-allyl-4,6-di-O-(4,6-di-O-acetyl-2,3-dideoxy-α-D-erythro-hex-2-enopyranosyl)-2-deoxy-1,3-di-N-benzyl-1,3-di-N-methoxycarbonyl-streptamine. $[\alpha]_D^{24} +82.5°$ (c, 0.66, chloroform).

TLC: $R_f$ 0.35 (chloroform-ethyl acetate, 4:1); $R_f$ 0.35 (benzene-ethyl acetate, 1:1).

IR: $\nu_{max}^{CHCl_3}$ 1735 (OAc), 1690 (NCOOMe), 1490 (Ph) $cm^{-1}$.

PMR data (CDCl$_3$, 110°): δ 1.10–1.40 (m, 2 H, H-2ax, 2eq), 2.03 (s, 12 H, 4 OAc), 3.30 (m, 2 H, H-1,3), 3.68 (2 s, 6 H, 2 NCOOMe), 3.80–4.80 (m, skeleton protons and C$\underline{H}_2$Ph), 5.05 (m, 1 H, H-1'α), 5.10–5.50 (m, 4 H, H-4",4" and C=CH$_2$, allyl), 5.80 (m, 5 H, H-2',2",3',3" and C$\underline{H}$=C allyl), 7.15 (m, 10 H, 2 Ph).

Analysis: Calcd. for: $C_{47}H_{58}N_2O_{17}$: C, 61.16; H, 6.33; N, 3.03. Found: C, 61.30; H, 6.40; N, 3.15%.

EXAMPLE LXXXIII

A mixture of 2-deoxy-1,3-di-N-methoxycarbonyl-1N, 3N, 5-O-tribenzylstreptamine (0.7 g, 1.27 mmol) and tri-O-acetyl-D-glucal (1.04 g, 3.8 mmol) in dry benzene (100 ml) was treated with boron trifluoride etherate (0.1 ml) for 0.5 h at 22°. Triethylamine (0.5 ml) was added, the mixture was washed with water and concentrated. The syrup (1.93 g) was deacetylated in methanol (20 ml) with sodium methoxide (50 mg) for 12 h at 22°. The neutralized solution (CO$_2$) was concentrated and the residue was extracted. The extracts were concentrated and the syrup thus obtained was purified by silica gel column chromatography using benzene-chloroform and benzene-methanol mixtures as eluants. The main fraction was precipitated from chloroform solution with petroleum 40°–60° as an amorphous solid (376 mg, 45%) and was identified as pure 4,6-di-O-(2,3-dideoxy-α-D-erythro-hex-2-enopyranosyl)-2-deoxy-1,3-di-N-methoxycarbonyl-1-N,3-N,5-O-tribenzylstreptamine. M.p.: 105° (sinters). $[\alpha]_D^{22} +37°$ (c 0.43, chloroform).

TLC: $R_f$ 0.27 (benzene-methanol, 4:1); $R_f$ 0.43 (ethyl acetate-ethanol, 10:1), $R_f$ 0.08 (ethyl acetate).

IR: $\nu_{max}^{CHCl_3}$ 3420 (OH), 1690 (NCOOMe), 1600 (Ph), 1580 (Ph) $cm^{-1}$.

PMR data (CDCl$_3$, 95°): δ 1.30 (m, 2 H, H-2ax, 2eq), 2.10 (b.b, 4 H, 4 OH), 3.70 (m, 6 H, 2 NCOOMe), 5.40–5.95 (m, 5 H, H-1',2',3',2",3"), 7.20 (m, 15 H, 3 Ph).

Analysis: Calcd. for: $C_{43}H_{52}N_2O_{13}$: C, 64.16; H, 6.51; N, 3.48. Found: C, 64.28; H, 6.70; N, 3.56%.

EXAMPLE LXXXIV

A solution of 4,6-di-O-(2,3-dideoxy-α-D-erythro-hex-2-enopyranosyl)-2-deoxy-1,3-di-N-methoxycarbonyl-1-N, 3-N, 5-O-tribenzylstreptamine (0.3 g, 0.35 mmol) in methanol (20 ml) was hydrogenated over 10% palladium-on-charcoal (50 mg) at atmospheric pressure for 2 h. The filtered solution was concentrated and the residue was purified by silica gel column chromatography (benzene-methanol mixtures as eluant) and by precipitation from an ethereal solution with petroleum 40°–60°. The amorphous solid (0.25 g, 83%) was identified as 4,6-di-O-(2,3-dideoxy-α-D-erythro-hexopyranosyl)-2-deoxy-1,3-di-N-methoxycarbonyl-1-N,3-N-5-O-tribenzylstreptamine, M.p.: 105° (sinters).

IR: $\nu_{max}^{CHCl_3}$: 3420 (OH), 1690 (NCOOMe), 1605 (Ph), 1590 (Ph), $cm^{-1}$.

PMR data (CDCl$_3$, 95°); δ 1.20–1.80 (m, 10 H, H-2,2,2',2',2",2",3',3',3",3"), 3.67 (2 s, 6 H, 2 NCOOMe), 4.32 (m, 4 H, 2 NC$\underline{H}_2$Ph), 4.85 (m, 1H, H-1"α), 4.88 (m, 2 H, —OC$\underline{H}_2$Ph), 5.27 (m, 1 H, H-1'α), 7.20 (m, 15 H, 3 Ph).

Analysis: Calcd. for: $C_{43}H_{56}N_2O_{13}$: C, 63.84; H, 6.98; N, 3.46. Found: C, 63.97; H, 7.03; N, 3.50%.

EXAMPLE LXXXV

Carbon tetrachloride (0.2 ml) and hexamethylphosphorus triamide (0.2 ml) were added to a solution of 4,6-di-O-(2,3-dideoxy-α-D-erythro-hexopyranosyl)-1,3-di-N-benzyl-2,5-dideoxy-1,3-di-N-methoxycarbonyl-streptamine (0.351 g, 0.5 mmol) in dry dimethylformamide (2 ml). The mixture was stirred at −45° for 1 h. Sodium azide (0.26 g, 4 mmol) was added and the solution was stirred at 80° for 18 h. It was then poured into ice-water and extracted with ether. The extracts were washed with water, dried and concentrated to give a glassy product (0.373 g) which was purified by chromatography on silica gel (chloroform). The eluted product (0.26 g, 70%) was pure, glassy 4,6-di-O-(6-azido-2,3,6-trideoxy-α-D-erythro-hexopyranosyl)-1,3-di-N-benzyl-2,5-dideoxy-1,3-di-N-methoxycarbonylstreptamine. $[\alpha]_D^{24.4} +44.7°$ (c, 0.78, chloroform).

TLC: $R_f$ 0.11 (benzene-ethyl acetate, 1:1); $R_f$ 0.50 (ethyl acetate).

PMR data (CDCl$_3$, 80°): δ 1.20–1.80 (m, 11 H, H-2,2,2',2',2",2",3',3',3",3",5ax), 1.98 (s, 2 H, 2)H), 2.65 (m, 1 H, H-5eq), 3.46 (m, 4 H, H-6',6',6",6"), 3.66 (2 s, 6 H, 2 NCOOMe), 4.30 (m, 4 H, 2 C$\underline{H}_2$—Ph), 4.59 (m, 1 H, H-1"α), 4.96 (m, 1 H, H-1'α), 7.17 (m, 10 H, 2 Ph).

Analysis: Calc. for $C_{36}H_{48}N_8O_{10}$: C, 57.43; H, 6.42; N, 14.88. Found: C, 57.30; H, 6.50; N, 14.74%.

EXAMPLE LXXXVI

A mixture of 4,6-di-O-(2,3-dideoxy-α-D-erythro-hexopyranosyl)-1,3-di-N-benzyl-2,5-dideoxy-1,3-di-N-methoxycarbonylstreptamine (0.5 g, 0.71 mmol) and toluene-p-sulphonyl chloride (0.3 g, 1.56 mmol) in dry pyridine (5 ml) was stirred at −20° for 1 h. and stored at 22° for 16 h. The mixture was poured into ice and extracted with chloroform. The extracts were washed with water, dried and concentrated to give a glassy residue. Purification of this material by chromatography (silica gel-ethyl acetate) gave amorphous, pure 4,6-di-O-(6-O-toluene-p-sulphonyl-2,3-dideoxy-α-D-erythro-hexopyranosyl)-1,3-di-N-benzyl-2,5-dideoxy-1,3-di-N-methoxycarbonylstreptamine, (0.503 g, 70%). M.p.: 75°–80°. $[\alpha]_D^{24} + 43.6°$)c 0.53, chloroform).

TLC: $R_f$ 0.57 (ethyl acetate).

IR: $\nu_{max}^{CHCl_3}$ 3420 (OH), 1690 (NCOOMe), 1600 (Ph), 1180 (O SO$_2$) cm$^{-1}$.

PMR data (CDCl$_3$,—D$_2$O): δ 1.25 (m, 1 H, H-2ax), 1.40–1.95 (m, 10 H, H-2eq, 2',2',2",2",3',3',3",3",5ax), 2.42 (2 s, 6 H, C$\underline{H}_3$—Ph), 3.63 (s, 6 H, 2 NCOOMe), 4.18 (m, 4 H, 2 C$\underline{H}_2$—Ph), 4.93 (m, 1 H, H-1'α), 7.18 (m, 10 H, 2 Ph), 7.32 and 7.78 (2 m, 8 H, 2-Ph-, tosyl).

Analysis: Calcd. for: C$_{50}$H$_{62}$N$_2$O$_{16}$S$_2$: C, 59.40; H, 6.18; N, 2.77; S, 6.33. Found: C, 59.60; H, 6.20; N, 2.95; S, 6.43.

EXAMPLE LXXXVII

A solution of 4,6-di-O-(6-O-toluene-p-sulphonyl-2-3-dideoxy-α-D-erythro-hexopyranosyl)-1,3-di-N-benzyl-2,5-dideoxy-1,3-di-N-methoxycarbonylstreptamine (30 mg, 0.03 mmol) in dry pyridine (0.5 ml) was treated with acetic anhydride (0.05 ml, 0.5 mmol) at 22° for 12 h. After the addition of water (0.03 ml) the mixture was concentrated to give a residue which was triturated with water and recrystallized from ethanol-water (23 mg, 71%). Pure 4,6-di-O-(4-O-acetyl-6-O-toluene-p-sulphonyl-2,3-dideoxy-α-D-erythro-hexopyranosyl-1,3-di-N-benzyl-2,5-dideoxy-1,3-di-N-methoxycarbonylstreptamine thus obtained had an m.p. of 85°–88°.

TLC: $R_f$ 0.68 (benzene-ethyl acetate, 1:2); $R_f$ 0.50 (chloroform).

PMR data (CDCl$_3$): δ 1.25 (m, 1 H, H-2ax), 1.50–2.00 (m, 10 H, H-2eq, 2',2',2",2",3',3',3",3", and 5ax), 1.95 (2 s, 6 H, 2 OAc), 2.43 (2 s, 6 H, CH$_3$-tosyl groups), 2.65 (m, 1 H, H-5eq), 3.67 (2 s, 6 H, 2 NCOOMe), 3.90–4.70 (b.band, the remaining protons), 5.02 (m, 1 H, H-1'α), 7.20 (m, 10 H, 2 Ph), 7.32 and 7.78 (2 m, 8 H, 2-Ph-, tosyl).

Analysis: Calcd. for: C$_{54}$H$_{66}$N$_2$O$_{18}$S$_2$: C, 59.32; H, 6.06; N, 2.55; S, 5.83. Found: C, 59.20; H, 6.15; N, 2.70; S, 5.95%.

EXAMPLE LXXXVIII

A mixture of 4,6-di-O-(6,4-toluene-p-sulphonyl-α-D-erythro-hexopyranosyl)-1,3-di-N-benzyl-2,5-dideoxy-1,3-di-N-methoxycarbonylstreptamine (0.48 g, 0.475 mmol) and sodium azide (0.3 g, 4.6 mmol) in dry N,N-dimethylformamide (5 ml) was heated and stirred at 80° for 24 h. The mixture was poured into ice-water and extracted with ether. The extracts were washed with water, dried and concentrated to give a glassy residue (0.31 g, 87%) of pure 4,6-di-O (6 azido-2,3,6-trideoxy-α-D-erythro-hexopyranosyl)-1,3-di-N-benzyl-2,5-dideoxy-1,3-di-N-methoxycarbonylstreptamine. $[\alpha]_D^{24} + 45°$ (c 0.8, chloroform).

TLC: $R_f$ 0.11 (benzene-ethyl acetate, 1:1), $R_f$ 0.50 (ethyl acetate).

Analysis: Calcd. for: C$_{36}$H$_{48}$N$_8$O$_{10}$: C, 57.43; H, 6.42; N, 14.88. Found: C, 57.60; H, 6.50; N, 15.01%.

EXAMPLE LXXXIX

A mixture of 4,6-di-O-(6-azido-2,3,6-trideoxy-α-D-erythro-hexopyranosyl)-1,3-di-N-benzyl-2,5-dideoxy-1,3-di-N-methoxycarbonylstreptamine (0.2 g, 0.265 mmol), and 10% palladium-on-charcoal (0.05 g) in methanol (10 ml) was hydrogenated at atmospheric pressure for 20 h. The catalyst was filtered and washed with methanol containing ammonia and the organic liquids were concentrated to give a glassy material (0.192 g).

TLC: $R_f$ 0.25 (chloroform-methanol-ammonia, 100:30:5).

This product was heated under reflux (48 h) with ethanol—90% hydrazine hydrate (1:3, 2 ml), and the mixture was evaporated to dryness. The chloroformic extracts of the residue, on evaporation, yielded a glassy product (0.148 g, 95%) of pure 4,6-di-O-(6-amino-2,3,6-trideoxy-α-D-erythro-hexopyranosyl)-1,3-di-N-benzyl-2,5-dideoxystreptamine. $[\alpha]_D^{24} + 54.2°$ (c 0.166, methanol).

TLC: $R_f$ 0.10 (chloroform-ethanol-ammonia, 100:30:5); $R_f$ 0.55 (methanol-ammonia, 8:1).

Analysis: Calcd. for: C$_{32}$H$_{48}$N$_4$O$_6$: C, 65.73; H, 8.27; N, 9.58. Found: C, 65.91; H, 8.40; N, 9.63%.

EXAMPLE XC

A mixture of 4,6-di-O-(6-amino-2,3,6-trideoxy-α-D-erythro-hexopyranosyl)-1,3-di-N-benzyl-2,5-dideoxystreptamine (0.23 g, 0.39 mmol) and 10% palladium-on-charcoal (65 mg) in methanol (25 ml) was hydrogenated at atmospheric pressure for 16 h. Filtration of the catalyst and concentration of the clear solution gave a glassy residue of pure 4,6-di-O-(6-amino-2,3,6-trideoxy-α-D-erythro-hexopyranosyl)-2,5-dideoxystreptamine (0.16 g, 100%). $[\alpha]_D^{24} + 139.3°$ (c 0.37, methanol).

TLC: $R_f$ 0.48 (methanol-ammonia, 4:1) (cf Kanamycin A, $R_f$: 0.25); paper chromatography: $R_{glucosamine}$: 0.26 (n-butanol-pyridine-water-acetic acid, 6:4:3:1).

PMR data (D$_2$O): δ 1.10–2.20 (bm, H-2eq H-5ax 2 H-2', 2 H-2", 2 H-3' and 2 H-3"), 2.70–3.05 (m, 4 H, H-6',6',6",6"), 3.30–3.70 (m, 8 H, skeleton protons), 5.04 (m, 1 H, H-1"α), 5.06 (m, 1 H, H-1'α).

Analysis: Calcd. for C$_{18}$H$_{36}$N$_4$O$_6$: C, 53.45; H, 8.97; N, 13.85. Found: C, 53.16; H, 8.74; N, 13.90%.

EXAMPLE XCI

A mixture of 4,6-di-O-(6-azido-2,3,6-trideoxy-α-D-erythro-hexopyranosyl)-1,3-di-N-benzyl-2,5-dideoxy-1,3-di-N-methoxycarbonylstreptamine (0.7 g, 1 mmol), 90% hydrazine hydrate (3 ml), 10% palladium-on-charcoal (50 mg) and ethanol (2 ml) was heated under reflux for 6 h. After evaporating the mixture, ethanol (10 ml) and more palladium catalyst (50 mg) were added and the suspension was hydrogenated at 25°, 2 atoms. for 6 h. The mixture gave, upon filtration and concentration, a glassy residue (0.4 g, 99%) of pure 4,6-di-O-(6-amino-2,3,6-trideoxy-α-D-erythro-hexopyranosyl)-2,5-dideoxystreptamine. $[\alpha]_D^{24} + 139°$ (c 0.5, methanol)

TLC: $R_f$ 0.47 (methanol-amnonia, 4:1), (cf Kanamycin A, $R_f$: 0.25).

The PMR spectrum of this compound was identical with that of the product prepared in the previous Example.

Analysis: Calcd. for $C_{18}H_{36}N_4O_6$: C, 53.45; H, 8.97; N, 13.85. Found: C, 53.56; H, 9.09; N, 13.76%.

EXAMPLE XCII

A mixture of 4-O-acetyl-6-azido-2,3,6-trideoxy-D-erythro-hexopyranosyl bromide (0.56 g, 2 mmol) and 1,3-di-N-benzyl-2,5-dideoxy-1,3-di-N-methoxycarbonylstreptamine (0.443 g, 1 mmol), a mercuric cyanide (1.5 g), mercuric bromide (1.5 g), dry Amberlite IR-400 (Br⁻), (3 g) and Drierite (5 g) in nitromethane (15 ml) and benzene (10 ml), was shaken for 2 days in the dark. The mixture was filtered, the solids were washed with chloroform and all the combined organic liquids were concentrated to give a syrupy material which was purified by chromatography on silica gel using mixtures of chloroform-benzene as eluant.

4,6-Di-O-(4-O-acetyl-6-azido-2,3,6-trideoxy-α-D-erythro-hexopyranosyl)-1,3-di-N-benzyl-2,5-dideoxy-1,3-di-N-methoxycarbonylstreptamine (0.394 g, 47%) was obtained as a glassy material. $[\alpha]_D^{24.5} + 69°$ (c 0.55, chloroform).

TLC: $R_f$ 0.58 (benzene-ethyl acetate, 1:1).

PMR data (CDCl₃, 70°): δ1.30 (m, 10 H, H-2eq, 5ax, 2',2',2'',2'',3',3', 3'',3''), 2.00 (s, 6 H, 2 OAc), 2.65 (m, 1 H, H-5eq), 3.27 (m, 4 H, H-6',6',6'',6''), 3.67 (2 s, 6 H, 2 NCOOMe), 3.80–4.75 (broad band of multiplets, 12 H, skeleton protons), 5.01 (m, 1 H, H-1'α), 7.20 (m, 10 H, 2 Ph).

Analysis: Calcd. for $C_{40}H_{52}N_8O_{12}$: C, 57.40; H, 6.26; N, 13.39. Found: C, 57.62; H, 5.31; N, 13.45%.

EXAMPLE XCIII

Methylsulphonyl chloride (0.5 ml) was added to a solution of 4,6-di-O-(2,3-dideoxy-α-D-erythro-hexosyransoyl)-1,3-di-N-benzyl-2,5-dideoxy-1,3-di-N-methoxycarbonylstreptamine (0.5 g, 0.71 mmol) in dry pyridine (5 ml) and the mixture was stored at 22° for 12 h. Water (0.5 ml) was added and the mixture was poured into ice. The solid which separated was recrystallized from chloroform-ether to give pure 4,6-di-O-4,6-di-O-methylsulphonyl-2,3-dideoxy-α-D-erythro-hexopyranosyl) 1,3-di-N-benzyl-2,5-dideoxy-1,3-di-N-methoxycarbonylstreptamine (0.41 g, 50%). M.p.: 108°–110° (sinters at 100°). $[\alpha]_D^{27} + 60°$ (c 0.714, chlorform).

TLC: $R_f$ 0.25 (benzene-ethyl acetate, 1:1); $R_f$ 0.60 (ethyl acetate). PMR data (CDCl₃, 100°): δ 1.33 (m, 1 H, H-2ax), 1.65 (m, 2 H, H-2'',2''), 1.83 (m, 2 H, H-2',2'), 1.90–2.30 (bm, 4 H, H-3',3',3'',3''), 2.52 (m, 1 H, $J_{5ax, 5eq}$ =13 Hz, H-5eq), 3.02 (s, 12 H, 4 -SO₂Me), 3.37 (m, 2 H, H-1,3) 3.68 (s, 6 H, 2 NCOOMe), 4.00 (m, 2 H, H?4,6), 4.32 (m, 4 H, 2 CH₂Ph), 4.62 (m, 1 H, H-1''?), 5.00 (m, 1 H, H-1'α), 7.20 (m, 10 H, 2 Ph).

Analysis: Calcd. for: $C_{40}H_{58}N_2O_{20}S_4$: C, 47.34; H, 5.76; N, 2.76; S, 12.61. Found: C, 47.10; H, 5.81; N, 2.94; S, 12.79.

EXAMPLE XCIV

A mixture of 4,6-di-O-(4,6-di-O-methylsulphonyl)-b 2,3-dideoxy-α-D-erythro-hexopyranosyl)-1,3-di-N-benzyl-2,5,dideoxy,1,3-di-N-methoxycarbonylstreptamine (0.35 g, 0.34 mmol) and sodium axide (0.3 g, 4.6 mmol) in dry dimethylformamide (10 ml) was stirred at 90° for 25 h. The solvent was removed in vacuo, the residue was treated with ice-water and the precipitate thus obtained was filtered, washed (water) and dried. This product was purified by chromatography (silica gel, benzene-ethyl acetate) to give pure, amorphous 4,6-di-O-(4,6-di-azido-2,3,4,6-tetradeoxy-α-D-threo-hexopyranosyl)-1,3-di-N-benzyl-2,5-dideoxy-1,3-di-N-methoxycarbonylstreptamine (0.137 g, 49.5%). $[\alpha]_D^{23} + 13.4°$ (c 0.73, chloroform).

TLC: $R_f$ 0.70 (benzene -ethyl acetate, 1:2); $R_f$ 0.43 (choroform-ethyl acetate, 3:1).

PMR data (CDCl₃): δ 1.20–1.60 (bm, 5 H, H-2ax, 2',2',2'',2''), 1.70–2.10 (m, 6 H, H-2eq, 5ax, 3',3',3'',3''), 2.65 (m, 1 H, H-5eq), 3.00 3.50 (m, 6 H, H-4',4'',6',6'',6''), 3.67 (m, 6 H, 2 NCOOMe), 5.01 (m, 1 H, H-1'α), 7.20 (m, 10 H, 2 Ph).

Analysis: Calcd. for $C_{36}H_{46}N_{14}O_8$: C, 53.95; H, 5.76; N, 24.37. Found: C, 54.07; H, 5.64; N, 24.48%.

What I claim is:

1. A compound of the formula:

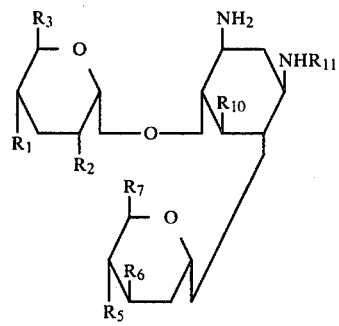

wherein
$R_1$ is H, F, OH or SH;
$R_2$ is H or NH₂;
$R_3$ is H or —CH₂—$R_4$ where $R_4$ is OH or NH₂; provided that when $R_1$ is H, $R_3$ is —CH₂—NH₂, and when $R_3$ is H or —CH₂—OH $R_1$ is NH₂;
$R_5$ is H, OH, SH or halogen;
$R_6$ is H, OH or NHR₈ where $R_8$ is H or Me;
$R_7$ is H or —CH₂—$R_9$ where $R_9$ is H, OH or NH₂; provided that when $R_6$ is H or OH, $R_7$ is —CH₂—NH₂ and when $R_8$ is H or —CH₂—OH, $R_6$ is NH $R_8$;
$R_{10}$ is H or OH; and
$R_{11}$ is H, CH₃ or —CO—CHOH—CH₂—CH₂NH₂; and the pharmaceutically acceptable acid addition salts thereof.

2. A compound as claimed in claim 1 wherein $R_1$ is H or OH, $R_2$ is H or NH₂, $R_3$ is CH₂—NH₂, $R_5$ is H or OH, $R_6$ is H, NH₂ or NHCH₃ and $R_7$ is —CH₂NH₂ or —CH₂OH.

3. A compound as claimed in claim 1 wherein $R_5$ is the same as $R_1$, $R_6$ is the same as $R_2$ and $R_7$ is the same as $R_3$.

4. A compound of the formula:

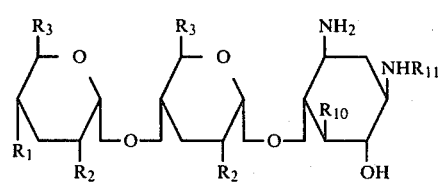

wherein
$R_1$ is H, F, OH or SH;
each $R_2$ is independently H or NH₂;
each $R_3$ is independently H or —CH₂—$R_4$ where $R_4$ is OH or NH₂;

provided that, in the terminal saccharide ring when the $R_2$ is H, the $R_3$ is $CH_2NH_2$ and when the $R_3$ is H or $CH_2OH$, the $R_2$ is $NH_2$;

$R_{10}$ is H or OH; and $R_{11}$ is H, $CH_3$ or $-CO-CHOH-CH_2-CH_2-NH_2$;

and the pharmaceutically acceptable acid addition salts thereof.

5. A compound as claimed in claim 4 wherein $R_1$ is H or OH, each $R_2$ is independently H or $NH_2$ and each $R_3$ is $CH_2NH_2$.

6. The compound of claim 4 where $R_1$ is OH, each $R_2$ is H, each of $R_3$ is $CH_2NH_2$, $R_{10}$ is OH and $R_{11}$ is H.

7. A compound of the formula:

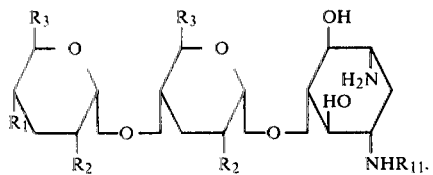

wherein
$R_1$ is H, F, OH or SH;
each $R_2$ is independently H or $NH_2$;
each $R_3$ is independently H or $-CH_2-R_4$ where $R_4$ is OH or $NH_2$;
provided that, in the terminal saccharide ring when the $R_2$ is H, the $R_3$ is $CH_2NH_2$ and when the $R_3$ is H or $CH_2OH$, the $R_2$ is $NH_2$; and
$R_{11}$ is H, $CH_3$ or $-CO-CHOH-CH_2-CH_2-NH_2$;
and the pharmaceutically acceptable acid addition salts thereof.

8. A compound as claimed in claim 7 wherein
$R_1$ is H or OH,
each $R_2$ is independently H or $NH_2$ and
each $R_3$ is $CH_2NH_2$.

* * * * *